US008962249B2

(12) United States Patent
Abbas et al.

(10) Patent No.: US 8,962,249 B2
(45) Date of Patent: Feb. 24, 2015

(54) METHODS FOR DETECTING AND TREATING SYSTEMIC LUPUS ERYTHEMATOUS

(75) Inventors: Alexander Abbas, Belmont, CA (US); Barmak Modrek, San Mateo, CA (US); Michael J. Townsend, San Jose, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/333,775

(22) Filed: Dec. 21, 2011

(65) Prior Publication Data

US 2012/0295799 A1 Nov. 22, 2012

Related U.S. Application Data

(63) Continuation of application No. 12/749,524, filed on Mar. 30, 2010, now abandoned, which is a continuation of application No. 11/739,606, filed on Apr. 24, 2007, now abandoned.

(60) Provisional application No. 60/794,393, filed on Apr. 24, 2006.

(51) Int. Cl.
*C12Q 1/68* (2006.01)
*C40B 30/04* (2006.01)
*A61K 39/395* (2006.01)
*A61K 39/00* (2006.01)
*G06F 19/18* (2011.01)

(52) U.S. Cl.
CPC .............. *C12Q 1/6883* (2013.01); *G06F 19/18* (2013.01); *C12Q 2600/158* (2013.01); *C12Q 2600/112* (2013.01)
USPC ..... 435/6.11; 435/6.1; 424/130.1; 424/141.1; 424/145.1; 506/9

(58) Field of Classification Search
None
See application file for complete search history.

(56) References Cited

U.S. PATENT DOCUMENTS

| 5,143,854 | A | 9/1992 | Pirrung et al. |
|---|---|---|---|
| 5,744,305 | A | 4/1998 | Fodor et al. |
| 6,905,827 | B2 | 6/2005 | Wohlgemuth et al. |
| 7,026,121 | B1 | 4/2006 | Wohlgemuth et al. |
| 7,118,865 | B2 | 10/2006 | Behrens et al. |
| 7,608,395 | B2* | 10/2009 | Pascual et al. ............... 435/6.11 |
| 2001/0036631 | A1 | 11/2001 | Mcgrath et al. |
| 2003/0148298 | A1 | 8/2003 | O'Toole et al. |
| 2004/0009479 | A1 | 1/2004 | Wohlgemuth et al. |
| 2004/0033498 | A1 | 2/2004 | Behrens et al. |
| 2004/0191818 | A1 | 9/2004 | O'Toole et al. |
| 2005/0208041 | A1* | 9/2005 | Cardarelli et al. ......... 424/141.1 |
| 2006/0018875 | A1 | 1/2006 | Blatt et al. |
| 2006/0100132 | A1* | 5/2006 | Corneliussen et al. ........... 514/2 |
| 2006/0177814 | A1 | 8/2006 | Behrens et al. |
| 2007/0014724 | A1* | 1/2007 | Witte et al. ................. 424/1.49 |
| 2007/0031890 | A1 | 2/2007 | Wohlgemuth et al. |
| 2007/0037144 | A1 | 2/2007 | Wohlgemuth et al. |
| 2007/0037166 | A1 | 2/2007 | Wohlgemuth et al. |
| 2007/0037167 | A1 | 2/2007 | Wohlgemuth et al. |
| 2007/0048301 | A1 | 3/2007 | Bodary-Winter et al. |
| 2007/0092890 | A1 | 4/2007 | Abbas |
| 2008/0057503 | A1 | 3/2008 | Abbas |
| 2010/0267033 | A1 | 10/2010 | Abbas |
| 2010/0279298 | A1 | 11/2010 | Abbas |
| 2013/0338019 | A1 | 12/2013 | Abbas |

FOREIGN PATENT DOCUMENTS

| CA | 2649918 | A | 11/2008 |
|---|---|---|---|
| EP | 2 537 943 | B1 | 3/2014 |
| EP | 2 080 814 | B1 | 4/2014 |
| EP | 2 557 180 | B1 | 7/2014 |
| WO | 00/22093 | A2 | 4/2000 |
| WO | 00/22093 | A3 | 4/2000 |
| WO | 02/057414 | A2 | 7/2002 |
| WO | 03/090694 | A2 | 11/2003 |
| WO | 03/090694 | A3 | 11/2003 |
| WO | 2004/046098 | A2 | 6/2004 |
| WO | 2004047728 | A2 | 6/2004 |
| WO | 2005/016962 | | 2/2005 |
| WO | 2005/051988 | | 6/2005 |
| WO | 2006/020899 | A2 | 2/2006 |
| WO | 2006088438 | A1 | 8/2006 |
| WO | 2007/019219 | A2 | 2/2007 |
| WO | 2007/035651 | A3 | 3/2007 |
| WO | WO-2012/149228 | A1 | 11/2012 |

OTHER PUBLICATIONS

Kalunian et al. (Lupus Research Presented at 2012 American College of Rheumatology Annual Scientific Meeting. Dec. 3, 2012, available via url: <lupus.org/webmodules/webarticlesnet/templates/indiana_programs.aspx?articleid=4836&zoneid=370.*
Fossey et al. The Journal of Molecular Diagnostics. 2007. 9: 197-204.*
Pettit et al. Trends Biotechnol. 1998.16: 343-349.*
Thomas et al Nature. 2003.4: 346-358.*
Raterman et al. Arthritis Res Ther. 2012. 14(2): R95.*
U.S. Appl. No. 12/749,522, filed Mar. 30, 2010, Abbas et al.
"SLE: Targets for New Therapeutics—A Scientific Conference, Salmon et al. (organizers), Jan. 10-12, 2002, Hyatt Regency Bethesda, Bethesda, Maryland." (Conference summary of selected presentations) pp. 8.
('GeneChip Human Genome U133 Set' www.affymetrix.com/ (Retrieved from Internet on Sep. 4, 2007) pp. 1).
Baechler, et al., "Interferon-inducible gene expression signature in peripheral blood cells of patients with severe lupus" Proc. Natl. Acad. Sci. USA 100(5):2610-2615 (Mar. 4, 2003).
Balomenos et al., "Interferon-gamma is required for lupus-like disease and lyphoaccumulation in MRL-1pr mice" J Clin Invest 101(2):364-371 (Jan. 15, 1998).

(Continued)

*Primary Examiner* — Carla Myers
(74) *Attorney, Agent, or Firm* — Morrison & Foerster LLP

(57) ABSTRACT

The invention provides methods and compositions useful for detecting autoimmune disorders.

8 Claims, 4 Drawing Sheets

(56) References Cited

OTHER PUBLICATIONS

Bauer et al., "Elevated Serum Levels of Interferon-Regulated Chemokines are Biomarkers for Active Human Systemic Lupus Erythematosus" PLoS Medicine 3(12):2274-2284 (Dec. 19, 2006).
Blanco et al., "Induction of dendritic cell differentiation by IFN-alpha in systemic lupus erythematosus" Science 294(5546):1540-1543 (Nov. 16, 2001).
Coleman et al., "Of mouse and man—what is the value of the mouse in predicting gene expressions in humans?" Drug Discov Today 8(6):223-235 (Mar. 15, 2003).
Crow, et al., "Microarray analysis of gene expressions in lupus" Arthritis Research and Therapy 5:(6):279-287 (Oct. 13, 2003).
Crow, et al., "Microarray analysis of interferon-regulated genes in SLE" Autoimmunity 36(8):481-490 (Dec. 2003).
de Veer et al., "Functional classification of interferon-stimulated genes identified using microarrays" J Leukoc Biol 69(6):912-920 (Jun. 2001).
Der et al., "Identification of genes differentially regulated by interferon alpha, beta, or gamma using oligonucleotide arrays" P Natl Acad Sci USA 95(26):15623-15628 (Dec. 22, 1998).
Diaz et al. et al., "Nomenclature of the human interferon genes" J Interferon Res 13(6):443-444 (Dec. 1993).
Domanski et al., "Cloning and expression of a long form of the beta subunit of the interferon alpha beta receptor that is required for signaling" J Biol Chem 270(37):21606-21611 (Sep. 15, 1995).
Fukuyama et al., "Systemic lupus erythematosus after alpha-interferon therapy for chronic hepatitis C: a case report and review of the literature" Am J Gastroenterol 95(1):310-312 (Jan. 2000).
Gu et al., "Analysis of inflammation related gene expression spectrum in ankylosing spondylitis patients using cDNA microarray (Abstract only)" Zhonghua Yi Xue Za Zhi 81(17):1030-1034 (Sep. 10, 2001).
Han, et al., "Analysis of gene expression profiles in human systemic lupus erythematosus using oligonucleotide microarray" Genes and Immunity 4(3):177-186 (Apr. 2003).
Hirano et al., "Roles of STAT3 in mediating the cell growth, differentiation and survival signals relayed through the IL-6 family of cytokine receptors"Oncogene 19(21):2548-2556 (May 15, 2000).
Hochberg, "Updating the American College of Rheumatology revised criteria for the classification of systemic lupus erythematosus" Arthritis Rheum 40(9):1725 (Sep. 1997).
Ishii et al., "Isolation and Expression Profiling of Genes Upregulated in the Peripheral Blood Cells of Systemic Lupus Erythematosus Patients" DNA Research 12:429-439 (2005).
Jacob et al., "In vivo treatment of (NZB X NZW)F1 lupus-like nephritis with monoclonal antibody to gamma interferon" J Exp Med 166(3):798-803 (Sep. 1, 1987).
Liu et al., "Comparison of differentially expressed genes in T lymphocytes between human autoimmune disease and murine models of autoimmune disease" Clin Immunol. 112(3):225-230 (Sep. 2004).
Ronnblom and Alm et al., "A pivotal role for the natural interferon alpha-producing cells (plasmacytoid dendritic cells) in the pathogenesis of lupus" J Exp Med 194(12):F59-F63 (Dec. 17, 2001).
Rozzo et al., "Evidence for an interferon-inducible gene, Ifi202, in the susceptibility to systemic lupus" Immunity 15(3):435-443 (Sep. 2001).
Saetre et al., "From wild wolf to domestic dog: gene expression changes in the brain" Molecular Brain Research 126:198-206 (2004).
Seery et al., "Antinuclear autoantibodies and lupus nephritis in transgenic mice expressing interferon gamma in the epidermis" J Exp Med 186(9):1451-1459 (Nov. 3, 1997).
Singh et al., "The use of cDNA microarrays to investigate changes in gene expression in the involuting bovine mammary gland" Proc. of the New Zealand Society of Animal Production 64:8-10 (2004).
Tan et al., "The 1982 revised criteria for the classification of systemic lupus erythematosus" Arthritis Rheum 25(11):1271-1277 (Nov. 1982).
Uze et al., "Genetic transfer of a functional human interferon alpha receptor into mouse cells: cloning and expression of its cDNA" Cell 60(2):225-234 (Jan. 26, 1990).
Weissman & Weber Prog Nucleic Acid Res Mol Biol.Academic Press, vol. 33:251-300 (1986).
Kalunian, K. et al. "Efficacy and Safety of Rontalizumab (Anti-Interferon-Alpha) in SLE Patients with Restricted Immunosuppressant Use: Results of a Randomized, Double-Blind, Placebo-Controlled Phase 2 Trial," Presented at ACR (Dec. 3, 2012), 22 pages.
Min et al. (2010), "Variability of Gene Expression Profiles in Human Blood and Lymphoblastoid Cell Lines," BMC Genomics (2010), 11(96):1-14.
Palmer et al. (May 16, 2006). "Cell-Type Specific Gene Expression Profiles of Leukocytes in Human Peripheral Blood," BMC Genomics 7(115):1-15.
'GeneChip Human Genome U133 Set' www.affymetrix.com/support/technical/datasheets/hqu333_datasheet.pdf (Internet citation) retrieved Feb. 26, 2003, pp. 1-2.
Gene card OAS1 (www.genecards.org/cgi-bin/carddisp.pl?gene=OAS1&search=oas1&suff=txt,, pp. 1-10, Aug. 9, 2007).
Gene card LY6E (www.gencards.org/cgi-bin/carddisp.pl?gene=LY6E&search=ly6e&suff=txt, pp. 1-9, Aug. 9, 2007).
Liu et al., "Identification of Gene Expression signatures in autoimmune disease without the influence of familial resemblance" Human Molecular Genetics 15(3):501-509 (2006).
Olsen et al., "Gene Expression signatures for autoimmune disease in peripheral blood mononuclear cells" Arthritis Research and Therapy 6(3):120-128 ( 2004).
Rajeevan et al., "Use of Real-Time Quantitative PCT to Validate the Results of cDNA Array and Differential Display PCR Technologies" Methods 25(4):443-451 (Dec. 2001).
Rajeevan et al., "Validation of Array-Based Gene Expression Profiles by Real-Time (Kinetic) PT-PCR" Journal of Molecular Diagnostics 3(1):26-31 (Feb. 2001).
Rasar et al., "Noise in Gene Expression: Origins, Consequences, and Control" Science 309:2010-2013 (2005).
Winstead, Edward R., "Images of Imprinting" Genome News Network pp. 1-2 (Apr. 7, 2000).
Salmon et al. Summary of selected presentations from SLE: Targets for New Therapeutics—A Scientific Conference, Salmon et al. (organizers), Jan. 10-12, 2002, Hyatt Regency Bethesda, Bethesda, Maryland. (2002).

* cited by examiner

Rho values of Spearman correlation of probes to the IRG signature reveal the extent of the region containing IRG signal.

METHODS FOR DETECTING AND TREATING SYSTEMIC LUPUS ERYTHEMATOUS

RELATED APPLICATION

This application is a continuation of U.S. patent application Ser. No. 12/749,524, filed on Mar. 3, 2010 now abandoned, which is a continuation of U.S. patent application Ser. No. 11/739,606 filed on Apr. 24, 2007 now abandoned, claiming priority under 35 USC 119(e) to U.S. Provisional Application Ser. No. 60/794,393 filed on Apr. 24, 2006, all of which are hereby incorporated herein in their entirety

TECHNICAL FIELD

The present invention relates generally to the fields of molecular determination of autoimmune diseases. More specifically, the invention concerns methods and compositions based on unique molecular signatures associated with various aspects of autoimmune disorders.

BACKGROUND

A number of autoimmune disorders are now believed to be characterized by the production of autoantibodies against a variety of self antigens. For example, systemic lupus erythematous (SLE) is an autoimmune disease in which autoantibodies cause organ damage by binding to host cells and tissues and by forming immune complexes that deposit in vascular tissues and activate immune cells. Sjogren's syndrome is an autoimmune disease characterized by inflammation in the glands of the body. Other autoimmune disorders are also commonly found, including but not limited to IgA nephropathy, psoriasis, rheumatoid arthritis, multiple sclerosis, ankylosing spondylitis, etc.

Interferon alpha (IFN-α) is a Type I interferon strongly implicated in the etiology of a number of immune disorders, such as SLE. It is believed that treatment approaches involving disruption of IFN-α signaling may be an effective treatment for such disorders. IFN-α levels are known to be elevated in SLE, and treatment of patients with IFN-α has been observed to reversibly cause symptoms similar to SLE in recipients. Numerous other lines of evidence have linked IFN-α and SLE.

The mechanisms by which IFN-α exerts its effects on the transcription of genes in target cells has been extensively investigated. The second messenger cascade has been determined, cis-regulatory binding sites for activated transcription factors have been defined, and several studies have explored what genes' expression is modulated. The most comprehensive of these studies have been performed with oligonucleotide microarrays, but definitions of interferon response gene expression profiles are still not complete, at least in part because until recently microarrays have not contained a very complete set of reporters for the genes of the human genome, and also because a variety of technical difficulties prevented identification of broadly applicable yet simple sets of marker genes that reliably correlate with pathological conditions of interest.

One of the most difficult challenges in clinical management of autoimmune diseases is the accurate and early identification of the diseases in a patient. To this end, it would be highly advantageous to have molecular-based diagnostic methods that can be used to objectively identify presence and/or extent of disease in a patient. The invention described herein provides these methods and other benefits.

All references cited herein, including patent applications and publications, are incorporated by reference in their entirety.

DISCLOSURE OF THE INVENTION

The invention provides methods and compositions for identifying autoimmune disorders based at least in part on identification of the gene(s) whose expression is associated with presence and/or extent of systemic lupus erythematosus (SLE), wherein SLE is in turn a prototypical autoimmune disease whose disease-associated gene signatures are also applicable in other autoimmune diseases. For example, as described herein, in one embodiment, genes modulated in response to signaling by IFN-α were identified. Information generated by this approach was then tested and modified to develop a concise and quantitative measure of the degree to which cell or tissue samples exhibit responses characteristic of autoimmune disorders. As shown herein, detection of one or more of specific genes disclosed herein can be a useful and informative indicator of presence and/or extent of autoimmune disorders in a patient. Moreover, metrics or equivalent quotients that are indicative of interferon-associated disease presentation and/or severity can be generated by appropriate transformation of biomarker gene expression information. Exemplary transformations and resultant metrics are disclosed herein, generated based on gene expression data that are also disclosed herein.

In one aspect, the invention provides a method comprising determining whether a subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or any number up to all of the genes listed in Table 1, 2 and/or 3 at a level greater than the expression level of the respective genes in a normal reference sample, wherein presence of said, cell indicates that the subject has an autoimmune disorder.

In one aspect, the invention provides a method of predicting responsiveness of a subject to autoimmune disease therapy, said method comprising determining whether the subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 at a level greater than the expression level of the respective genes in a normal reference sample, wherein presence of said cell indicates that the subject would be responsive to the autoimmune disease therapy.

In one aspect, the invention provides a method for monitoring minimal residual disease in a subject treated for an autoimmune disease, said method comprising determining whether the subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 at a level greater than the expression level of the respective genes in a normal reference sample, wherein detection of said cell is indicative of presence of minimal residual autoimmune disease.

In one aspect, the invention provides a method for detecting an autoimmune disease state in a subject, said method comprising determining whether the subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 at a level greater than the expression level of the respective genes in a normal reference sample, wherein detection of said cell is indicative of presence of an autoimmune disease state in the subject.

In one aspect, the invention provides a method for assessing predisposition of a subject to develop an autoimmune disorder, said method comprising determining whether the subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 at a level greater than the expression level of the respective genes in a normal reference sample, wherein detection of said cell is indicative of a predisposition for the subject to develop the autoimmune disorder.

In one aspect, the invention provides a method for diagnosing an autoimmune disorder in a subject, said method comprising determining whether the subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 at a level greater than the expression level of the respective genes in a normal reference sample, wherein detection of said cell indicates that the subject has said autoimmune disorder.

In one aspect, the invention provides a method for distinguishing between active and inactive disease states (e.g., active and inactive SLE) in a subject, said method comprising determining whether the subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 at a level greater than the expression level of the respective genes in a normal reference sample, wherein detection of said cell indicates that the subject has the autoimmune disorder in an active state.

In one aspect, the invention provides a method for determining presence and/or elevation of anti-dsDNA antibodies in a subject, said method comprising determining whether the subject comprises a cell that expresses at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 at a level greater than the expression level of the respective genes in a normal reference sample, wherein detection of said cell indicates presence and/or elevation of anti-dsDNA antibodies in the subject.

Methods of the invention provide information useful for determining appropriate clinical intervention steps, if and as appropriate. Therefore, in one embodiment of a method of the invention, the method further comprises a clinical intervention step based on results of the assessment of the expression of one or more of the genes listed in Table 1, 2 and/or 3 (including, e.g., any combination of genes (e.g., those listed in Table 4)). For example, appropriate intervention may involve prophylactic and treatment steps, or adjustment(s) of any then-current prophylactic or treatment steps based on gene expression information obtained by a method of the invention.

As would be evident to one skilled in the art, in any method of the invention, while detection of increased expression of a gene would positively indicate a characteristic of a disease (e.g., presence, stage or extent of a disease), non-detection of increased expression of a gene would also be informative by providing the reciprocal characterization of the disease.

In one aspect, the invention provides a composition comprising polynucleotides capable of specifically hybridizing to at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3, or complements of such genes. In one embodiment, the polynucleotides are provided as an array, gene chip, or gene set (e.g., a set of genes or fragments thereof, provided separately or as a mixture).

In one aspect, the invention provides a kit comprising a composition the invention, and instructions for using the composition to detect an autoimmune disorder by determining whether expression of at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3 are at a level greater than the expression level of the respective genes in a normal reference sample. In one embodiment, the composition of the invention comprises an array/gene chip/gene set capable of specifically hybridizing to at least 2, 3, 4, 5, 6, 7, 8, 9, 10, 11, 12, 13, 14, 15, 16, 17, 18, 19, 20, 21, 22, 23, 24, 25, 26, 27, 28 or or any number up to all of the genes listed in Table 1, 2 and/or 3. In one embodiment, the composition of the invention comprises nucleic acid molecules encoding at least a portion of a polypeptide encoded by a gene listed in Table 1, 2 and/or 3. In one embodiment, the composition of the invention comprises nucleic acid primers capable of binding to and effecting polymerization (e.g., amplification) of at least a portion of a gene listed in Table 1, 2 and/or 3. In one embodiment, the composition of the invention comprises a binding agent (e.g., primer, probe) that specifically detects a gene (or complement thereof) (or corresponding gene product) listed in Table 1, 2 and/or 3. In one embodiment, the composition of the invention comprises a binding agent that specifically binds to at least a portion of a polypeptide encoded by a gene listed in Table 1, 2 and/or 3.

Methods and compositions of the invention may comprise one or more of the genes listed in Table 1, 2 and/or 3. If more than one gene is utilized or included in a method or composition of the invention, the more than one gene can be any combination of any number of the genes as listed (in no particular order) in Table 1, 2 and/or 3. For example, in one embodiment, a combination of genes comprises only two genes that are listed, namely OAS3 and HERC5. In one embodiment, a combination of genes comprises only three, only four, only five, or only six genes that are listed. In one embodiment, a combination of genes comprises at least two, at least three, at least four, at least five, or at least six genes that are listed. In another embodiment, a combination of genes comprises OAS3, HERC5, and one or more of the other genes listed in Table 1, 2 and/or 3. In one embodiment, a gene combination of the invention comprises, consists, or consists essentially of a 3-gene combination (Genes 1, 2 and 3) as indicated in Table 4B. In one embodiment, such 3-gene combination is indicated as having a Pearson correlation value of at least about 0.7, or at least about 0.75, or at least about 0.8, or at least about 0.85, or at least about 0.9, or at least about 0.95, or at least about 0.97, or at least about 0.98, or at least about 0.99. In one embodiment, such 3-gene combination comprises (1) IFIT4, OAS1, and MX1; or (2) OASL, CHMP5, and ZBP1; or (3) IFI44L, OASL, and CIG5; or (4) IFI44L, CIG5, and ZBP1; or (5) EPSTI1, TYKI, and MX1; or (6) IFIT4, HERC5, and TYKI; or (7) IFIT4, TYKI, and XIAP; or (8) IFI44L, OASL, and ZBP1; or (9) IFI44L, IFIT4, and OASL; or (10) IFI4, OAS1, and IFIT1; or (11) EPSTI1, HERC5, and TYKI; or (12) IFI44L, EPSTI1, and OASL; or (13) IFI44L, EPSTI1, and OAS3; or (14) EPSTI1, TYKI, and IFIT1; or (15) G1P2, SAMD9L, and SP110. In yet another embodiment, a combination of genes comprises one or more of the genes listed in Table 1, 2 and/or 3, further combined with one or more other genes that are not listed in Table 1, 2 and/or 3 (e.g., a gene known to be associated with an autoimmune disease but not associated with induction by interferons specifically).

In any of the embodiments of the invention described herein, one or more reference genes (i.e., genes that, when assessed by themselves, are not known to be indicative of the disease and/or condition of interest) may be included. Such reference genes may include housekeeping genes. For example, suitable reference genes may be housekeeping genes that can serve as reference/control genes indicative of baseline gene expression levels in a sample. Thus, for example, in one embodiment, one or more genes listed in Tables 1, 2, 3 and/or 4 are used in combination with one or more housekeeping genes such as ribosomal protein L19 (RPL19; NP_000972), glyceraldehyde-3-phosphate dehydrogenase (GAPDH), actins (e.g. β-actin), tubulins, hypoxantine phsophoribosyltransferase (HRPT), and other ribosomal proteins/genes (e.g., 28S,18S).

In one aspect, the invention provides a method of identifying a metric value correlated with presence and/or extent of an autoimmune disorder in a subject or sample, said method comprising:

(a) estimating a group of probesets that is collectively associated with a pattern wherein expression of genes represented by the probesets is associated with a disease characteristic;

(b) generating a weighting factor that weight probesets in accordance with a scale reflecting extent of match of each individual probeset to trend of the group of probesets, and calculating the correlation coefficient of each probeset's profile to the mean profile calculated;

(c) determining a scaling factor, wherein the scaling factor is the value required to scale individual probesets to 1;

(d) multiplying the scaling factor by the weighting factor to generate a composite factor;

(e) multiplying a normal blood sample's signatures with the composite factor, and the averaging the resulting values across both probesets and samples to generate an average value, and inverting the average value to yield a global scaling factor;

(f) multiplying each weighting factor by the global scaling factor to obtain a vector of scalar values, and multiplying the scalar values by an expression signature from a sample of interest, and averaging the resulting values to yield a single metric that is indicative of degree of gene expression associated with Type I interferons in the sample.

In one embodiment of the method of the preceding paragraph, in step (a), the group of probesets comprises probesets that include, or cluster around, the core most-tightly-correlated pair of probesets in subcluster associated with a disease characteristic.

In one embodiment of the method of the preceding paragraphs, in step (b), the factor is generated by transforming expression data of the group of probesets into z-scores comprising mean scaling to 1, base-2 log transformation, then scaling to a standard deviation of the mean of 1.

In one embodiment of the method of the preceding paragraphs, in step (e), the global scaling factor is useful for transforming output of the average of probesets from a sample of interest into a metric, wherein the metric is 1 if the sample is from a normal, healthy subject.

In one embodiment of the method of any of the preceding paragraphs, the group of probesets comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or or any number up to all of those listed in Table 1, 2 and/or 3. In one embodiment, the group of probesets comprises all those listed in Table 1, 2 and/or 3.

In one aspect, the invention provides a method comprising comparing a first metric obtained by a method described herein for a sample obtained from a subject of interest to a reference metric obtained from a reference (e.g., normal, healthy, non-diseased) sample, wherein a first metric that is higher than a reference metric indicates presence of an autoimmune disorder in the subject of interest.

In one aspect, the invention provides a method of predicting responsiveness of a subject to autoimmune disease therapy, said method comprising comparing a first metric obtained by a method described herein for a sample obtained from the subject to a reference metric obtained from a reference (e.g., normal, healthy, non-diseased) sample, wherein a first metric that is higher than a reference metric indicates the subject would be responsive to the autoimmune disease therapy.

In one aspect, the invention provides a method for monitoring minimal residual disease in a subject treated for an autoimmune disease, said method comprising comparing a first metric obtained by a method described herein for a sample obtained from the subject to a reference metric obtained from a reference (e.g., normal, healthy, non-diseased and/or untreated) sample, wherein a first metric that is higher than a reference metric is indicative of presence of minimal residual autoimmune disease.

In one aspect, the invention provides a method for detecting an autoimmune disease state, said method comprising comparing a first metric obtained by a method described herein for a sample from a subject suspected of having the autoimmune disease state to a reference metric obtained from a reference (e.g., normal, healthy, non-diseased) sample, wherein a first metric that is higher than a reference metric is indicative of presence of the autoimmune disease state in the subject.

In one aspect, the invention provides a method for assessing predisposition of a subject to develop an autoimmune disorder, said method comprising comparing a first metric obtained by a method described herein for a sample obtained from the subject to a reference metric obtained from a reference (e.g., normal, healthy, non-diseased) sample, wherein a first metric that is higher than a reference metric is indicative of a predisposition for the subject to develop the autoimmune disorder.

In one aspect, the invention provides a method for diagnosing an autoimmune disorder in a subject, said method comprising comparing a first metric obtained by a method described herein for a sample obtained from the subject to a reference metric obtained from a reference (e.g., normal, healthy, non-diseased) sample, wherein a first metric that is higher than a reference metric indicates that the subject has said autoimmune disorder.

In one aspect, the invention provides a method for distinguishing between active and inactive disease states (e.g., active and inactive SLE) in a subject, said method comprising comparing a first metric obtained by a method described herein for a sample obtained from the subject to a reference metric obtained from a reference (e.g., normal, healthy, non-diseased) sample, wherein a first metric that is higher than a reference metric indicates that the subject has the autoimmune disorder in an active state.

In one aspect, the invention provides a method for determining presence and/or elevation of anti-dsDNA antibodies in a subject, said method comprising comparing a first metric obtained by a method described herein for a sample obtained from the subject to a reference metric obtained from a reference (e.g., normal, healthy, non-diseased) sample, wherein a first metric that is higher than a reference metric indicates presence and/or elevation of anti-dsDNA antibodies in the subject.

In one embodiment, a reference metric is obtained using a method described herein for a sample from a control sample (e.g., as obtained from a healthy and/or non-diseased and/or untreated tissue, cell and/or subject).

The steps in the methods for examining expression of one or more biomarkers may be conducted in a variety of assay formats, including assays detecting mRNA expression (including but not limited to converting mRNA to cDNA, optionally followed by nucleic acid amplification), enzymatic assays detecting presence of enzymatic activity, and immunohistochemistry assays. Optionally, the tissue or cell sample comprises disease tissue or cells.

Still further methods of the invention include methods of treating a disorder in a mammal, such as an immune related disorder, comprising steps of obtaining tissue or a cell sample from the mammal, examining the tissue or cells for expression (e.g., amount of expression) of one or more biomarkers, and upon determining said tissue or cell sample expresses said one or more biomarkers (e.g., wherein the biomarkers are expressed in amounts greater than a reference (control) sample), administering an effective amount of a therapeutic agent to said mammal. The steps in the methods for examining expression of one or more biomarkers may be conducted in a variety of assay formats, including assays detecting mRNA expression, enzymatic assays detecting presence of enzymatic activity, and immunohistochemistry assays. Optionally, the methods comprise treating an autoimmune disorder in a mammal. Optionally, the methods comprise administering an effective amount of a targeted therapeutic agent (e.g., an antibody that binds and/or blocks activity of Type 1 interferons and/or their corresponding receptor(s)), and, optionally, a second therapeutic agent (e.g., steroids, etc.) to said mammal.

In some embodiments, biomarkers are selected from those listed in Tables 1, 2 and/or 3.

MODES FOR CARRYING OUT THE INVENTION

General Techniques

Figure 1:
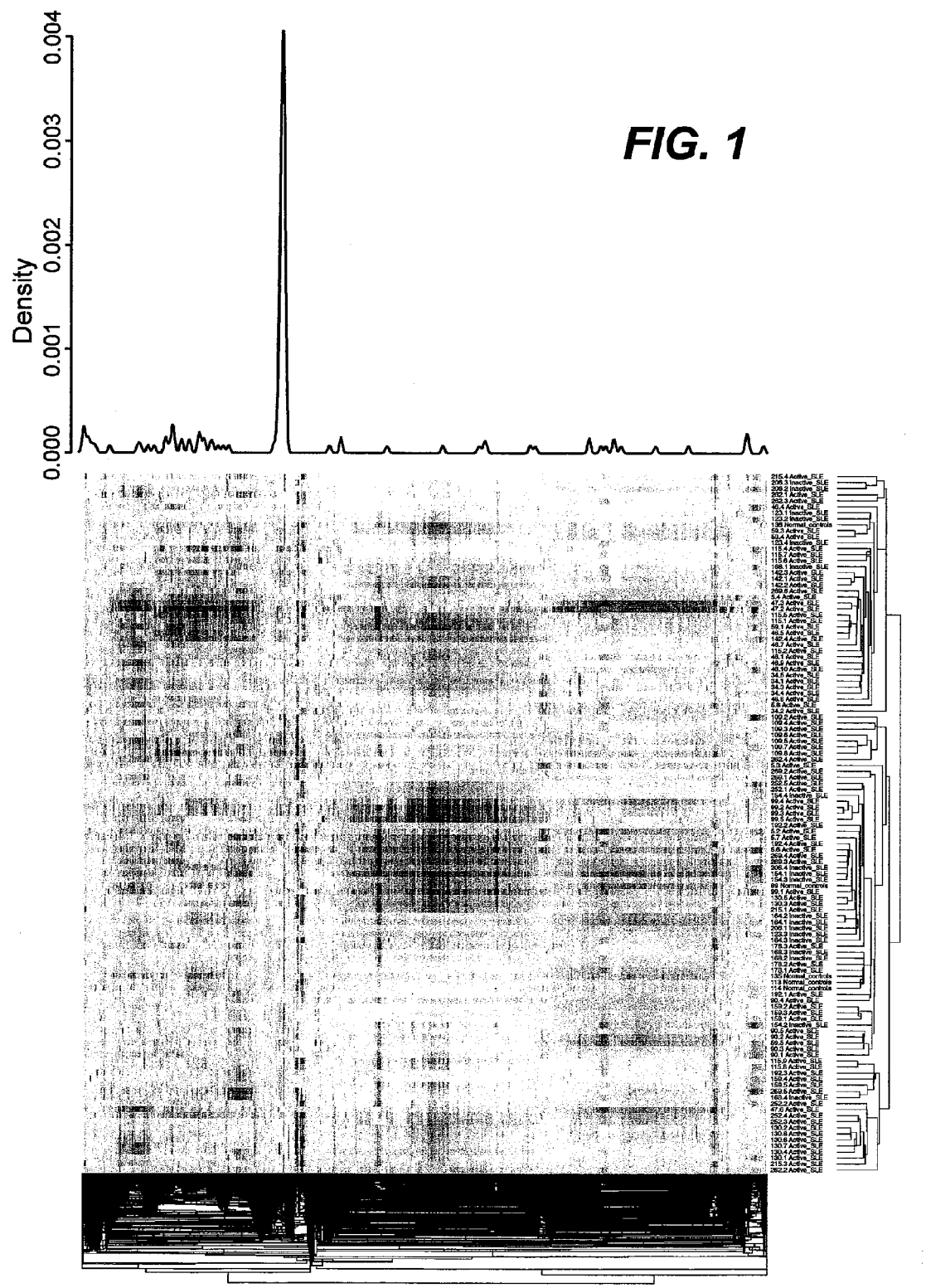
FIG. 1. Alignment of a density plot of interferon-induced genes with a 2D hierarchical cluster heatmap of control and SLE patient samples shows a single region highly enriched in interferon-induced genes.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

DEFINITIONS

The term "array" or "microarray", as used herein refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane. The nucleotide sequences can be DNA, RNA, or any permutations thereof.

A "target sequence", "target nucleic acid" or "target protein", as used herein, is a polynucleotide sequence of interest, in which a mutation of the invention is suspected or known to reside, the detection of which is desired. Generally, a "template," as used herein, is a polynucleotide that contains the target nucleotide sequence. In some instances, the terms "target sequence," "template DNA," "template polynucleotide," "target nucleic acid," "target polynucleotide," and variations thereof, are used interchangeably.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

Expression/amount of a gene or biomarker in a first sample is at a level "greater than" the level in a second sample if the expression level/amount of the gene or biomarker in the first sample is at least about 1.5×, 1.75×, 2×, 3×, 4×, 5×, 6×, 7×, 8×, 9× or 10× the expression level/amount of the gene or biomarker in the second sample. Expression levels/amounts can be determined based on any suitable criterion known in the art, including but not limited to mRNA, cDNA, proteins, protein fragments and/or gene copy. Expression levels/amounts can be determined qualitatively and/or quantitatively.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A "primer" is generally a short single stranded polynucleotide, generally with a free 3'-OH group, that binds to a target potentially present in a sample of interest by hybridizing with a target sequence, and thereafter promotes polymerization of a polynucleotide complementary to the target.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "mutation", as used herein, means a difference in the amino acid or nucleic acid sequence of a particular protein or nucleic acid (gene, RNA) relative to the wild-type protein or nucleic acid, respectively. A mutated protein or nucleic acid can be expressed from or found on one allele (heterozygous) or both alleles (homozygous) of a gene, and may be somatic or germ line.

To "inhibit" is to decrease or reduce an activity, function, and/or amount as compared to a reference.

The term "3'" generally refers to a region or position in a polynucleotide or oligonucleotide 3' (downstream) from another region or position in the same polynucleotide or oligonucleotide. The term "5'" generally refers to a region or position in a polynucleotide or oligonucleotide 5' (upstream) from another region or position in the same polynucleotide or oligonucleotide.

"Detection" includes any means of detecting, including direct and indirect detection.

The term "diagnosis" is used herein to refer to the identification of a molecular or pathological state, disease or condition, such as the identification of an autoimmune disorder. The term "prognosis" is used herein to refer to the prediction of the likelihood of autoimmune disorder-attributable disease symptoms, including, for example, recurrence, flaring, and drug resistance, of an autoimmune disease. The term "prediction" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

The term "long-term" survival is used herein to refer to survival for at least 1 year, 5 years, 8 years, or 10 years following therapeutic treatment.

The term "increased resistance" to a particular therapeutic agent or treatment option, when used in accordance with the invention, means decreased response to a standard dose of the drug or to a standard treatment protocol.

The term "decreased sensitivity" to a particular therapeutic agent or treatment option, when used in accordance with the invention, means decreased response to a standard dose of the agent or to a standard treatment protocol, where decreased response can be compensated for (at least partially) by increasing the dose of agent, or the intensity of treatment.

"Patient response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

The term "interferon inhibitor" as used herein refers to a molecule having the ability to inhibit a biological function of wild type or mutated Type 1 interferon. Accordingly, the term "inhibitor" is defined in the context of the biological role of Type 1 interferon. In one embodiment, an interferon inhibitor referred to herein specifically inhibits cell signaling via the Type 1 interferon/interferon receptor pathway. For example, an interferon inhibitor may interact with (e.g. bind to) interferon alpha receptor, or with a Type 1 interferon which normally binds to interferon receptor. In one embodiment, an interferon inhibitor binds to the extracellular domain of interferon alpha receptor. In one embodiment, an interferon inhibitor binds to the intracellular domain of interferon alpha receptor. In one embodiment, an interferon inhibitor binds to Type 1 interferon. In one embodiment, the Type 1 interferon is an interferon alpha subtype. In one embodiment, the Type 1 interferon is not interferon beta. In one embodiment, the Type 1 interferon is not interferon omega. In one embodiment, interferon biological activity inhibited by an interferon inhibitor is associated with an immune disorder, such as an autoimmune disorder. An interferon inhibitor can be in any form, so long as it is capable of inhibiting interferon/receptor activity; inhibitors include antibodies (e.g., monoclonal antibodies as defined hereinbelow), small organic/inorganic molecules, antisense oligonucleotides, aptamers, inhibitory peptides/polypeptides, inhibitory RNAs (e.g., small interfering RNAs), combinations thereof, etc.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs/HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR/HVR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "blocking" antibody or an "antagonist" antibody is one which inhibits or reduces biological activity of the antigen it binds. Such blocking can occur by any means, e.g. by interfering with protein-protein interaction such as ligand binding to a receptor. In on embodiment, blocking antibodies or antagonist antibodies substantially or completely inhibit the biological activity of the antigen.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE) (including but not limited to lupus nephritis, cutaneous lupus); diabetes mellitus (e.g. Type I diabetes mellitus or insulin dependent diabetes mellitus); multiple sclerosis; Reynaud's syndrome; autoimmune thyroiditis; Hashimoto's thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, methods and compositions of the invention are useful in attempts to delay development of a disease or disorder.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

As used herein, the terms "type I interferon" and "human type I interferon" are defined as all species of native human and synthetic interferon which fall within the human and synthetic interferon-α, interferon-ω and interferon-β classes and which bind to a common cellular receptor. Natural human interferon-α comprises 23 or more closely related proteins encoded by distinct genes with a high degree of structural homology (Weissmann and Weber, *Prog. Nucl. Acid. Res. Mol. Biol.*, 33: 251 (1986); *J. Interferon Res.*, 13: 443-444 (1993)). The human IFN-α locus comprises two subfamilies. The first subfamily consists of at least 14 functional, non-allelic genes, including genes encoding IFN-αA (IFN-α2), IFN-αB (IFN-α8), IFN-α (IFN-α10), IFN-αD (IFN-α1), IFN-αE (IFN-α22), IFN-αF (IFN-α21), IFN-αG (IFN-α5), IFN-α16, IFN-α17, IFN-α4, IFN-α6, IFN-α7, and IFN-αH (IFN-α14), and pseudogenes having at least 80% homology. The second subfamily, $α_{II}$ or ω, contains at least 5 pseudogenes and 1 functional gene (denoted herein as "IFN-$α_{II}$" or "IFN-ω") which exhibits 70% homology with the IFN-α genes (Weissmann and Weber (1986)). The human IFN-β is generally thought to be encoded by a single copy gene.

Figure 5:
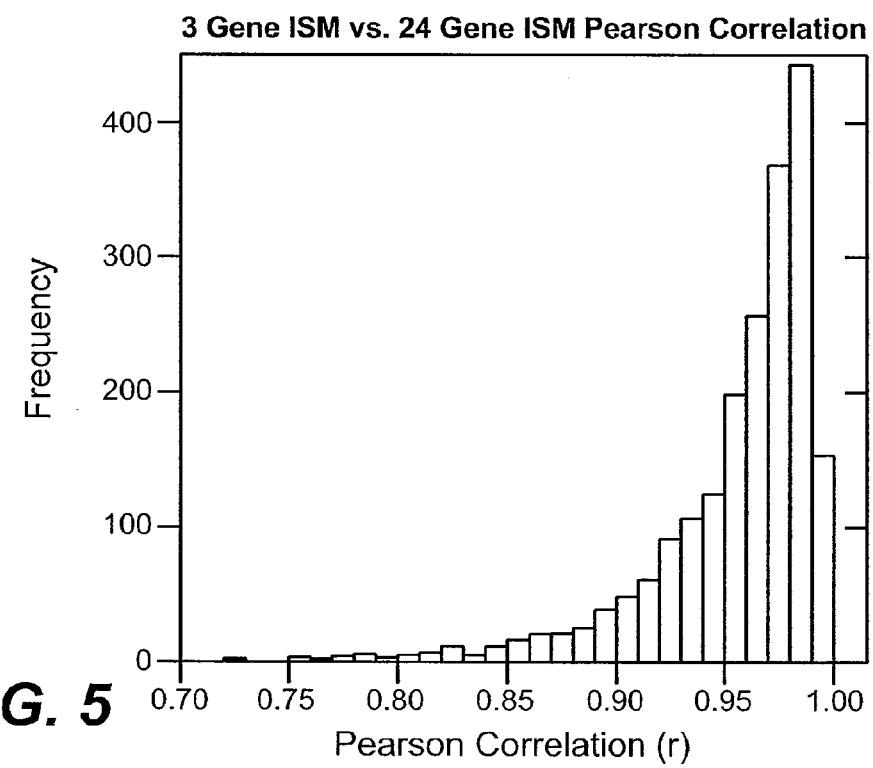
FIG. 5. Three-gene combination versus 24-gene combination Pearson correlation illustrated as a histogram.

As used herein, the terms "first human interferon-α (hIFN-α) receptor", "IFN-αR", "hIFNAR1", "IFNAR1", and "Uze chain" are defined as the 557 amino acid receptor protein cloned by Uze et al., *Cell*, 60: 225-234 (1990), including an extracellular domain of 409 residues, a transmembrane domain of 21 residues, and an intracellular domain of 100 residues, as shown in FIG. 5 on page 229 of Uze et al. In one embodiment, the foregoing terms include fragments of IFNAR1 that contain the extracellular domain (ECD) (or fragments of the ECD) of IFNAR1.

As used herein, the terms "second human interferon-α (hIFN-α) receptor", "IFN-αPR", "hIFNAR2", "IFNAR2", and "Novick chain" are defined as the 515 amino acid receptor protein cloned by Domanski et al., *J. Biol. Chem.*, 37: 21606-21611 (1995), including an extracellular domain of 217 residues, a transmembrane domain of 21 residues, and an intracellular domain of 250 residues, as shown in FIG. 1 on page 21608 of Domanski et al. In one embodiment, the foregoing terms include fragments of IFNAR2 that contain the extracellular domain (ECD) (or fragments of the ECD) of IFNAR2, and soluble forms of IFNAR2, such as IFNAR2ECD fused to at least a portion of an immunoglobulin sequence.

The term "housekeeping gene" refers to a group of genes that codes for proteins whose activities are essential for the maintenance of cell function. These genes are typically similarly expressed in all cell types. Housekeeping genes include, without limitation, ribosomal protein L19 (NP_000972), glyceraldehyde-3-phosphate dehydrogenase (GAPDH), Cyp1, albumin, actins (e.g. β-actin), tubulins, cyclophilin, hypoxantine phosphoribosyltransferase (HRPT), ribosomal protein L32 (NP_001007075), and ribosomal protein/genes 28S (e.g., Q9Y399) and 18S.

The term "biomarker" as used herein refers generally to a molecule, including a gene, protein, carbohydrate structure, or glycolipid, the expression of which in or on a mammalian tissue or cell can be detected by standard methods (or methods disclosed herein) and is predictive, diagnostic and/or prognostic for a mammalian cell's or tissue's sensitivity to treatment regimes based on inhibition of interferons, e.g. Type 1 interferons. Optionally, the expression of such a biomarker is determined to be higher than that observed for a control/reference tissue or cell sample. Optionally, for example, the expression of such a biomarker will be determined in a PCR or FACS assay to be at least about 5-fold, at least about 10-fold, at least about 20-fold, at least about 30-fold, at least about 40-fold, at least about 50-fold, or preferably at least about 100-fold higher in the test tissue or cell sample than that observed for a control tissue or cell sample. Optionally, the expression of such a biomarker will be determined in an IHC assay to score at least 2 or higher for staining intensity. Optionally, the expression of such a biomarker will be determined using a gene chip-based assay.

An "IRG" or "interferon response gene" or "interferon responsive gene", as used herein, refers to one or more of the genes, and corresponding gene products, listed in Table 1, 2, 3 and/or 4. As shown herein, aberrant expression levels/amounts of one or more of these genes are correlated with a variety of autoimmune disorders. As would be evident to one skilled in the art, depending on context, the term IRG can refer to nucleic acid (e.g., genes) or polypeptides (e.g., proteins) having the designation or unique identifier listed in Table 1, 2, 3 and/or 4.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like. A "reference sample", "reference cell", or "reference tissue", as used herein, refers to a sample, cell or tissue obtained from a source known, or believed, not to be afflicted with the disease or condition for which a method or composition of the invention is being used to identify. In one embodiment, a reference sample, reference cell or reference tissue is obtained from a healthy part of the body of the same subject or patient in whom a disease or condition is being identified using a composition or method of the invention. In one embodiment, a reference sample, reference cell or reference tissue is obtained from a healthy part of the body of an individual who is not the subject or patient in whom a disease or condition is being identified using a composition or method of the invention.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

General Illustrative Techniques

A sample comprising a target molecule can be obtained by methods well known in the art, and that are appropriate for the particular type and location of the disease of interest. Tissue biopsy is often used to obtain a representative piece of disease tissue. Alternatively, cells can be obtained indirectly in the form of tissues/fluids that are known or thought to contain the disease cells of interest. For instance, samples of disease lesions may be obtained by resection, bronchoscopy, fine needle aspiration, bronchial brushings, or from sputum, pleural fluid or blood. Genes or gene products can be detected from disease tissue or from other body samples such as urine, sputum or serum. The same techniques discussed above for detection of target genes or gene products in disease samples can be applied to other body samples. Disease cells are sloughed off from disease lesions and appear in such body samples. By screening such body samples, a simple early diagnosis can be achieved for these diseases. In addition, the progress of therapy can be monitored more easily by testing such body samples for target genes or gene products.

In one embodiment, methods of the invention are useful for detecting any autoimmune disorder with which abnormal activation (e.g., overexpression) of interferons, in particular Type 1 interferons and/or their associated signaling pathway, is associated. The diagnostic methods of the present invention are useful for clinicians so that they can decide upon an appropriate course of treatment. For example, a sample from a subject displaying a high level of expression of the genes or gene products disclosed herein might suggest a more aggressive therapeutic regimen than a sample exhibiting a comparatively lower level of expression. Methods of the invention can be utilized in a variety of settings, including for example in aiding in patient selection during the course of drug development, prediction of likelihood of success when treating an individual patient with a particular treatment regimen, in assessing disease progression, in monitoring treatment efficacy, in determining prognosis for individual patients, in assessing predisposition of an individual to develop a particular autoimmune disorder (e.g., systemic lupus erythematosus, Sjogren's syndrome), in differentiating disease staging, etc.

Means for enriching a tissue preparation for disease cells are known in the art. For example, the tissue may be isolated from paraffin or cryostat sections. Disease cells may also be separated from normal cells by flow cytometry or laser capture microdissection. These, as well as other techniques for separating disease from normal cells, are well known in the art. If the disease tissue is highly contaminated with normal cells, detection of signature gene expression profile may be more difficult, although techniques for minimizing contamination and/or false positive/negative results are known, some of which are described hereinbelow. For example, a sample may also be assessed for the presence of a biomarker (including a mutation) known to be associated with a disease cell of interest but not a corresponding normal cell, or vice versa.

The invention also provides a variety of compositions suitable for use in performing methods of the invention. For example, the invention provides arrays that can be used in such methods. In one embodiment, an array of the invention comprises individual or collections of nucleic acid molecules useful for detecting mutations of the invention. For instance, an array of the invention may comprises a series of discretely placed individual nucleic acid oligonucleotides or sets of nucleic acid oligonucleotide combinations that are hybridizable to a sample comprising target nucleic acids, whereby such hybridization is indicative of presence or absence of a mutation of the invention.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into nucleic acid molecules that are synthesized. The synthesized product is then contacted with a solid substrate, such as a glass slide, which is coated with an aldehyde or another reactive group which will form a covalent link with the reactive group that is on the amplified product and become covalently attached to the glass slide. Other methods, such as those using amino propryl silican surface chemistry are also known in the art, as disclosed at url: <cmt.corning.com> and url: <cmgm.stanford.edu/pbrown1>.

Attachment of groups to oligonucleotides which could be later converted to reactive groups is also possible using methods known in the art. Any attachment to nucleotides of oligonucleotides will become part of oligonucleotide, which could then be attached to the solid surface of the microarray.

Amplified nucleic acids can be further modified, such as through cleavage into fragments or by attachment of detectable labels, prior to or following attachment to the solid substrate, as required and/or permitted by the techniques used.

Typical Methods and Materials of the Invention

The methods and assays disclosed herein are directed to the examination of expression of one or more biomarkers in a mammalian tissue or cell sample, wherein the determination of that expression of one or more such biomarkers is predictive or indicative of whether the tissue or cell sample will be sensitive to treatment based on the use of interferon inhibitors. The methods and assays include those which examine expression of biomarkers such as one or more of those listed in Table 1, 2 and/or 3.

As discussed above, there are some populations of diseased human cell types that are associated with abnormal expression of interferons such as the Type 1 interferons which is associated with various autoimmune disorders. It is therefore believed that the disclosed methods and assays can provide for convenient, efficient, and potentially cost-effective means to obtain data and information useful in assessing appropriate or effective therapies for treating patients. For example, a patient having been diagnosed with an immune related condition could have a biopsy performed to obtain a tissue or cell sample, and the sample could be examined by way of various in vitro assays to determine whether the patient's cells would be sensitive to a therapeutic agent such as an interferon inhibitor (e.g., an anti-interferon alpha antibody or an antibody to interferon alpha receptor).

The invention provides methods for predicting the sensitivity of a mammalian tissue or cells sample (such as a cell associated with an autoimmune disorder) to an interferon inhibitor. In the methods, a mammalian tissue or cell sample is obtained and examined for expression of one or more biomarkers. The methods may be conducted in a variety of assay formats, including assays detecting mRNA expression, enzymatic assays detecting presence of enzymatic activity, and immunohistochemistry assays. Determination of expression of such biomarkers in said tissues or cells will be predictive that such tissues or cells will be sensitive to the interferon inhibitor therapy. Applicants surprisingly found that the expression of such particular biomarkers correlates closely with presence and/or extent of various autoimmune disorders.

As discussed below, expression of various biomarkers in a sample can be analyzed by a number of methodologies, many of which are known in the art and understood by the skilled artisan, including but not limited to, immunohistochemical and/or Western analysis, quantitative blood based assays (as for example Serum ELISA) (to examine, for example, levels of protein expression), biochemical enzymatic activity assays, in situ hybridization, Northern analysis and/or PCR analysis of mRNAs, as well as any one of the wide variety of assays that can be performed by gene and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis).

The protocols below relating to detection of particular biomarkers, such as those listed in Table 1, 2 and/or 3, in a sample are provided for illustrative purposes.

Optional methods of the invention include protocols which examine or test for presence of IRG in a mammalian tissue or cell sample. A variety of methods for detecting IRG can be employed and include, for example, immunohistochemical analysis, immunoprecipitation, Western blot analysis, molecular binding assays, ELISA, ELIFA, fluorescence activated cell sorting (FACS) and the like. For example, an optional method of detecting the expression of IRG in a tissue or sample comprises contacting the sample with a IRG antibody, a IRG-reactive fragment thereof, or a recombinant protein containing an antigen binding region of a IRG antibody; and then detecting the binding of IRG protein in the sample.

In particular embodiments of the invention, the expression of IRG proteins in a sample is examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, tissue biopsy, blood, lung aspirate, sputum, lymph fluid, etc. The sample can be obtained by a variety of procedures known in the art including, but not limited to surgical excision, aspiration or biopsy. The tissue may be fresh or frozen. In one embodiment, the sample is fixed and embedded in paraffin or the like.

The tissue sample may be fixed (i.e. preserved) by conventional methodology (See e.g., "Manual of Histological Staining Method of the Armed Forces Institute of Pathology," 3$^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Optionally, subsequent to the sample preparation, a tissue section may be analyzed using IHC. IHC may be performed in combination with additional techniques such as morphological staining and/or fluorescence in-situ hybridization.

Two general methods of IHC are available; direct and indirect assays. According to the first assay, binding of antibody to the target antigen (e.g., an IRG) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology*, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Optionally, the antibodies employed in the IHC analysis to detect expression of an IRG are antibodies generated to bind primarily to the IRG of interest. Optionally, the anti-IRG antibody is a monoclonal antibody. Anti-IRG antibodies are readily available in the art, including from various commercial sources, and can also be generated using routine skills known in the art.

Specimens thus prepared may be mounted and coverslipped. Slide evaluation is then determined, e.g. using a microscope, and staining intensity criteria, routinely used in the art, may be employed. As one exmple, staining intensity criteria may be evaluated as follows:

TABLE A

| Staining Pattern | Score |
| --- | --- |
| No staining is observed in cells. | 0 |
| Faint/barely perceptible staining is detected in more than 10% of the cells. | 1+ |
| Weak to moderate staining is observed in more than 10% of the cells. | 2+ |
| Moderate to strong staining is observed in more than 10% of the cells. | 3+ |

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labelled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labelled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

It is contemplated that the above described techniques may also be employed to detect expression of IRG.

Methods of the invention further include protocols which examine the presence and/or expression of mRNAs, such as IRG mRNAs, in a tissue or cell sample. Methods for the evaluation of mRNAs in cells are well known and include, for example, hybridization assays using complementary DNA probes (such as in situ hybridization using labeled IRG riboprobes, Northern blot and related techniques) and various nucleic acid amplification assays (such as RT-PCR using complementary primers specific for IRG, and other amplification type detection methods, such as, for example, branched DNA, SISBA, TMA and the like).

Tissue or cell samples from mammals can be conveniently assayed for, e.g., IRG mRNAs using Northern, dot blot or PCR analysis. For example, RT-PCR assays such as quantitative PCR assays are well known in the art. In an illustrative embodiment of the invention, a method for detecting an IRG mRNA in a biological sample comprises producing cDNA from the sample by reverse transcription using at least one primer; amplifying the cDNA so produced using an IRG polynucleotide as sense and antisense primers to amplify IRG cDNAs therein; and detecting the presence of the amplified IRG cDNA. In addition, such methods can include one or more steps that allow one to determine the levels of IRG mRNA in a biological sample (e.g. by simultaneously examining the levels a comparative control mRNA sequence of a "housekeeping" gene such as an actin family member). Optionally, the sequence of the amplified IRG cDNA can be determined.

Material embodiments of this aspect of the invention include IRG primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of IRG polynucleotides in a sample and as a means for detecting a cell expressing IRG proteins. As will be understood by the skilled artisan, a great many different primers and probes may be prepared based on the sequences provided in herein and used effectively to amplify, clone and/or determine the presence and/or levels of IRG mRNAs.

Optional methods of the invention include protocols which examine or detect mRNAs, such as IRG mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, *Nature Biotechnology*, 14:1675-1680 (1996); Cheung, V. G. et al., Nature Genetics 21 (Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commerically available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from Genbank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

The expression of a selected biomarker may also be assessed by examining gene deletion or gene amplification. Gene deletion or amplification may be measured by any one of a wide variety of protocols known in the art, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe. By way of example, these methods may be employed to detect deletion or amplification of IRG genes.

Expression of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

In the methods of the present invention, it is contemplated that the tissue or cell sample may also be examined for the expression of interferons such as Type 1 interferons, and/or activation of the Type 1 interferon signaling pathway, in the sample. Examining the tissue or cell sample for expression of Type 1 interferons and/or the corresponding receptor(s), and/or activation of the Type interferon signaling pathway, may give further information as to whether the tissue or cell sample will be sensitive to an interferon inhibitor. By way of example, the IHC techniques described above may be employed to detect the presence of one of more such molecules in the sample. It is contemplated that in methods in which a tissue or sample is being examined not only for the presence of IRG, but also for the presence of, e.g., Type 1 interferon, interferon receptor(s), separate slides may be prepared from the same tissue or sample, and each slide tested with a reagent specific for each specific biomarker or receptor. Alternatively, a single slide may be prepared from the tissue or cell sample, and antibodies directed to each biomarker or receptor may be used in connection with a multicolor staining protocol to allow visualization and detection of the respective biomarkers or receptors.

Subsequent to the determination that the tissue or cell sample expresses one or more of the biomarkers indicating the tissue or cell sample will be sensitive to treatment with interferon inhibitors, it is contemplated that an effective amount of the interferon inhibitor may be administered to the mammal to treat a disorder, such as autoimmune disorder which is afflicting the mammal. Diagnosis in mammals of the various pathological conditions described herein can be made by the skilled practitioner. Diagnostic techniques are available in the art which allow, e.g., for the diagnosis or detection of autoimmune related disease in a mammal.

An interferon inhibitor can be administered in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through mini-pump infusion using various commercially available devices.

Effective dosages and schedules for administering interferon inhibitors may be determined empirically, and making such determinations is within the skill in the art. Single or multiple dosages may be employed. For example, an effective dosage or amount of interferon inhibitor used alone may range from about 1 μg/kg to about 100 mg/kg of body weight or more per day. Interspecies scaling of dosages can be performed in a manner known in the art, e.g., as disclosed in Mordenti et al., *Pharmaceut. Res.*, 8:1351 (1991).

When in vivo administration of interferon inhibitor is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

It is contemplated that yet additional therapies may be employed in the methods. The one or more other therapies may include but are not limited to, administration of steroids and other standard of care regimens for the particular autoimmune disorder in question. It is contemplated that such other therapies may be employed as an agent separate from the interferon inhibitor.

For use in the applications described or suggested above, kits or articles of manufacture are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for IRG gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kits of the invention have a number of embodiments. A typical embodiment is a kit comprising a container, a label on said container, and a composition contained within said container; wherein the composition includes a primary antibody that binds to a IRG polypeptide sequence, the label on said container indicates that the composition can be used to evaluate the presence of IRG proteins in at least one type of mammalian cell, and instructions for using the IRG antibody for evaluating the presence of IRG proteins in at least one type of mammalian cell. The kit can further comprise a set of instructions and materials for preparing a tissue sample and applying antibody and probe to the same section of a tissue sample. The kit may include both a primary and secondary antibody, wherein the secondary antibody is conjugated to a label, e.g., an enzymatic label.

Another embodiment is a kit comprising a container, a label on said container, and a composition contained within said container; wherein the composition includes a polynucleotide that hybridizes to a complement of the IRG polynucleotide under stringent conditions, the label on said container indicates that the composition can be used to evaluate the presence of IRG in at least one type of mammalian cell, and instructions for using the IRG polynucleotide for evaluating the presence of IRG RNA or DNA in at least one type of mammalian cell.

Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

The following are examples of the methods and compositions of the invention. It is understood that various other embodiments may be practiced, given the general description provided above.

EXAMPLES

Example 1

Materials and Methods

Expression of IFN-alpha responsive genes (IRG's) was analyzed in data from blood—peripheral blood mononuclear cells (PBMC) from SLE patients (with active or inactive disease) and normal donors from the University Of Minnesota (Minneapolis, Minn.).

Data was produced as follows: 92 blood samples were collected on different dates from 18 patients with active SLE, 19 blood samples were collected on different dates from 5 patients with inactive SLE, and 4 blood samples were collected from 4 healthy donors. PBMC was isolated from whole blood by standard Ficoll gradient centrifugation. RNA was prepared from PBMC samples using RNA Isolation Kit from Qiagen (Valencia, Calif.) and hybridized to WHG oligonucleotide microarray chips from Agilent (Palo Alto, Calif.). Raw data was processed by standard Agilent Feature Extraction to yield Agilent log ratio data. Normal expression of genes in response to IFN-alpha was examined by isolating PBMC from healthy donors and incubating it in culture for four hours with 100 U/ml recombinant IFN-alpha, then taking samples of the cell culture at 4, 12, 28, and 52 hours following addition of IFN-alpha.

Microarray data was clustered hierarchically in two dimensions (samples and probes) using the xcluster software program (pearson on log 2 signal) on probes with both mean signal in the top 70% ile and coefficient of variability in the top 70% ile. Cluster data was viewed with the Java Treeview software program. Numerical analysis was performed with R (url: <r-project.org>), JMP (SAS Institute, Cary, N.C.) and Excel (Microsoft, Redmond, Wash.).

Results and Analysis

Microarray clustering of all samples showed significant grouping of both samples and genes. Sample clustering showed grouping of a large fraction of SLE patients with active disease. Gene clustering showed several different tightly grouped gene subclusters with obvious biological patterns. For instance, one subcluster was highly enriched for genes known to be specific to B cells, another to neutrophils, another for antibodies, and another for IRG's. The IRG subcluster showed an interesting pattern with respect to samples: normal samples all showed low expression of IRG's, while SLE samples showed a wide range of expression that varied from normal-like to extremely high.

The expression profiles of probes within a tight subcluster are very similar but not identical, and the variation between very similar profiles may be due in significant part to noise either from biological or technological sources. For instance, some genes are represented on the microarray by more than one probe, and there are several pairs of probes in the IRG subcluster area that represent the same gene's expression. In these cases, the probes clustered near to each other, sometimes immediately adjacent. Thus it appeared that a clear pattern was present and reflected in many probes, and that utilizing the data from several probes in order to mitigate the interference of noise in the data might most clearly identify the pattern. Nonetheless, the genes that were identified could be used individually as genetic identifiers that correlate with presence of disease.

Identification of Genes Highly Induced by Interferon Alpha

In order to identify genes whose expression is highly induced by the presence of interferon alpha, PBMC samples from healthy donors were treated with recombinant interferon alpha and samples of the cell cultures were subjected to Agilent WHG expression analysis as described above. Log ratio data from these hybridizations were analyzed by two-way ANOVA (time and treatment), and 142 probes were identified by filtering of treatment p-value $<5\times10^{-7}$. This set of genes is a subset of genes whose expression is induced by interferon alpha, and it constitutes an effective tool for identifying clusters of genes in other experiments whose common basis for co-clustering is induction by interferon alpha.

Development of a Metric that Correlates with Disease, and Identification of Individual Genes that May Constitute Such Metric The pattern of transcriptional activation in IRG's was measured by calculating a single metric proportional to the Agilent ratio levels of the specific subgroup of probes. For example, we describe this approach below with the IRG probes. The pattern (the aggregate profile of IRG's) was first defined by aligning a density plot of probes induced by interferon alpha in PBMC samples with the cluster heatmap of SLE and control samples (FIG. 1). Probes were defined as IRG's by starting from the two most highly correlated probes and expanding the set by adding the next most highly correlated probe or branch of probes until the set of probes appeared to contain most of the expression signature evident in its center but not so far that it contains a significant contribution from a different signature. The set is comprised of the thirty-five probes listed in Table 1.

The expression data of this group was then transformed into z-scores (mean scaled to 1, base-2 log transformed, then scaled to a standard deviation of the mean of 1), and the correlation coefficient of each probe's profile to the mean profile was calculated. These correlation coefficients were used as weighting factors to weight relatively heavily the probes that showed the strongest match to the trend of the group, and to weight relatively lightly those that apparently were more affected by other inputs or noise.

The factors required to scale probes to 1 were multiplied by the weighting factor, to produce a composite factor that could yield a normalized, weighted metric for a single hybridization. The normal blood samples' signatures were multiplied by that factor, averaged across both probes and samples, and this number was inverted to yield a global scaling factor that would transform the output of the average of probes from a sample into a metric that would be expected to be 1 for samples from healthy donors. Each normalization/weighting factor was multiplied by this factor. The result was a vector of scalar values that were multiplied by a sample expression signature and averaged to yield the Type I Interferon Response Gene Metric (IRGM), a single metric measuring the level of IFN-alpha transcriptional response in a sample.

Figure 2:
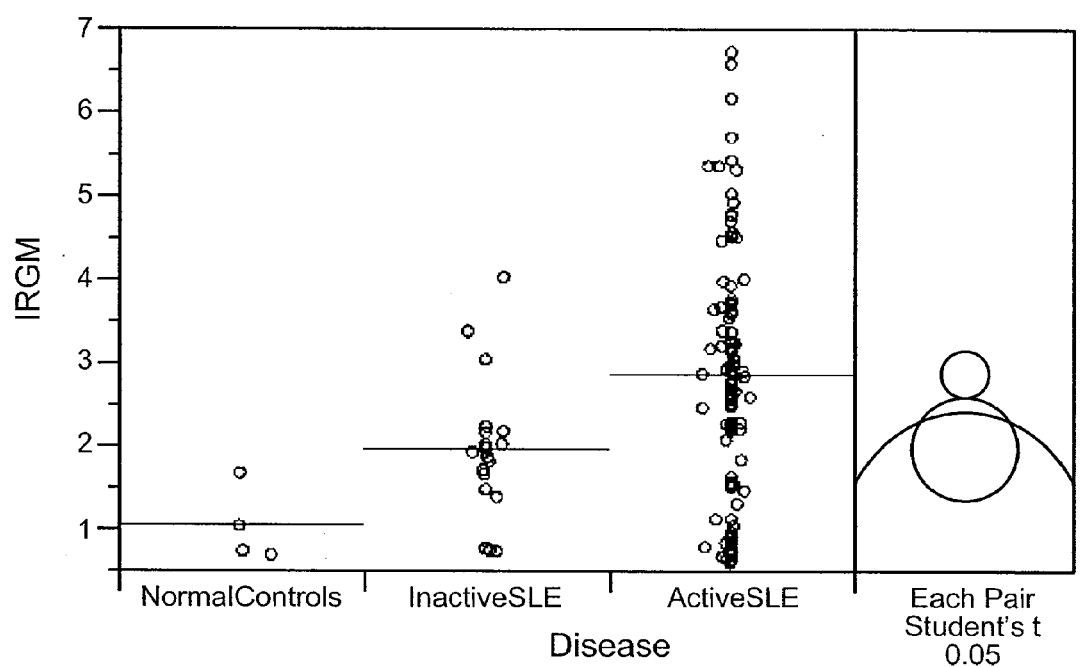
FIG. 2. IRGM scores from Active SLE patients are significantly higher than normal controls.

IRGM scores were calculated and evaluated for the set of clinical samples used for selection of the IRGM genes. IRGM scores were significantly higher for patients suffering from active SLE than healthy patients (FIG. 2).

Figure 3A:
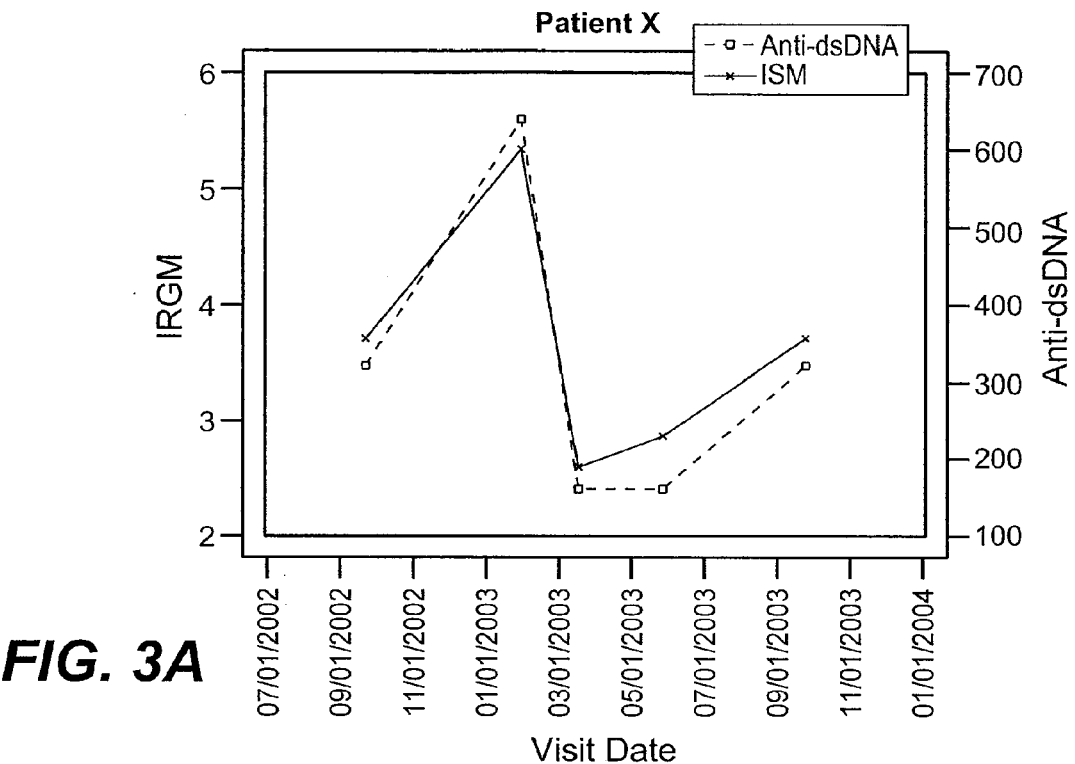
FIG. 3. Examples of SLE patients whose IRGM and anti-dsDNA levels are well correlated.
Figure 3B:
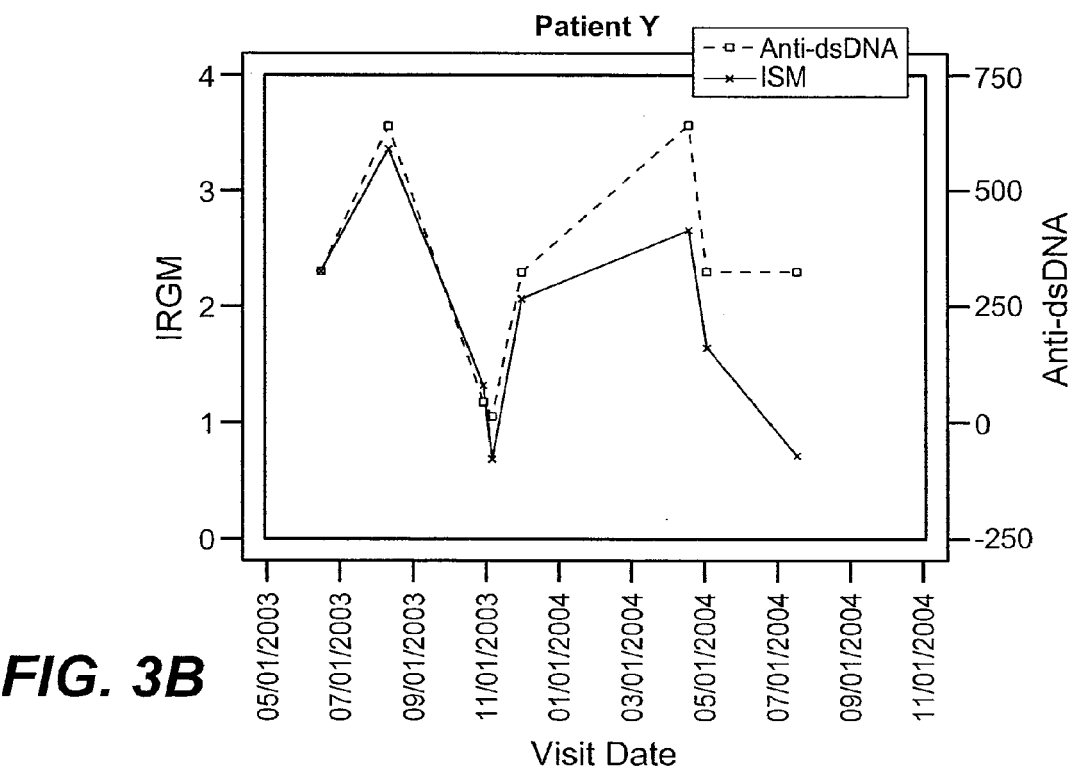

Clinical measures of SLE disease activity and severity such as SLEDAI quantitate patient disease symptoms and may correlate with expression of genes that underlie the etiology of the disease. In order to investigate this hypothesis, IRGM data on individual patients were compared to those patients' clinical scores and lab test results. No significant correlation was observed between IRGM and SLEDAI, but the titer of anti-dsDNA antibodies in serum correlated well with IRGM in many patients with active SLE (FIG. 3). This correlation could be the basis of either assay being a surrogate for the other. It also illustrates a biological relationship that could serve as a basis for a rational design of therapy for SLE.

The IRGM test, and expression of the genes that make up such a test (as set forth in Table 1), could be useful for selecting patients that would benefit from IFN-α-based treatment for autoimmune disorders (e.g., SLE) by identifying patients that have a relatively high IRGM score and thus have IFN-α signaling that could be blocked. Equivalently, it could be used to predict that certain patients would not benefit from IFN-α-based treatment because they do not exhibit a high IRGM score and thus are not currently experiencing active IFN-α signaling that could be disrupted.

The IRGM test, and expression of the genes that make up such a test (as set forth in Table 1), are useful indicators in a variety of drug development, diagnostic, prognostic and therapeutic settings as described above. For example, this information could be used to check whether patients that have responded well to anti-IFN-α treatment had high levels of expression of the signaling targets of IFN-α before treatment and afterwards whether the treatment abrogated that expression. It would be a useful gauge of the extent to which a particular treatment affects the IFN-α signaling pathway. It might be a useful bio- or pharmacodynamic marker, measuring the profile of the effects of treatment over time.

Other Interferons

The metric-based approach described above could be utilized in a variety of ways in characterizing disease pathways, mechanisms of action and drug pharmacodynamics. For example, different interferon molecules probably have different properties that the IRGM and/or a test made the same way based on different microarray data and/or analyses could help measure and elucidate. For instance:

1) Type I interferons all signal through the same heterodimeric receptor but may differ in their half-life, receptor affinity, or power to initiate signaling in a target cell. These differences in magnitudes might be measured easily and accurately by IRGM. This sort of measurement could be carried out either in a cell culture experiment or in a clinical setting. Likewise, the effect of candidate drugs or drugs used in clinical settings can be gauged using this approach.

2) Different IRGM-like tests could be constructed by microarray assays of cultured blood samples treated with different interferons. To the extent to which the tests differ from each other, they could be applied to clinical samples to determine the relative activities of different interferons and/or drugs.

Other Signatures

The method used to generate the IRGM test could also be applied to any sort of expression signature, either of a state or activity of cells or of a type of cell or cells. For instance, some SLE patients show marked upmodulation of immunoglobulin gene expression, an indicator of the production of antibodies by plasma cells. Microarray probes reporting expression of these genes could collectively support the calculation of a measurement of the overall level of plasma cell activity and antibody production. In another example, there are particular transcriptional changes associated with active mitotic cell replication. These transcriptional changes could be consolidated into a test that would be applied to a variety of biological samples to measure how actively they are dividing. Or in yet another example, the genes whose expression is specific to particular types of immune cells could be categorized by which cell type expresses them and then for each cell type a test could be made. This collection of tests could then be applied to any of a variety of clinical samples (blood from SLE patients, intestinal biopsies from Crohn's Disease patients, etc.) to determine the balance of immune cell types.

TABLE 1

Agilent WHG probes constituting a set of IRG's for WHG analysis. Thirty five probes are listed, representing twenty nine unique genes. Refseq or Genbank accession numbers, symbols and names of genes are also indicated.

| probeid | accession | gene symbol | gene description |
|---|---|---|---|
| A_24_P343929 | NM_001032731 | OAS2 | 2'-5'-oligoadenylate synthetase 2 |
| A_24_P395966 | NM_030776 | ZBP1 | Z-D binding protein 1 |
| A_23_P259141 | NM_030776 | ZBP1 | Z-D binding protein 1 |
| A_23_P139786 | NM_003733 | OASL | 2'-5'-oligoadenylate synthetase-like |
| A_24_P316965 | NM_080657 | RSAD2 (CIG5) | radical S-adenosyl methionine domain containing 2 |
| A_23_P17663 | NM_002462 | MX1 | myxovirus resistance 1 |
| A_24_P378019 | NM_001572 | IRF7 | interferon regulatory factor 7 |
| A_23_P64828 | NM_001032409 | OAS1 | 2',5'-oligoadenylate synthetase 1 |
| A_24_P943205 | NM_001002264 | EPSTI1 | epithelial stromal interaction 1 |
| A_23_P23074 | NM_006417 | IFI44 | interferon-induced protein 44 |
| A_23_P45871 | NM_006820 | IFI44L | interferon-induced protein 44-like |
| A_23_P819 | NM_005101 | G1P2 | interferon, alpha-inducible protein IFI-15K |
| A_24_P28722 | NM_080657 | RSAD2 (CIG5) | radical S-adenosyl methionine domain containing 2 |
| A_24_P917810 | NM_000059 | BRCA2 | breast cancer 2, early onset |
| A_23_P52266 | NM_001001887 | IFIT1 | interferon-induced protein with tetratricopeptide repeats 1 |
| A_23_P110196 | NM_016323 | HERC5 | hect domain and RLD 5 |
| A_23_P47955 | NM_006187 | OAS3 | 2'-5'-oligoadenylate synthetase 3 |
| A_23_P35412 | NM_001031683 | IFIT3 | interferon-induced protein with tetratricopeptide repeats 3 |
| A_24_P557479 | NM_017523 | HSXIAPAF1 | XIAP associated factor-1 |
| A_23_P4283 | NM_017523 | HSXIAPAF1 | XIAP associated factor-1 |
| A_32_P132206 | NM_017414 | USP18 | ubiquitin specific peptidase 18 |
| A_24_P317762 | NM_002346 | RIG-E | lymphocyte antigen 6 complex, locus E |
| A_24_P316257 | NM_145270 | FLJ36208 | hypothetical protein FLJ36208 |
| A_23_P105794 | NM_001002264 | EPSTI1 | epithelial stromal interaction 1 |
| A_23_P166797 | NM_022147 | TMEM7 | 28 kD interferon responsive protein |
| A_23_P111804 | NM_022750 | PARP12 | poly (ADP-ribose) polymerase family, member 12 |
| A_23_P250353 | NM_001013000 | HERC6 | hect domain and RLD 6, transcript variant 3 |
| A_24_P334361 | NM_017631 | SGRA12061 | hypothetical protein FLJ20035 |
| A_23_P384355 | NM_207315 | TYKI | thymidylate kinase family LPS-inducible |
| A_24_P30194 | NM_012420 | IFIT5 | interferon-induced protein with tetratricopeptide repeats 5 |
| A_23_P4286 | NM_017523 | HSXIAPAF1 | XIAP associated factor-1, transcript variant 1 |
| A_32_P227059 | AA977193 | (no symbol) | (no known gene) |
| A_23_P142750 | NM_002759 | EIF2AK2 | eukaryotic translation initiation factor 2-alpha kinase 2 |
| A_24_P161018 | NM_017554 | PARP14 | poly (ADP-ribose) polymerase family, member 14 |
| A_24_P335305 | NM_006187 | OAS3 | 2'-5'-oligoadenylate synthetase 3 |

Example 2

Materials and Methods

Expression of IFN-alpha responsive genes (IRG's) was analyzed in data from white blood cells (WBC) from SLE patients and healthy donors obtained by Gene Logic Inc. (Gaithersburg, Md.).

Data was produced as follows: 72 blood samples were collected from patients with active SLE, 46 blood samples were collected from healthy donors. RNA was prepared from WBC samples using RNA Isolation Kit from Qiagen (Valencia, Calif.) and hybridized to HGU133 oligonucleotide microarray chips from Affymetrix, Inc. (Santa Clara, Calif.). Raw data was processed by Affymetrix MAS5.0 feature extraction to yield Signal data.

Microarray data was clustered hierarchically in two dimensions (samples and probes) using the xcluster software program (pearson on log 2 signal) on probes with both mean signal in the top 70% ile and coefficient of variability in the top 70% ile. Cluster data was viewed with the Java Treeview software program. Numerical analysis was performed with R (url: <r-project.org>), JMP (SAS Institute, Cary, N.C.).

Results and Analysis

Microarray clustering of all samples showed significant grouping of both samples and genes. Sample clustering showed grouping of a large fraction of SLE patients with active disease. Gene clustering showed several different tightly grouped gene subclusters with obvious biological patterns. For instance, one subcluster was highly enriched for genes known to be specific to B cells, another to neutrophils, another for antibodies, and another for IRG's. The IRG subcluster showed an interesting pattern with respect to samples: normal samples all showed low expression of IRG's, while SLE samples showed a wide range of expression that varied from normal-like to extremely high.

The expression profiles of probes within a tight subcluster were very similar but not identical, and the variation between very similar profiles may be due in significant part to noise either from biological or technological sources. For instance, some genes were represented on the microarray by more than one probe, and there were several pairs of probes in the IRG subcluster area that represent the same gene's expression. In these cases, the probes clustered near to each other, sometimes immediately adjacent. Thus it appeared that a clear pattern was present and reflected in many probes, and that utilizing the data from several probes in order to mitigate the interference of noise in the data might most clearly identify the pattern. Nonetheless, the genes that were identified could be used individually as genetic identifiers that correlate with presence of disease.

Figure 4:
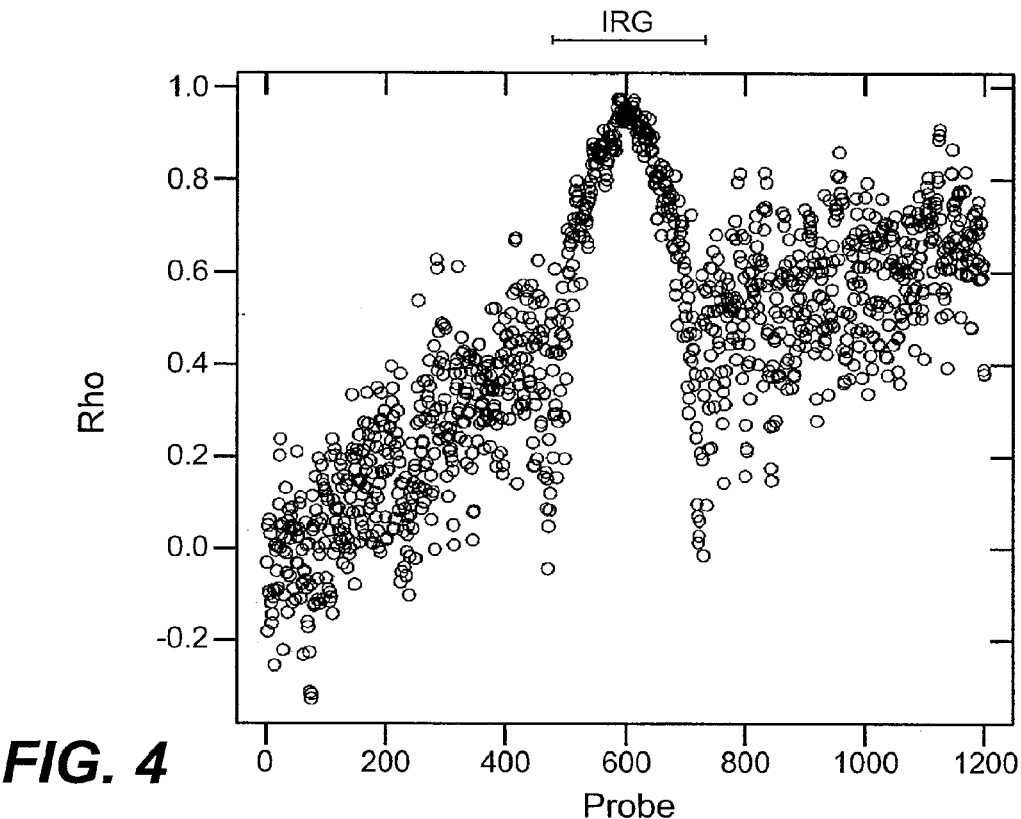
FIG. 4. Rho values of Spearman correlation of probes to the IRG signature reveal the extent of the region containing IRG signal.

A relatively complete set of genes whose expression is indicative of a response to type 1 interferons (IRG) was identified. The IRG region, identified as a tightly clustered region of the clustered data containing 80 microarray probes highly enriched in known IRG's, was used as the definition of an interferon response profile by averaging the clustered data in this slice of 80 probes. The averaging was performed by taking the arithmetic mean across the 80 probes to yield a vector of length 118 that described the average relative interferon response in the 118 samples analyzed. The similarity of each probe in the cluster data was then compared to this signature vector by computing the Spearman correlation rho value of each pairwise comparison. Visual inspection of these rho values for probes in their clustered order showed an obvious maximum at the center of the IRG cluster (FIG. 4), and it also revealed clear boundaries between the region of locally elevated correlation and the adjacent regions that were less correlated and were influenced much more heavily by other signals and noise. The probes in this complete IRG region are listed in Table 2. Table 3 shows probes (in some cases, multiple probes) corresponding to a subset of novel genes from Table 2.

All probes in this set and their corresponding genes are useful markers for the level of response of blood cells to type I interferons. They are informative of the response individually or when combined in any number and combination as previously described to create an interferon signature metric (ISM). The measurement of their expression level for this purpose could be accomplished effectively using any of a variety of standard techniques, e.g., expression microarrays (e.g. commercially available arrays such as Affymetrix HGU133), or real-time PCR (e.g. Taqman).

TABLE 2

201 microarray probes constituting a set of type-I interferon responsive genes, their Spearman (rho) correlation to the interferon signature, Refseq or Genbank accession number, symbol, and name.

| Probe | Rho | Accession | Symbol | Name |
| --- | --- | --- | --- | --- |
| 226603_at | 0.9760 | NM_152703 | SAMD9L | sterile alpha motif domain containing 9-like |
| 230036_at | 0.9754 | NM_152703 | SAMD9L | sterile alpha motif domain containing 9-like |
| 226702_at | 0.9747 | NM_207315 | TYKI | Thymidylate kinase family LPS-inducible |
| 242625_at | 0.9733 | NM_080657 | RSAD2 (CIG5) | radical S-adenosyl methionine domain containing 2 |
| 223220_s_at | 0.9725 | NM_031458 | PARP9 | poly ADP-ribose polymerase family, member 9 |
| 213797_at | 0.9679 | NM_080657 | RSAD2 (CIG5) | radical S-adenosyl methionine domain containing 2 |
| 204747_at | 0.9664 | NM_001031683 | IFIT3 | interferon-induced protein with tetratricopeptide repeats 3 |
| 203153_at | 0.9586 | NM_001001887 | IFIT1 | interferon-induced protein with tetratricopeptide repeats 1 |
| 226757_at | 0.9582 | NM_001547 | IFIT2 | interferon-induced protein with tetratricopeptide repeats 2 |
| 229450_at | 0.9572 | NM_001031683 | IFIT3 | interferon-induced protein with tetratricopeptide repeats 3 |
| 208436_s_at | 0.9568 | NM_001572 | IRF7 | interferon regulatory factor 7 |
| 219062_s_at | 0.9544 | NM_017742 | ZCCHC2 | zinc finger, CCHC domain containing 2 |
| 224701_at | 0.9531 | NM_017554 | PARP14 | poly ADP-ribose polymerase family, member 14 |
| 205483_s_at | 0.9511 | NM_005101 | G1P2 | interferon, alpha-inducible protein clone IFI-15K |
| 218943_s_at | 0.9495 | NM_014314 | DDX58 (RIG1) | DEAD Asp-Glu-Ala-Asp box polypeptide 58 |
| 219863_at | 0.9462 | NM_016323 | HERC5 | hect domain and RLD 5 |
| 227609_at | 0.9458 | NM_001002264 | EPSTI1 | epithelial stromal interaction 1 breast |
| 219356_s_at | 0.9456 | NM_016410 | CHMP5 | chromatin modifying protein 5 |
| 203596_s_at | 0.9456 | NM_012420 | IFIT5 | interferon-induced protein with tetratricopeptide repeats 5 |
| 228152_s_at | 0.9422 | XM_037817 | LCGE22799 | FLJ31033 |
| 228531_at | 0.9417 | NM_017654 | SAMD9 | sterile alpha motif domain containing 9 |
| 203595_s_at | 0.9406 | NM_012420 | IFIT5 | interferon-induced protein with tetratricopeptide repeats 5 |
| 202446_s_at | 0.9383 | NM_021105 | PLSCR2 | phospholipid scramblase 2 |
| 228617_at | 0.9379 | NM_017523 | HSXIAPAF1 | XIAP associated factor-1 |
| 232222_at | 0.9374 | NM_017742 | ZCCHC2 | zinc finger, CCHC domain containing 2 |
| 204439_at | 0.9356 | NM_006820 | IFI44L | interferon-induced protein 44-like |
| 212657_s_at | 0.9346 | NM_000577 | IL1RN | interleukin 1 receptor antagonist |
| 210797_s_at | 0.9341 | NM_003733 | OASL | 2'-5'-oligoadenylate synthetase-like |
| 213294_at | 0.9334 | P_ADB12769 | PRKR | dsRNA-dependent protein kinase |
| 211012_s_at | 0.9311 | NM_002675 | PML | promyelocytic leukemia |
| 202086_at | 0.9302 | NM_002462 | MX1 | myxovirus influenza virus resistance 1 |
| 223502_s_at | 0.9300 | NM_006573 | TNFSF13B | tumor necrosis factor ligand superfamily, member 13b |
| 227807_at | 0.9295 | NM_031458 | PARP9 | poly ADP-ribose polymerase family, member 9 |
| 214453_s_at | 0.9278 | NM_006417 | IFI44 | interferon-induced protein 44 |
| 205660_at | 0.9275 | NM_003733 | OASL | 2'-5'-oligoadenylate synthetase-like |
| 228230_at | 0.9273 | NM_033405 | PRIC285 | peroxisomal proliferator-activated receptor A |

TABLE 2-continued 201 microarray probes constituting a set of type-I interferon responsive genes, their Spearman (rho) correlation to the interferon signature, Refseq or Genbank accession number, symbol, and name.

| Probe | Rho | Accession | Symbol | Name |
|---|---|---|---|---|
| 218400_at | 0.9253 | NM_006187 | OAS3 | 2'-5'-oligoadenylate synthetase 3 |
| 223501_at | 0.9227 | NM_006573 | TNFSF13B | tumor necrosis factor ligand superfamily, member 13b |
| 214059_at | 0.9186 | NM_006417 | IFI44 | interferon-induced protein 44 |
| 202687_s_at | 0.9178 | NM_003810 | Apo-2L | Apo-2 Ligand |
| 202863_at | 0.9176 | NM_003113 | SP140 | SP140 nuclear body protein |
| 217502_at | 0.9158 | NM_001547 | IFIT2 | interferon-induced protein with tetratricopeptide repeats 2 |
| 218085_at | 0.9130 | NM_016410 | CHMP5 | chromatin modifying protein 5 |
| 228439_at | 0.9123 | NM_138456 | BATF2 | basic leucine zipper transcription factor, ATF-like 2 |
| 209593_s_at | 0.9089 | NM_014506 | TOR1B | torsin family 1, member B torsin B |
| 222793_at | 0.9079 | NM_014314 | DDX58 (RIG1) | DEAD Asp-Glu-Ala-Asp box polypeptide 58 |
| 204994_at | 0.9061 | NM_002463 | MX2 | myxovirus influenza virus resistance 2 mouse |
| 219691_at | 0.9029 | NM_017654 | SAMD9 | sterile alpha motif domain containing 9 |
| 208087_s_at | 0.9027 | NM_030776 | ZBP1 | Z-D binding protein 1 |
| 202270_at | 0.9008 | NM_002053 | GBP1 | guanylate binding protein 1, interferon-inducible, 67 kDa |
| 231577_s_at | 0.9007 | NM_002053 | GBP1 | guanylate binding protein 1, interferon-inducible, 67 kDa |
| 219209_at | 0.9004 | NM_022168 | IFIH1 | interferon induced with helicase C domain 1 |
| 200986_at | 0.8978 | NM_000062 | SERPING1 | Serine/cysteine proteinase inhibitor, clade G C1 inhibitor, 1 |
| 204972_at | 0.8964 | NM_001032731 | OAS2 | 2'-5'-oligoadenylate synthetase 2, 69/71 kDa |
| 242020_s_at | 0.8948 | NM_030776 | ZBP1 | Z-D binding protein 1 |
| 209498_at | 0.8933 | NM_001024912 | CEACAM1 | carcinoembryonic antigen-related cell adhesion molecule 1 |
| 235276_at | 0.8931 | NM_001002264 | EPSTI1 | epithelial stromal interaction 1 breast |
| 219211_at | 0.8925 | NM_017414 | USP18 | ubiquitin specific protease 41 |
| 239277_at | 0.8897 | NM_001033583 | ACOT9 | acyl-CoA thioesterase 9 |
| 243271_at | 0.8892 | NM_152703 | SAMD9L | sterile alpha motif domain containing 9-like |
| 205098_at | 0.8887 | NM_001295 | CCR1 | chemokine C-C motif receptor 1 |
| 202430_s_at | 0.8859 | NM_021105 | PLSCR2 | phospholipid scramblase 2 |
| 209417_s_at | 0.8837 | NM_005533 | IFI35 | interferon-induced protein 35 |
| 205552_s_at | 0.8789 | NM_001032409 | OAS1 | 2',5'-oligoadenylate synthetase 1, 40/46 kDa |
| 231769_at | 0.8783 | NM_018438 | FBXO6 | F-box protein 6 |
| 241916_at | 0.8782 | NM_021105 | PLSCR2 | phospholipid scramblase 2 |
| 233425_at | 0.8778 | NM_017742 | ZCCHC2 | zinc finger, CCHC domain containing 2 |
| 218543_s_at | 0.8762 | NM_022750 | PARP12 | poly ADP-ribose polymerase family, member 12 |
| 202307_s_at | 0.8742 | NM_000593 | TAP1 | transporter 1, ATP-binding cassette, sub-family B |
| 204698_at | 0.8735 | NM_002201 | ISG20 | interferon stimulated gene 20 kDa |
| 202269_x_at | 0.8730 | NM_002053 | GBP1 | guanylate binding protein 1, interferon-inducible, 67 kDa |
| 232666_at | 0.8711 | NM_006187 | OAS3 | 2'-5'-oligoadenylate synthetase 3, 100 kDa |
| 218986_s_at | 0.8703 | NM_017631 | SGRA12061 | Hypothetical protein FLJ20035 FLJ20035 |
| 205569_at | 0.8675 | NM_014398 | LAMP3 | lysosomal-associated membrane protein 3 |
| 202145_at | 0.8672 | NM_002346 | LY6E (RIGE) | lymphocyte antigen 6 complex, locus E |
| 219352_at | 0.8671 | NM_001013000 | HERC6 | hect domain and RLD 6 |
| 239979_at | 0.8665 | NM_001002264 | EPSTI1 | epithelial stromal interaction 1 breast |
| 223599_at | 0.8664 | NM_001003818 | TRIMP1 | tripartite motif-containing pseudogene 1 |
| 230866_at | 0.8656 | NM_006639 | CYSLTR1 | cysteinyl leukotriene receptor 1 |
| 216565_x_at | 0.8650 | XM_497663 | LOC391020 | similar to Interferon-induced transmembrane protein 3 |
| 212659_s_at | 0.8635 | NM_000577 | IL1RN | interleukin 1 receptor antagonist |
| 202869_at | 0.8634 | NM_001032409 | OAS1 | 2',5'-oligoadenylate synthetase 1, 40/46 kDa |
| 223952_x_at | 0.8623 | NM_005771 | DHRS9 | dehydrogenase/reductase SDR family member 9 |
| 205241_at | 0.8614 | NM_001953 | SCO2 | SCO cytochrome oxidase deficient homolog 2 yeast |
| 227458_at | 0.8601 | NM_014143 | PDL1/B7-H1 | programmed cell death 1 ligand 1 |
| 231747_at | 0.8600 | NM_006639 | CYSLTR1 | cysteinyl leukotriene receptor 1 |
| 209969_s_at | 0.8576 | NM_007315 | STAT1 | signal transducer and activator of transcription 1, 91 kDa |
| 218999_at | 0.8561 | NM_018295 | AGPR4538 | hypothetical protein MGC5242 |
| 224009_x_at | 0.8535 | NM_005771 | DHRS9 | dehydrogenase/reductase SDR family member 9 |

TABLE 2-continued 201 microarray probes constituting a set of type-I interferon responsive genes, their Spearman (rho) correlation to the interferon signature, Refseq or Genbank accession number, symbol, and name.

| Probe | Rho | Accession | Symbol | Name |
|---|---|---|---|---|
| 228607_at | 0.8529 | NM_001032731 | OAS2 | 2'-5'-oligoadenylate synthetase 2, 69/71 kDa |
| 205099_s_at | 0.8516 | NM_001295 | CCR1 | chemokine C-C motif receptor 1 |
| 219799_s_at | 0.8479 | NM_005771 | DHRS9 | dehydrogenase/reductase SDR family member 9 |
| 206133_at | 0.8420 | NM_017523 | HSXIAPAF1 | XIAP associated factor-1 |
| 211889_x_at | 0.8386 | NM_001024912 | CEACAM1 | carcinoembryonic antigen-related cell adhesion molecule 1 |
| 222154_s_at | 0.8365 | NM_015535 | DNAPTP6 | DNA polymerase-transactivated protein 6 |
| 225291_at | 0.8350 | NM_033109 | PNPT1 | polyribonucleotide nucleotidyltransferase 1 |
| 202864_s_at | 0.8347 | NM_003113 | SP140 | SP140 nuclear body protein |
| 210705_s_at | 0.8341 | NM_033034 | TRIM5 | tripartite motif-containing 5 |
| 223167_s_at | 0.8334 | NM_013396 | USP25 | ubiquitin specific protease 25 |
| 229625_at | 0.8324 | NM_004120 | GBP5 | guanylate binding protein 5 |
| 202837_at | 0.8278 | NM_006700 | TRAFD1 | TRAF-type zinc finger domain containing 1 |
| 216243_s_at | 0.8185 | NM_000577 | IL1RN | interleukin 1 receptor antagonist |
| 223849_s_at | 0.8180 | NM_020963 | MOV10 | Mov10, Moloney leukemia virus 10, homolog mouse |
| 222498_at | 0.8175 | NM_022461 | AZI2 | 5-azacytidine induced 2 |
| 238581_at | 0.8173 | NM_004120 | GBP5 | guanylate binding protein 5 |
| 217933_s_at | 0.8138 | NM_015907 | LAP3 | leucine aminopeptidase 3 |
| 219519_s_at | 0.8108 | NM_023068 | SIGLEC1 | sialoadhesin |
| 208392_x_at | 0.8084 | NM_004509 | SP110 | SP110 nuclear body protein |
| 239988_at | 0.8079 | NM_017912 | SKKS30637 | Hect domain and RLD 6 |
| 230314_at | 0.8074 | P_ADH28842 | CMLM110 | chronic myelogenous leukaemia (CML) gene marker #110 |
| 206576_s_at | 0.8072 | NM_001024912 | CEACAM1 | carcinoembryonic antigen-related cell adhesion molecule 1 |
| 227347_x_at | 0.8047 | NM_021170 | HES4 | hairy and enhancer of split 4 Drosophila |
| 202411_at | 0.8038 | NM_005532 | IFI27 | interferon, alpha-inducible protein 27 |
| 219684_at | 0.7998 | NM_022147 | TMEM7 | transmembrane protein 7 |
| 205003_at | 0.7974 | NM_014705 | DOCK4 | dedicator of cytokinesis 4 |
| 212185_x_at | 0.7969 | NM_005953 | MT2A | metallothionein 2A |
| 235256_s_at | 0.7957 | NM_138801 | GALM | galactose mutarotase aldose 1-epimerase |
| 242234_at | 0.7948 | NM_017523 | HSXIAPAF1 | XIAP associated factor-1 |
| 211883_x_at | 0.7916 | NM_001024912 | CEACAM1 | carcinoembryonic antigen-related cell adhesion molecule 1 |
| 206513_at | 0.7891 | NM_004833 | AIM2 | absent in melanoma 2 |
| 44673_at | 0.7884 | NM_023068 | SIGLEC1 | sialoadhesin |
| 209546_s_at | 0.7869 | NM_003661 | APOL1 | apolipoprotein L, 1 |
| 204415_at | 0.7838 | NM_002038 | G1P3 | interferon, alpha-inducible protein clone IFI-6-16 |
| 206553_at | 0.7821 | NM_001032731 | OAS2 | 2'-5'-oligoadenylate synthetase 2, 69/71 kDa |
| 206461_x_at | 0.7758 | NM_005946 | MT2A | metallothionein 2A |
| 226169_at | 0.7746 | NM_030962 | SBF2 | SET binding factor 2 |
| 244398_x_at | 0.7742 | NM_152373 | ZNF684 | zinc finger protein 684 |
| 238439_at | 0.7659 | NM_144590 | ANKRD22 | ankyrin repeat domain 22 |
| 227649_s_at | 0.7646 | NM_015326 | SRGAP2 | SLIT-ROBO Rho GTPase activating protein 2 |
| 220998_s_at | 0.7644 | NM_030930 | UNC93B1 | unc-93 homolog B1 C. elegans |
| 204211_x_at | 0.7628 | NM_002759 | EIF2AK2 | eukaryotic translation initiation factor 2-alpha kinase 2 |
| 224973_at | 0.7612 | NM_017633 | FAM46A | family with sequence similarity 46, member A |
| 234974_at | 0.7601 | NM_138801 | GALM | galactose mutarotase aldose 1-epimerase |
| 242898_at | 0.7588 | NM_002759 | EIF2AK2 | eukaryotic translation initiation factor 2-alpha kinase 2 |
| 232034_at | 0.7581 | BC080605 | LOC203274 | hypothetical protein LOC203274 |
| 231455_at | 0.7560 | NM_001001695 | FLJ42418 | FLJ42418 |
| 208581_x_at | 0.7546 | NM_005952 | MT1X | metallothionein 1X |
| 224225_s_at | 0.7545 | NM_016135 | ETV7 | ets variant gene 7 (TEL2 oncogene) |
| 205875_s_at | 0.7543 | NM_016381 | TREX1 | three prime repair exonuclease 1 |
| 209286_at | 0.7522 | NM_006449 | CDC42EP3 | CDC42 effector protein Rho GTPase binding 3 |
| 205715_at | 0.7472 | NM_004334 | BST1 | bone marrow stromal cell antigen 1 |
| 223834_at | 0.7465 | NM_014143 | PDL1/B7-H1 | programmed cell death 1 ligand 1 |
| 212285_s_at | 0.7414 | NM_198576 | AGRN | agrin |
| 230695_s_at | 0.7381 | NM_152732 | C6orf206 | chromosome 6 open reading frame 206 |
| 219364_at | 0.7381 | NM_024119 | LGP2 | likely ortholog of mouse D11lgp2 |
| 238455_at | 0.7371 | NM_032812 | PLXDC2 | Plexin domain containing 2 |
| 201641_at | 0.7343 | NM_004335 | BST2 | Bone marrow stromal antigen 2 |

TABLE 2-continued 201 microarray probes constituting a set of type-I interferon responsive genes, their Spearman (rho) correlation to the interferon signature, Refseq or Genbank accession number, symbol, and name.

| Probe | Rho | Accession | Symbol | Name |
|---|---|---|---|---|
| 219439_at | 0.7273 | NM_020156 | C1GALT1 | core 1 synthase, glyc-N-acetylgal 3-beta-galtransferase, 1 |
| 224503_s_at | 0.7231 | NM_017742 | ZCCHC2 | zinc finger, CCHC domain containing 2 |
| 234942_s_at | 0.7226 | NM_052951 | DNTTIP1 | deoxynucleotidyltransferase, terminal, interacting protein 1 |
| 214933_at | 0.7212 | NM_000068 | CAC1A | calcium channel, voltage-dependent, P/Q type, alpha 1A |
| 219055_at | 0.7189 | NM_018079 | SRBD1 | S1 RNA binding domain 1 |
| 225447_at | 0.7179 | NM_000408 | GPD2 | glycerol-3-phosphate dehydrogenase 2 mitochondrial |
| 236285_at | 0.7173 | P_AAF17573 | SYN22A2 | Breast cancer associated SYN22A2 coding sequence |
| 217165_x_at | 0.7168 | NM_005946 | MT2A | metallothionein 2A |
| 200923_at | 0.7164 | NM_005567 | LGALS3BP | lectin, galactoside-binding, soluble, 3 binding protein |
| 220104_at | 0.7159 | NM_020119 | ZC3HAV1 | zinc finger CCCH-type, antiviral 1 |
| 216950_s_at | 0.7133 | NM_000566 | FCGR1A | Fc fragment of IgG, high affinity Ia, receptor CD64 |
| 227905_s_at | 0.7115 | NM_022461 | AZI2 | 5-azacytidine induced 2 |
| 230997_at | 0.7109 | NM_145755 | TTC21A | tetratricopeptide repeat domain 21A |
| 210889_s_at | 0.7099 | NM_001002273 | FCGR2B | Low affinity immunoglobulin gamma fc receptor ii-b |
| 214511_x_at | 0.7050 | NM_000566 | FCGR1A | Fc fragment of IgG, high affinity Ia, receptor (CD64) |
| 211456_x_at | 0.7045 | NM_001039954 | MT1P2 | metallothionein 1 pseudogene 2 |
| 232563_at | 0.7017 | NM_152373 | ZNF684 | zinc finger protein 684 |
| 235456_at | 0.6926 | NM_021063 | HIST1H2BD | histone 1, H2bd |
| 229194_at | 0.6917 | NM_032373 | PCGF5 | polycomb group ring finger 5 |
| 235157_at | 0.6859 | NM_017554 | PARP14 | poly ADP-ribose polymerase family, member 14 |
| 230333_at | 0.6851 | NM_002970 | SAT | Spermidine/spermine N1-acetyltransferase |
| 231956_at | 0.6813 | NM_020954 | KIAA1618 | KIAA1618 |
| 235175_at | 0.6803 | NM_052941 | GBP4 | guanylate binding protein 4 |
| 232149_s_at | 0.6777 | NM_003580 | NSMAF | neutral sphingomyelinase N-SMase activation assoc factor |
| 235331_x_at | 0.6769 | NM_032373 | PCGF5 | polycomb group ring finger 5 |
| 221653_x_at | 0.6762 | NM_030882 | APOL2 | apolipoprotein L, 2 |
| 219716_at | 0.6689 | NM_030641 | APOL6 | apolipoprotein L, 6 |
| 214909_s_at | 0.6669 | NM_013974 | DDAH2 | dimethylarginine dimethylaminohydrolase 2 |
| 207500_at | 0.6654 | NM_004347 | CASP5 | caspase 5, apoptosis-related cysteine protease |
| 232081_at | 0.6648 | NM_004915 | ABCG1 | ATP-binding cassette, sub-family G WHITE, member 1 |
| 241812_at | 0.6584 | NM_015535 | DNAPTP6 | DNA polymerase-transactivated protein 6 |
| 230166_at | 0.6571 | NM_133465 | KIAA1958 | KIAA1958 |
| 239143_x_at | 0.6554 | NM_016271 | RNF138 | ring finger protein 138 |
| 217823_s_at | 0.6543 | NM_016021 | UBE2J1 | ubiquitin-conjugating enzyme E2, J1 UBC6 homolog, yeast |
| 242109_at | 0.6501 | NM_006519 | TCTEL1 | t-complex-associated-testis-expressed 1-like 1 |
| 206175_x_at | 0.6420 | NM_013360 | ZNF230 | zinc finger protein 230 |
| 215537_x_at | 0.6366 | NM_013974 | DDAH2 | dimethylarginine dimethylaminohydrolase 2 |
| 220252_x_at | 0.6318 | NM_025159 | CXorf21 | chromosome X open reading frame 21 |
| 227268_at | 0.6213 | NM_016125 | PLFL4625 | PTD016 protein |
| 216336_x_at | 0.6153 | NM_153341 | IBRDC3 | IBR domain containing 3 |
| 229804_x_at | 0.6077 | NM_018491 | CBWD1 | COBW domain containing 1 |
| 236013_at | 0.6011 | NM_000721 | CAC1E | calcium channel, voltage-dependent, alpha 1E subunit |
| 227004_at | 0.5968 | NM_003159 | CDKL5 | cyclin-dependent kinase-like 5 |
| 226099_at | 0.5788 | NM_012081 | ELL2 | elongation factor, R polymerase II, 2 |
| 227947_at | 0.5761 | NM_014721 | PHACTR2 | phosphatase and actin regulator 2 |
| 210985_s_at | 0.5722 | NM_003113 | SP140 | SP140 nuclear body protein |
| 204326_x_at | 0.5699 | NM_005952 | MT1X | metallothionein 1X |
| 233264_at | 0.5515 | AK022088 | FLJ12026 | HEMBB1001816 |
| 212859_x_at | 0.5285 | NM_005953 | MT1X | metallothionein 1X |
| 235348_at | 0.5251 | NM_032859 | C13orf6 | chromosome 13 open reading frame 6 |
| 225872_at | 0.5053 | NM_025181 | SLC35F5 | solute carrier family 35, member F5 |
| 235681_at | 0.4913 | NM_021063 | HIST1H2BD | histone 1, H2bd |
| 207291_at | 0.4851 | NM_024081 | PRRG4 | proline rich Gla G-carboxyglutamic acid 4 transmembrane |

TABLE 2-continued 201 microarray probes constituting a set of type-I interferon responsive genes, their Spearman (rho) correlation to the interferon signature, Refseq or Genbank accession number, symbol, and name.

| Probe | Rho | Accession | Symbol | Name |
|---|---|---|---|---|
| 234997_x_at | 0.4617 | CD684982 | EST1502 | human spermidine/spermine N1 acetyl transferase |

TABLE 3

Selected subset of novel probesets/genes from Table 2. Where appropriate, multiple probesets (with their respective rho values) are listed with their respective corresponding gene.

| Probe | Rho | Accession | Symbol | Name |
|---|---|---|---|---|
| 228152_s_at | 0.9422 | XM_037817 | LCGE22799 | FLJ31033 |
| 202446_s_at; 202430_s_at; 241916_at | 0.9383; 0.8859; 0.8782 | NM_021105 | PLSCR2 | phospholipid scramblase 2 |
| 213294_at | 0.9334 | P_ADB12769 | PRKR | dsRNA-dependent protein kinase |
| 211012_s_at | 0.9311 | NM_002675 | PML | promyelocytic leukemia |
| 228230_at | 0.9273 | NM_033405 | PRIC285 | peroxisomal proliferator-activated receptor A |
| 202687_s_at | 0.9178 | NM_003810 | Apo-2L | Apo-2 Ligand |
| 202863_at; 202864_s_at; 210985_s_at | 0.9176; 0.8347; 0.5722 | NM_003113 | SP140 | SP140 nuclear body protein |
| 209498_at; 211889_x_at; 206576_s_at; 211883_x_at | 0.8933; 0.8386; 0.8072; 0.7916 | NM_001024912 | CEACAM1 | carcinoembryonic antigen-related cell adhesion molecule 1 |
| 239277_at | 0.8897 | NM_001033583 | ACOT9 | acyl-CoA thioesterase 9 |
| 231769_at | 0.8783 | NM_018438 | FBXO6 | F-box protein 6 |
| 202307_s_at | 0.8742 | NM_000593 | TAP1 | transporter 1, ATP-binding cassette, sub-family B |
| 204698_at | 0.8735 | NM_002201 | ISG20 | interferon stimulated gene 20 kDa |
| 218986_s_at | 0.8703 | NM_017631 | SGRA12061 | Hypothetical protein FLJ20035 FLJ20035 |
| 205569_at | 0.8675 | NM_014398 | LAMP3 | lysosomal-associated membrane protein 3 |
| 223599_at | 0.8664 | NM_001003818 | TRIMP1 | tripartite motif-containing pseudogene 1 |
| 230866_at; 231747_at | 0.8656; 0.8600 | NM_006639 | CYSLTR1 | cysteinyl leukotriene receptor 1 |
| 216565_x_at | 0.8650 | XM_497663 | LOC391020 | similar to Interferon-induced transmembrane protein 3 |
| 223952_x_at; 224009_x_at; 219799_s_at | 0.8623; 0.8535; 0.8479 | NM_005771 | DHRS9 | dehydrogenase/reductase SDR family member 9 |
| 205241_at | 0.8614 | NM_001953 | SCO2 | SCO cytochrome oxidase deficient homolog 2 yeast |
| 227458_at; 223834_at | 0.8601; 0.7465 | NM_014143 | PDL1/B7-H1 | programmed cell death 1 ligand 1 |
| 209969_s_at | 0.8576 | NM_007315 | STAT1 | signal transducer and activator of transcription 1, 91 kDa |
| 218999_at | 0.8561 | NM_018295 | AGPR4538 | hypothetical protein MGC5242 |
| 210705_s_at | 0.8341 | NM_033034 | TRIM5 | tripartite motif-containing 5 |
| 223167_s_at | 0.8334 | NM_013396 | USP25 | ubiquitin specific protease 25 |
| 229625_at; 238581_at | 0.8324; 0.8173 | NM_004120 | GBP5 | guanylate binding protein 5 |
| 202837_at | 0.8278 | NM_006700 | TRAFD1 | TRAF-type zinc finger domain containing 1 |
| 223849_s_at | 0.8180 | NM_020963 | MOV10 | Mov10, Moloney leukemia virus 10, homolog mouse |
| 222498_at; 227905_s_at | 0.8175; 0.7115 | NM_022461 | AZI2 | 5-azacytidine induced 2 |
| 217933_s_at | 0.8138 | NM_015907 | LAP3 | leucine aminopeptidase 3 |
| 219519_s_at; 44673_at | 0.8108; 0.7884 | NM_023068 | SIGLEC1 | sialoadhesin |
| 208392_x_at | 0.8084 | NM_004509 | SP110 | SP110 nuclear body protein |
| 239988_at | 0.8079 | NM_017912 | SKKS30637 | Hect domain and RLD 6 |
| 230314_at | 0.8074 | P_ADH28842 | CMLM110 | chronic myclogenous leukaemia (CML) gene marker #110 |
| 227347_x_at | 0.8047 | NM_021170 | HES4 | hairy and enhancer of split 4 Drosophila |

TABLE 3-continued

Selected subset of novel probesets/genes from Table 2. Where appropriate, multiple probesets (with their respective rho values) are listed with their respective corresponding gene.

| Probe | Rho | Accession | Symbol | Name |
|---|---|---|---|---|
| 202411_at | 0.8038 | NM_005532 | IFI27 | interferon, alpha-inducible protein 27 |
| 205003_at | 0.7974 | NM_014705 | DOCK4 | dedicator of cytokinesis 4 |
| 212185_x_at; 206461_x_at; 217165_x_at | 0.7969; 0.7758; 0.7168 | NM_005953 | MT2A | metallothionein 2A |
| 235256_s_at; 234974_at | 0.7957; 0.7601 | NM_138801 | GALM | galactose mutarotase aldose 1-epimerase |
| 206513_at | 0.7891 | NM_004833 | AIM2 | absent in melanoma 2 |
| 209546_s_at | 0.7869 | NM_003661 | APOL1 | apolipoprotein L, 1 |
| 204415_at | 0.7838 | NM_002038 | G1P3 | interferon, alpha-inducible protein clone IFI-6-16 |
| 206553_at | 0.7821 | NM_001032731 | OAS2 | 2'-5'-oligoadenylate synthetase 2, 69/71 kDa |
| 226169_at | 0.7746 | NM_030962 | SBF2 | SET binding factor 2 |
| 244398_x_at; 232563_at | 0.7742; 0.7017 | NM_152373 | ZNF684 | zinc finger protein 684 |
| 238439_at | 0.7659 | NM_144590 | ANKRD22 | ankyrin repeat domain 22 |
| 227649_s_at | 0.7646 | NM_015326 | SRGAP2 | SLIT-ROBO Rho GTPase activating protein 2 |
| 220998_s_at | 0.7644 | NM_030930 | UNC93B1 | unc-93 homolog B1 C. elegans |
| 224973_at | 0.7612 | NM_017633 | FAM46A | family with sequence similarity 46, member A |
| 232034_at | 0.7581 | | LOC203274 | |
| 231455_at | 0.7560 | NM_001001695 | FLJ42418 | FLJ42418 |
| 208581_x_at; 204326_x_at; 212859_x_at | 0.7546; 0.5699; 0.5285 | NM_005952 | MT1X | metallothionein 1X |
| 224225_s_at | 0.7545 | NM_016135 | ETV7 | ets variant gene 7 (TEL2 oncogene) |
| 205875_s_at | 0.7543 | NM_016381 | TREX1 | three prime repair exonuclease 1 |
| 209286_at | 0.7522 | NM_006449 | CDC42EP3 | CDC42 effector protein Rho GTPase binding 3 |
| 205715_at | 0.7472 | NM_004334 | BST1 | bone marrow stromal cell antigen 1 |
| 212285_s_at | 0.7414 | NM_198576 | AGRN | agrin |
| 230695_s_at | 0.7381 | NM_152732 | C6orf206 | chromosome 6 open reading frame 206 |
| 219364_at | 0.7381 | NM_024119 | LGP2 | likely ortholog of mouse D11lgp2 |
| 238455_at | 0.7371 | NM_032812 | PLXDC2 | Plexin domain containing 2 |
| 201641_at | 0.7343 | NM_004335 | BST2 | Bone marrow stromal antigen 2 |
| 219439_at | 0.7273 | NM_020156 | C1GALT1 | core 1 synthase, glyc-N-acetylgal 3-beta-galtransferase, 1 |
| 234942_s_at | 0.7226 | NM_052951 | DNTTIP1 | deoxynucleotidyltransferase, terminal, interacting protein 1 |
| 214933_at | 0.7212 | NM_000068 | CAC1A | calcium channel, voltage-dependent, P/Q type, alpha 1A |
| 219055_at | 0.7189 | NM_018079 | SRBD1 | S1 RNA binding domain 1 |
| 225447_at | 0.7179 | NM_000408 | GPD2 | glycerol-3-phosphate dehydrogenase 2 mitochondrial |
| 236285_at | 0.7173 | P_AAF17573 | SYN22A2 | Breast cancer associated SYN22A2 coding sequence |
| 200923_at | 0.7164 | NM_005567 | LGALS3BP | lectin, galactoside-binding, soluble, 3 binding protein |
| 220104_at | 0.7159 | NM_020119 | ZC3HAV1 | zinc finger CCCH-type, antiviral 1 |
| 216950_s_at; 214511_x_at | 0.7133; 0.7050 | NM_000566 | FCGR1A | Fc fragment of IgG, high affinity Ia, receptor CD64 |
| 230997_at | 0.7109 | NM_145755 | TTC21A | tetratricopeptide repeat domain 21A |
| 210889_s_at | 0.7099 | NM_001002273 | FCGR2B | Low affinity immunoglobulin gamma fc receptor ii-b |
| 211456_x_at | 0.7045 | NM_001039954 | MT1P2 | metallothionein 1 pseudogene 2 |
| 235456_at; 235681_at | 0.6926; 0.4913 | NM_021063 | HIST1H2BD | histone 1, H2bd |
| 229194_at; 235331_x_at | 0.6917; 0.6769 | NM_032373 | PCGF5 | polycomb group ring finger 5 |
| 230333_at | 0.6851 | NM_002970 | SAT | Spermidine/spermine N1-acetyltransferase |
| 231956_at | 0.6813 | NM_020954 | KIAA1618 | KIAA1618 |
| 235175_at | 0.6803 | NM_052941 | GBP4 | guanylate binding protein 4 |
| 232149_s_at | 0.6777 | NM_003580 | NSMAF | neutral sphingomyelinase N-SMase activation assoc factor |
| 221653_x_at | 0.6762 | NM_030882 | APOL2 | apolipoprotein L, 2 |
| 219716_at | 0.6689 | NM_030641 | APOL6 | apolipoprotein L, 6 |

TABLE 3-continued

Selected subset of novel probesets/genes from Table 2. Where appropriate, multiple probesets (with their respective rho values) are listed with their respective corresponding gene.

| Probe | Rho | Accession | Symbol | Name |
|---|---|---|---|---|
| 214909_s_at; | 0.6669; | NM_013974 | DDAH2 | dimethylarginine dimethylaminohydrolase 2 |
| 215537_x_at | 0.6366 | | | |
| 207500_at | 0.6654 | NM_004347 | CASP5 | caspase 5, apoptosis-related cysteine protease |
| 232081_at | 0.6648 | NM_004915 | ABCG1 | ATP-binding cassette, sub-family G WHITE, member 1 |
| 230166_at | 0.6571 | NM_133465 | KIAA1958 | KIAA1958 |
| 239143_x_at | 0.6554 | NM_016271 | RNF138 | ring finger protein 138 |
| 217823_s_at | 0.6543 | NM_016021 | UBE2J1 | ubiquitin-conjugating enzyme E2, J1 UBC6 homolog, yeast |
| 242109_at | 0.6501 | NM_006519 | TCTEL1 | t-complex-associated-testis-expressed 1-like 1 |
| 206175_x_at | 0.6420 | NM_013360 | ZNF230 | zinc finger protein 230 |
| 220252_x_at | 0.6318 | NM_025159 | CXorf21 | chromosome X open reading frame 21 |
| 227268_at | 0.6213 | NM_016125 | PLFL4625 | PTD016 protein |
| 216336_x_at | 0.6153 | NM_153341 | IBRDC3 | IBR domain containing 3 |
| 229804_x_at | 0.6077 | NM_018491 | CBWD1 | COBW domain containing 1 |
| 236013_at | 0.6011 | NM_000721 | CAC1E | calcium channel, voltage-dependent, alpha 1E subunit |
| 227004_at | 0.5968 | NM_003159 | CDKL5 | cyclin-dependent kinase-like 5 |
| 226099_at | 0.5788 | NM_012081 | ELL2 | elongation factor, R polymerase II, 2 |
| 227947_at | 0.5761 | NM_014721 | PHACTR2 | phosphatase and actin regulator 2 |
| 233264_at | 0.5515 | AK022088 | FLJ12026 | HEMBB1001816 |
| 235348_at | 0.5251 | NM_032859 | C13orf6 | chromosome 13 open reading frame 6 |
| 225872_at | 0.5053 | NM_025181 | SLC35F5 | solute carrier family 35, member F5 |
| 207291_at | 0.4851 | NM_024081 | PRRG4 | proline rich Gla G-carboxyglutamic acid 4 transmembrane |
| 234997_x_at | 0.4617 | CD684982 | EST1502 | human spermidine/spermine N1 acetyl transferase |

Example 3

To further assess the extent to which gene combinations comprising one or more of the genes that have been identified herein correlate with an interferon response gene signature, the Pearson correlation of all possible three-gene combinations of 24 selected genes (Table 4A) were assessed. Data are shown in Table 4B.

Materials and Methods

PAXgene tubes from Qiagen/PreAnalytix (Valencia, Calif.) were used to collect whole blood from 35 SLE samples and 10 healthy donors. RNA was prepared by using a blood RNA isolation kit from Qiagen/PreAnalytix (Valencia, Calif.) and the expression of twenty-four interferon-alpha (IFN α) responsive genes was assayed using routine methods, e.g., by using primers/probes with TaqMan reagents from ABI (Foster City, Calif.). Relative abundance was determined by normalizing expression to RPL19. One "healthy" donor sample was removed from the analysis due to abnormally high expression of IFN responsive genes probably due to a recent viral infection. An Interferon Signature Metric (ISM) score was defined in the following manner:

1. The average expression for each gene was calculated in the normal samples ("average normal expression").
2. Ratio of expression relative to the average normal expression (step #1) was tabulated.
3. The ISM score is defined for each sample using a set of genes. The ISM score was the average of the expression ratios (step #2) for the set of genes in the given sample.

From the 24 IFNα responsive genes, it was possible to generate 2024 unique three-gene subsets. For each of the possible 2024 three-gene combination, Pearson correlations between three-gene ISM score and the twenty four-gene ISM score were calculated. All numerical analysis was performed using R (url: <r-project.org>).

Result and Analysis

While most healthy donor samples had an ISM score near one, a significant fraction of SLE patients had considerably higher ISM scores. Further, all three-gene combination ISM scores served as high quality surrogates for the twenty four-gene ISM score. The histogram for the three-gene ISM score correlation with the twenty four-gene ISM score is shown in FIG. 5. The lowest Pearson correlation was 0.73 and 70% of the correlations were greater than 0.95.

As evident from Table 4B, all combinations showed significant correlation values, with the lowest value being about 0.73. This demonstrated the usefulness and flexibility of the genes disclosed hereinabove as markers of disease. Most, but not all, of the 24 selected genes are from Tables 1, 2 and/or 3. The high correlation observed, even for combinations comprising a gene(s) that is not listed in Tables 1, 2 and/or 3, further confirmed the usefulness and broad applicability of the genes disclosed hereinabove as disease markers.

TABLE 4A

List of selected 24 genes, with corresponding RefSeq ID.

| | |
|---|---|
| EPSTI1 | NM_001002264 |
| RIG1 (DDX58) | NM_014314 |
| OAS3 | NM_006187 |
| HERC5 | NM_016323 |

TABLE 4A-continued

List of selected 24 genes, with corresponding RefSeq ID.

| | |
|---|---|
| PARP9 | NM_031458 |
| SAMD9L | NM_152703 |
| TYKI | NM_207315 |
| CHMP5 | NM_016410 |
| ZBP1 | NM_030776 |
| CIG5 (RSAD2) | NM_080657 |
| IFI44 | NM_006417 |
| IFI44L | NM_006820 |
| IFIT1 | NM_001548 |
| IFIT4 (IFIT3) | NM_001549 |
| IFIT5 | NM_012420 |
| IRF7 | NM_004029 |
| G1P2 | NM_005101 |
| MX1 | NM_002462 |
| OAS1 | NM_002534 |
| OAS2 | NM_002535 |
| OASL | NM_003733 |
| SP110 | NM_004509 |
| RIGE (LY6E) | NM_002346 |
| XIAP | NM_001167 |

TABLE 4B

All possible 3-gene combinations of a selected group of 24 genes, indicated with their respective Pearson correlation values.

| Gene 1 | Gene 2 | Gene 3 | Pearson Correlation |
|---|---|---|---|
| IFIT4 | OAS1 | MX1 | 0.996514 |
| OASL | CHMP5 | ZBP1 | 0.996478 |
| IFI44L | OASL | CIG5 | 0.996391 |
| IFI44L | CIG5 | ZBP1 | 0.995869 |
| EPSTI1 | TYKI | MX1 | 0.995702 |
| IFIT4 | HERC5 | TYKI | 0.995611 |
| IFIT4 | TYKI | XIAP | 0.995609 |
| IFI44L | OAS1 | ZBP1 | 0.995602 |
| IFI44L | IFIT4 | OASL | 0.995504 |
| IFIT4 | OAS1 | IFIT1 | 0.995422 |
| EPSTI1 | HERC5 | TYKI | 0.995392 |
| IFI44L | EPSTI1 | OASL | 0.995385 |
| IFI44L | EPSTI1 | OAS3 | 0.995345 |
| EPSTI1 | TYKI | IFIT1 | 0.99515 |
| G1P2 | SAMD9L | SP110 | 0.99489 |
| IRF7 | HERC5 | TYKI | 0.994867 |
| IFIT5 | CIG5 | ZBP1 | 0.994863 |
| IFI44L | EPSTI1 | ZBP1 | 0.994776 |
| IFI44L | SP110 | ZBP1 | 0.994649 |
| RIG1 | IRF7 | HERC5 | 0.994588 |
| TYKI | IFIT1 | XIAP | 0.994564 |
| IFIT4 | TYKI | MX1 | 0.994522 |
| OASL | IFI44 | ZBP1 | 0.994503 |
| EPSTI1 | G1P2 | SAMD9L | 0.994402 |
| IRF7 | SAMD9L | MX1 | 0.99428 |
| IFI44L | OAS2 | OASL | 0.994232 |
| IFI44L | CIG5 | SP110 | 0.994183 |
| TYKI | MX1 | XIAP | 0.994176 |
| IFI44L | OASL | IRF7 | 0.994168 |
| IFIT5 | IFIT4 | OAS3 | 0.994107 |
| IRF7 | HERC5 | SAMD9L | 0.994056 |
| OASL | CIG5 | CHMP5 | 0.994043 |
| IRF7 | TYKI | IFIT1 | 0.993998 |
| TYKI | IFIT1 | SP110 | 0.993932 |
| IFIT4 | TYKI | IFIT1 | 0.993875 |
| CIG5 | HERC5 | TYKI | 0.993865 |
| IFIT5 | IFIT4 | ZBP1 | 0.993786 |
| OAS2 | OASL | CHMP5 | 0.993676 |
| IFI44L | IFIT4 | RIGE | 0.993594 |
| EPSTI1 | OAS3 | CHMP5 | 0.993546 |
| IFI44L | IFIT4 | OAS3 | 0.993513 |
| EPSTI1 | G1P2 | TYKI | 0.993511 |
| EPSTI1 | G1P2 | HERC5 | 0.99349 |
| OAS1 | IRF7 | IFIT1 | 0.99348 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| IRF7 | TYKI | MX1 | 0.993472 |
| IFIT5 | OAS2 | ZBP1 | 0.993459 |
| IRF7 | HERC5 | IFIT1 | 0.99345 |
| IFI44L | OASL | XIAP | 0.993443 |
| OAS1 | CIG5 | IFIT1 | 0.993431 |
| IFIT4 | IRF7 | TYKI | 0.993429 |
| HERC5 | TYKI | SP110 | 0.993356 |
| IFIT4 | RIG1 | TYKI | 0.993297 |
| OAS1 | IRF7 | MX1 | 0.993259 |
| IFIT5 | IRF7 | ZBP1 | 0.993164 |
| IFIT4 | G1P2 | OAS1 | 0.993068 |
| G1P2 | IRF7 | HERC5 | 0.992975 |
| IFI44L | OAS2 | CIG5 | 0.992931 |
| CIG5 | SAMD9L | TYKI | 0.992894 |
| IRF7 | HERC5 | MX1 | 0.99289 |
| OAS2 | OASL | IFI44 | 0.992876 |
| HERC5 | TYKI | XIAP | 0.992863 |
| OASL | CIG5 | IFI44 | 0.992852 |
| CIG5 | IFI44 | ZBP1 | 0.992827 |
| IFIT5 | OAS2 | IRF7 | 0.992666 |
| IFI44L | IRF7 | CIG5 | 0.992636 |
| TYKI | MX1 | SP110 | 0.992558 |
| IFI44L | OASL | MX1 | 0.992556 |
| OAS1 | CIG5 | MX1 | 0.992546 |
| EPSTI1 | IFI44 | OAS3 | 0.992546 |
| G1P2 | CIG5 | SAMD9L | 0.992522 |
| EPSTI1 | RIG1 | TYKI | 0.99252 |
| OASL | SAMD9L | IFIT1 | 0.992509 |
| IFIT5 | EPSTI1 | ZBP1 | 0.992466 |
| IFI44L | HERC5 | RIGE | 0.992413 |
| CIG5 | TYKI | IFIT1 | 0.992392 |
| IFI44L | IRF7 | ZBP1 | 0.992374 |
| G1P2 | IRF7 | SAMD9L | 0.992327 |
| IFIT4 | SAMD9L | TYKI | 0.992311 |
| IFI44L | OASL | SP110 | 0.992307 |
| IFIT5 | OAS2 | CIG5 | 0.992229 |
| IFI44L | IFIT1 | RIGE | 0.992209 |
| IFI44L | IFIT4 | ZBP1 | 0.992195 |
| IFI44L | CIG5 | XIAP | 0.992193 |
| IFIT5 | EPSTI1 | OAS3 | 0.99217 |
| IFI44L | OAS2 | EPSTI1 | 0.992154 |
| IFI44L | EPSTI1 | CIG5 | 0.992137 |
| IFI44L | OAS2 | SP110 | 0.99207 |
| EPSTI1 | SAMD9L | TYKI | 0.99207 |
| IFI44L | MX1 | RIGE | 0.992058 |
| OASL | CHMP5 | XIAP | 0.992049 |
| G1P2 | HERC5 | XIAP | 0.992014 |
| IFI44L | OASL | IFIT1 | 0.992005 |
| G1P2 | SAMD9L | ZBP1 | 0.991994 |
| IFI44L | EPSTI1 | RIGE | 0.991991 |
| IFIT5 | OAS2 | MX1 | 0.991941 |
| IRF7 | SAMD9L | IFIT1 | 0.991891 |
| IFI44L | IRF7 | OAS3 | 0.991715 |
| IFIT4 | EPSTI1 | TYKI | 0.991674 |
| EPSTI1 | G1P2 | OAS1 | 0.991603 |
| IFI44L | OAS2 | ZBP1 | 0.991594 |
| EPSTI1 | OAS1 | MX1 | 0.991562 |
| CIG5 | HERC5 | SAMD9L | 0.99156 |
| IFIT5 | OAS3 | IFIT1 | 0.991555 |
| IFIT5 | OASL | MX1 | 0.991528 |
| OAS1 | IFIT1 | MX1 | 0.991486 |
| IFIT4 | G1P2 | SAMD9L | 0.991439 |
| IFIT5 | CIG5 | XIAP | 0.991397 |
| OAS2 | IFI44 | ZBP1 | 0.991331 |
| EPSTI1 | OASL | CHMP5 | 0.991303 |
| HERC5 | IFIT1 | XIAP | 0.991268 |
| G1P2 | HERC5 | SP110 | 0.99125 |
| CIG5 | TYKI | MX1 | 0.991247 |
| OASL | SAMD9L | MX1 | 0.991199 |
| IFIT5 | IFIT4 | OAS2 | 0.991186 |
| IFIT5 | IRF7 | OAS3 | 0.991178 |
| IFI44L | OAS2 | IRF7 | 0.991172 |
| IFIT5 | IFIT4 | OASL | 0.991098 |
| IFIT5 | IRF7 | CIG5 | 0.991095 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| IFI44L | OASL | HERC5 | 0.991094 |
| IFI44L | RIGE | XIAP | 0.99101 |
| OASL | IRF7 | CHMP5 | 0.990968 |
| IFIT4 | SAMD9L | MX1 | 0.990947 |
| IFIT5 | OAS3 | MX1 | 0.990942 |
| IFIT4 | G1P2 | HERC5 | 0.990937 |
| G1P2 | OAS1 | CIG5 | 0.990933 |
| G1P2 | IFIT1 | XIAP | 0.990886 |
| SAMD9L | MX1 | XIAP | 0.990878 |
| OAS3 | CHMP5 | SP110 | 0.990877 |
| G1P2 | TYKI | SP110 | 0.990867 |
| EPSTI1 | OAS1 | IFIT1 | 0.990838 |
| G1P2 | OASL | SAMD9L | 0.990826 |
| IFI44L | CIG5 | RIGE | 0.990812 |
| SAMD9L | TYKI | SP110 | 0.990776 |
| IFIT5 | CIG5 | MX1 | 0.990775 |
| CHMP5 | RIGE | XIAP | 0.990758 |
| OASL | TYKI | IFIT1 | 0.990748 |
| HERC5 | MX1 | XIAP | 0.990729 |
| EPSTI1 | G1P2 | IFIT1 | 0.9907 |
| IRF7 | OAS3 | CHMP5 | 0.990687 |
| EPSTI1 | OASL | IFI44 | 0.990632 |
| G1P2 | OAS1 | IFIT1 | 0.990614 |
| IFIT5 | XIAP | ZBP1 | 0.990611 |
| IFIT4 | OAS1 | HERC5 | 0.990512 |
| IFIT4 | HERC5 | SAMD9L | 0.990506 |
| EPSTI1 | IFI44 | ZBP1 | 0.990464 |
| OASL | CHMP5 | SP110 | 0.990463 |
| IFIT5 | OASL | IFIT1 | 0.990412 |
| EPSTI1 | TYKI | XIAP | 0.990325 |
| EPSTI1 | IRF7 | TYKI | 0.990315 |
| G1P2 | SAMD9L | XIAP | 0.990306 |
| IFI44L | CIG5 | OAS3 | 0.990281 |
| IFIT5 | OAS2 | EPSTI1 | 0.990115 |
| CIG5 | SAMD9L | MX1 | 0.990079 |
| SAMD9L | TYKI | ZBP1 | 0.989993 |
| OAS2 | TYKI | IFIT1 | 0.989986 |
| EPSTI1 | SAMD9L | MX1 | 0.989945 |
| IFI44 | RIGE | ZBP1 | 0.989942 |
| IFIT5 | MX1 | RIGE | 0.989937 |
| IFI44L | OAS3 | SP110 | 0.989929 |
| IFIT5 | MX1 | ZBP1 | 0.98985 |
| IFI44L | SAMD9L | RIGE | 0.989814 |
| CIG5 | IFI44 | RIGE | 0.989794 |
| OAS2 | CIG5 | IFI44 | 0.989763 |
| OASL | HERC5 | SAMD9L | 0.989717 |
| IFIT4 | IRF7 | SAMD9L | 0.989667 |
| IFIT5 | IFIT1 | RIGE | 0.989587 |
| IFIT4 | IRF7 | HERC5 | 0.989574 |
| IFIT5 | OASL | ZBP1 | 0.989563 |
| TYKI | IFIT1 | ZBP1 | 0.989561 |
| G1P2 | CIG5 | HERC5 | 0.989534 |
| HERC5 | TYKI | MX1 | 0.9895 |
| EPSTI1 | IFI44 | RIGE | 0.989498 |
| G1P2 | OAS1 | MX1 | 0.989491 |
| IRF7 | SAMD9L | TYKI | 0.989455 |
| CIG5 | IFI44 | OAS3 | 0.989384 |
| IFIT5 | OASL | CIG5 | 0.989345 |
| IFIT4 | G1P2 | TYKI | 0.989323 |
| IFI44L | OAS3 | HERC5 | 0.989322 |
| IFIT4 | TYKI | ZBP1 | 0.989292 |
| IFIT5 | SP110 | ZBP1 | 0.98929 |
| IFI44 | SP110 | ZBP1 | 0.989289 |
| IFI44L | XIAP | ZBP1 | 0.989258 |
| HERC5 | TYKI | IFIT1 | 0.989244 |
| IFIT5 | OAS2 | IFIT1 | 0.989239 |
| EPSTI1 | G1P2 | MX1 | 0.98921 |
| G1P2 | IRF7 | IFIT1 | 0.989159 |
| IFI44L | IFIT4 | OAS2 | 0.989146 |
| OAS3 | CHMP5 | XIAP | 0.989141 |
| OASL | OAS3 | CHMP5 | 0.989136 |
| OASL | IFI44 | XIAP | 0.989112 |
| IFI44L | EPSTI1 | SP110 | 0.989091 |
| IFI44L | IRF7 | SP110 | 0.989077 |
| IFI44L | IFIT4 | CIG5 | 0.989073 |
| CIG5 | OAS3 | CHMP5 | 0.989057 |
| IFI44 | RIGE | XIAP | 0.989037 |
| CIG5 | SAMD9L | IFIT1 | 0.989029 |
| IFI44L | CIG5 | HERC5 | 0.989011 |
| IFIT5 | OAS3 | HERC5 | 0.988963 |
| IFIT4 | HERC5 | XIAP | 0.988945 |
| IFIT4 | HERC5 | MX1 | 0.988925 |
| IFIT5 | OAS3 | XIAP | 0.988891 |
| IFI44L | IFIT4 | SP110 | 0.988869 |
| IFI44L | OAS3 | XIAP | 0.988845 |
| CHMP5 | RIGE | ZBP1 | 0.988767 |
| CIG5 | CHMP5 | RIGE | 0.988756 |
| IFI44L | OAS3 | IFIT1 | 0.988746 |
| RIG1 | IRF7 | SAMD9L | 0.988717 |
| IFI44 | MX1 | RIGE | 0.988705 |
| SAMD9L | IFIT1 | XIAP | 0.988634 |
| EPSTI1 | CHMP5 | RIGE | 0.988543 |
| IFI44L | CIG5 | MX1 | 0.988509 |
| IFIT5 | MX1 | SP110 | 0.988438 |
| HERC5 | TYKI | ZBP1 | 0.988437 |
| OAS1 | IFIT1 | ZBP1 | 0.988433 |
| IFIT4 | HERC5 | IFIT1 | 0.988422 |
| IRF7 | TYKI | XIAP | 0.988382 |
| IFIT5 | IFIT1 | ZBP1 | 0.988359 |
| IFIT5 | OAS2 | OASL | 0.988341 |
| IFIT5 | IFIT4 | CIG5 | 0.988316 |
| SAMD9L | IFIT1 | ZBP1 | 0.988312 |
| G1P2 | IFIT1 | SP110 | 0.988303 |
| OAS1 | IFIT1 | XIAP | 0.9883 |
| OASL | SAMD9L | TYKI | 0.988278 |
| HERC5 | CHMP5 | RIGE | 0.988269 |
| IFIT4 | OAS1 | TYKI | 0.988268 |
| OAS2 | OAS1 | IFIT1 | 0.988248 |
| G1P2 | MX1 | XIAP | 0.988232 |
| OAS1 | HERC5 | MX1 | 0.988215 |
| OAS1 | CIG5 | HERC5 | 0.988211 |
| HERC5 | SAMD9L | ZBP1 | 0.988167 |
| OAS2 | HERC5 | TYKI | 0.988163 |
| IFI44 | OAS3 | ZBP1 | 0.988139 |
| CIG5 | CHMP5 | ZBP1 | 0.988136 |
| IFI44L | IRF7 | RIGE | 0.988106 |
| IFIT4 | IFI44 | OAS3 | 0.988101 |
| OAS2 | SAMD9L | TYKI | 0.988081 |
| IFIT5 | CIG5 | IFIT1 | 0.988073 |
| IFIT5 | EPSTI1 | CIG5 | 0.988072 |
| IFIT4 | OASL | IFI44 | 0.98801 |
| IFI44 | HERC5 | RIGE | 0.987984 |
| IFIT4 | G1P2 | XIAP | 0.987951 |
| IFI44L | MX1 | SP110 | 0.98795 |
| OAS1 | MX1 | XIAP | 0.987945 |
| RIG1 | IRF7 | IFIT1 | 0.987936 |
| IFIT4 | RIG1 | HERC5 | 0.987933 |
| IFIT4 | SAMD9L | IFIT1 | 0.987928 |
| IFI44L | EPSTI1 | IRF7 | 0.987927 |
| IFIT4 | OAS1 | IRF7 | 0.987914 |
| IFIT5 | OASL | XIAP | 0.987913 |
| IFIT5 | CIG5 | OAS3 | 0.987904 |
| IFIT4 | SAMD9L | XIAP | 0.987896 |
| OAS2 | G1P2 | SAMD9L | 0.987775 |
| OASL | HERC5 | IFIT1 | 0.987735 |
| IRF7 | IFI44 | OAS3 | 0.987734 |
| IFIT5 | CIG5 | HERC5 | 0.98773 |
| EPSTI1 | HERC5 | MX1 | 0.987723 |
| G1P2 | CIG5 | TYKI | 0.98772 |
| IFIT5 | IFIT4 | RIGE | 0.987715 |
| IFI44L | RIGE | ZBP1 | 0.987715 |
| IFIT5 | OASL | IRF7 | 0.987699 |
| OAS1 | HERC5 | IFIT1 | 0.987696 |
| EPSTI1 | HERC5 | SAMD9L | 0.987685 |
| OASL | IRF7 | IFI44 | 0.98768 |
| IFI44L | RIG1 | OASL | 0.987635 |
| EPSTI1 | RIG1 | G1P2 | 0.987607 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| IFIT4 | CIG5 | TYKI | 0.987605 |
| OAS2 | EPSTI1 | IFI44 | 0.987589 |
| IFIT5 | OAS2 | XIAP | 0.987588 |
| OAS2 | TYKI | MX1 | 0.987555 |
| OASL | IFI44 | MX1 | 0.987554 |
| CHMP5 | MX1 | RIGE | 0.987534 |
| IFI44L | OAS3 | MX1 | 0.987521 |
| IFI44 | OAS3 | SP110 | 0.987441 |
| EPSTI1 | HERC5 | IFIT1 | 0.987435 |
| G1P2 | HERC5 | IFIT1 | 0.987431 |
| IFIT4 | TYKI | SP110 | 0.9874 |
| OAS2 | IFI44 | RIGE | 0.987335 |
| IRF7 | HERC5 | XIAP | 0.987327 |
| OAS3 | CHMP5 | ZBP1 | 0.987314 |
| HERC5 | SAMD9L | XIAP | 0.987305 |
| G1P2 | HERC5 | SAMD9L | 0.987303 |
| OASL | HERC5 | TYKI | 0.987292 |
| RIG1 | IRF7 | TYKI | 0.987272 |
| IFI44 | OAS3 | XIAP | 0.987263 |
| OASL | TYKI | MX1 | 0.987226 |
| SAMD9L | MX1 | ZBP1 | 0.987216 |
| G1P2 | TYKI | XIAP | 0.987186 |
| RIG1 | IFIT1 | XIAP | 0.987143 |
| CIG5 | HERC5 | IFIT1 | 0.987143 |
| OASL | CHMP5 | MX1 | 0.987113 |
| IFIT5 | CIG5 | SP110 | 0.987103 |
| HERC5 | SAMD9L | MX1 | 0.987078 |
| EPSTI1 | SAMD9L | IFIT1 | 0.987021 |
| IFI44L | EPSTI1 | XIAP | 0.986996 |
| IFIT4 | G1P2 | IFIT1 | 0.986962 |
| IFIT5 | OAS2 | SP110 | 0.986961 |
| TYKI | IFIT1 | MX1 | 0.986955 |
| IFI44 | IFIT1 | RIGE | 0.98694 |
| G1P2 | OAS1 | IRF7 | 0.986929 |
| RIG1 | TYKI | XIAP | 0.986927 |
| IFI44L | SP110 | XIAP | 0.986913 |
| IFIT5 | EPSTI1 | OASL | 0.986895 |
| OASL | IFI44 | SP110 | 0.986847 |
| SAMD9L | MX1 | SP110 | 0.986839 |
| IFIT4 | IFIT1 | XIAP | 0.986801 |
| G1P2 | SAMD9L | MX1 | 0.986792 |
| SAMD9L | TYKI | MX1 | 0.986776 |
| IFIT1 | MX1 | XIAP | 0.986772 |
| RIG1 | HERC5 | XIAP | 0.986653 |
| IFIT4 | SAMD9L | ZBP1 | 0.986638 |
| CIG5 | IFI44 | SP110 | 0.986615 |
| RIG1 | TYKI | MX1 | 0.986584 |
| IFI44L | CIG5 | IFIT1 | 0.986574 |
| CIG5 | TYKI | XIAP | 0.986567 |
| SAMD9L | TYKI | XIAP | 0.986554 |
| IFI44L | RIG1 | RIGE | 0.986514 |
| IFIT4 | OASL | CHMP5 | 0.986483 |
| IFI44L | OAS2 | MX1 | 0.986478 |
| CIG5 | IFI44 | XIAP | 0.98647 |
| IFI44L | G1P2 | RIGE | 0.986469 |
| IRF7 | IFI44 | ZBP1 | 0.986437 |
| EPSTI1 | CIG5 | IFI44 | 0.986418 |
| RIG1 | CIG5 | TYKI | 0.986387 |
| RIG1 | TYKI | IFIT1 | 0.986336 |
| IFIT5 | EPSTI1 | MX1 | 0.986313 |
| IRF7 | IFIT1 | XIAP | 0.986307 |
| IFIT4 | MX1 | XIAP | 0.98627 |
| IFIT4 | OAS3 | CHMP5 | 0.986258 |
| G1P2 | IRF7 | MX1 | 0.986258 |
| OAS2 | IFI44 | SP110 | 0.986255 |
| IFIT5 | G1P2 | CIG5 | 0.986247 |
| IFI44L | HERC5 | SP110 | 0.986229 |
| G1P2 | OASL | IFIT1 | 0.986183 |
| G1P2 | SAMD9L | IFIT1 | 0.986168 |
| TYKI | MX1 | ZBP1 | 0.986151 |
| CHMP5 | IFIT1 | RIGE | 0.986136 |
| OAS1 | IRF7 | HERC5 | 0.986057 |
| IRF7 | IFIT1 | MX1 | 0.986039 |
| IFIT5 | HERC5 | RIGE | 0.985983 |
| IFIT5 | OAS2 | HERC5 | 0.985946 |
| RIG1 | IRF7 | MX1 | 0.985944 |
| IFI44 | XIAP | ZBP1 | 0.985944 |
| IFI44L | G1P2 | OASL | 0.985941 |
| IFIT5 | OASL | HERC5 | 0.98592 |
| G1P2 | HERC5 | MX1 | 0.985913 |
| OAS2 | OAS1 | MX1 | 0.98591 |
| IFIT5 | G1P2 | ZBP1 | 0.985875 |
| OAS1 | CIG5 | TYKI | 0.985852 |
| RIG1 | G1P2 | HERC5 | 0.985831 |
| OAS1 | OASL | IFIT1 | 0.985827 |
| G1P2 | CIG5 | IFIT1 | 0.985799 |
| IFI44L | OAS3 | ZBP1 | 0.985763 |
| IFI44L | OAS2 | XIAP | 0.985746 |
| IFIT5 | HERC5 | ZBP1 | 0.985738 |
| RIG1 | HERC5 | MX1 | 0.985734 |
| IRF7 | CIG5 | TYKI | 0.985724 |
| CIG5 | HERC5 | MX1 | 0.985709 |
| IFIT4 | RIG1 | SAMD9L | 0.985702 |
| OAS2 | SAMD9L | MX1 | 0.985696 |
| OAS3 | HERC5 | CHMP5 | 0.985677 |
| OASL | HERC5 | CHMP5 | 0.985675 |
| EPSTI1 | G1P2 | XIAP | 0.985614 |
| IFIT4 | G1P2 | MX1 | 0.985575 |
| OAS2 | SAMD9L | IFIT1 | 0.985558 |
| IFI44 | OAS3 | HERC5 | 0.985493 |
| IFIT4 | OASL | TYKI | 0.985491 |
| IFIT5 | OAS2 | G1P2 | 0.985467 |
| CHMP5 | SP110 | ZBP1 | 0.985431 |
| RIG1 | MX1 | XIAP | 0.985418 |
| IFI44L | HERC5 | ZBP1 | 0.985411 |
| G1P2 | HERC5 | ZBP1 | 0.985399 |
| IFI44L | MX1 | ZBP1 | 0.985399 |
| RIG1 | HERC5 | IFIT1 | 0.985388 |
| OASL | IFI44 | IFIT1 | 0.985349 |
| RIG1 | OAS1 | MX1 | 0.985314 |
| IFIT4 | IFI44 | ZBP1 | 0.985306 |
| IFIT4 | OASL | SAMD9L | 0.985271 |
| OASL | IFI44 | HERC5 | 0.985262 |
| IFIT4 | OAS2 | TYKI | 0.985259 |
| IRF7 | CHMP5 | RIGE | 0.985241 |
| G1P2 | IRF7 | TYKI | 0.98524 |
| RIG1 | SAMD9L | MX1 | 0.985203 |
| G1P2 | OASL | HERC5 | 0.985184 |
| IFI44L | IFIT4 | EPSTI1 | 0.985167 |
| SAMD9L | IFIT1 | SP110 | 0.985161 |
| HERC5 | SAMD9L | SP110 | 0.985136 |
| IFI44L | EPSTI1 | MX1 | 0.985133 |
| IFIT4 | CHMP5 | RIGE | 0.985089 |
| IFI44L | IFIT1 | SP110 | 0.985074 |
| OASL | CHMP5 | IFIT1 | 0.985052 |
| IFI44L | OAS2 | RIGE | 0.985038 |
| OAS1 | MX1 | ZBP1 | 0.985036 |
| IFIT5 | G1P2 | SP110 | 0.985035 |
| RIG1 | HERC5 | TYKI | 0.98502 |
| IFI44L | OAS2 | HERC5 | 0.985013 |
| OASL | IFI44 | OAS3 | 0.984994 |
| IFIT5 | OAS3 | ZBP1 | 0.984992 |
| IRF7 | CIG5 | IFI44 | 0.984947 |
| EPSTI1 | CHMP5 | ZBP1 | 0.984947 |
| IFI44L | G1P2 | SP110 | 0.984929 |
| IFIT5 | IFIT4 | SP110 | 0.984889 |
| IFI44 | OAS3 | MX1 | 0.984882 |
| IFIT5 | IFIT4 | XIAP | 0.984858 |
| G1P2 | OAS1 | ZBP1 | 0.984857 |
| IFI44L | OAS2 | IFIT1 | 0.984833 |
| IFIT5 | EPSTI1 | IRF7 | 0.984785 |
| IFI44L | IFIT1 | ZBP1 | 0.984771 |
| G1P2 | OAS1 | HERC5 | 0.984751 |
| IFI44L | OAS3 | SAMD9L | 0.984637 |
| IFIT5 | EPSTI1 | XIAP | 0.984622 |
| OAS2 | IRF7 | IFI44 | 0.984619 |
| IFIT4 | IRF7 | IFIT1 | 0.984565 |
| IFIT5 | IFIT1 | SP110 | 0.984547 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| SAMD9L | TYKI | IFIT1 | 0.984535 |
| HERC5 | SAMD9L | IFIT1 | 0.984528 |
| IFI44L | CIG5 | TYKI | 0.984518 |
| RIG1 | OAS1 | IFIT1 | 0.984505 |
| IFI44L | OASL | SAMD9L | 0.984455 |
| IRF7 | IFI44 | RIGE | 0.984421 |
| IFI44L | G1P2 | CIG5 | 0.98441 |
| OAS2 | CHMP5 | RIGE | 0.98438 |
| G1P2 | TYKI | IFIT1 | 0.984362 |
| IFIT5 | G1P2 | OASL | 0.98435 |
| SAMD9L | CHMP5 | RIGE | 0.98435 |
| IFIT4 | OAS1 | CIG5 | 0.984347 |
| OAS2 | HERC5 | SAMD9L | 0.98434 |
| IFIT4 | G1P2 | IRF7 | 0.984323 |
| G1P2 | HERC5 | TYKI | 0.984302 |
| IRF7 | CIG5 | SAMD9L | 0.984261 |
| EPSTI1 | G1P2 | IRF7 | 0.984258 |
| OAS1 | TYKI | MX1 | 0.984212 |
| IFI44L | RIG1 | CIG5 | 0.984189 |
| IFI44 | OAS3 | IFIT1 | 0.984148 |
| OAS1 | CIG5 | SAMD9L | 0.984088 |
| IRF7 | SAMD9L | XIAP | 0.984046 |
| IFIT4 | OAS1 | XIAP | 0.983986 |
| G1P2 | MX1 | SP110 | 0.983965 |
| OAS1 | TYKI | IFIT1 | 0.983952 |
| IFIT4 | OAS1 | SAMD9L | 0.983939 |
| IRF7 | MX1 | XIAP | 0.983917 |
| G1P2 | IFI44 | RIGE | 0.983911 |
| EPSTI1 | OAS1 | TYKI | 0.983904 |
| IFI44L | OASL | TYKI | 0.983891 |
| IFIT5 | OAS2 | PARP9 | 0.983888 |
| RIG1 | G1P2 | XIAP | 0.983881 |
| IFIT5 | G1P2 | RIGE | 0.983874 |
| OAS2 | CHMP5 | ZBP1 | 0.983861 |
| IFIT4 | RIG1 | OAS1 | 0.983828 |
| G1P2 | IFIT1 | ZBP1 | 0.983828 |
| IFIT4 | IRF7 | MX1 | 0.983803 |
| OASL | HERC5 | MX1 | 0.983775 |
| RIG1 | CIG5 | SAMD9L | 0.983728 |
| IFIT5 | RIGE | XIAP | 0.983696 |
| HERC5 | IFIT1 | SP110 | 0.983625 |
| IFIT5 | CIG5 | PARP9 | 0.983607 |
| OASL | CHMP5 | RIGE | 0.983598 |
| IFI44L | IFIT4 | XIAP | 0.983588 |
| IRF7 | SAMD9L | ZBP1 | 0.983584 |
| IFIT5 | OAS3 | SAMD9L | 0.983578 |
| G1P2 | TYKI | ZBP1 | 0.983567 |
| EPSTI1 | OAS1 | HERC5 | 0.983564 |
| HERC5 | IFIT1 | MX1 | 0.983432 |
| IFIT4 | EPSTI1 | G1P2 | 0.98341 |
| IFIT5 | MX1 | XIAP | 0.983401 |
| SAMD9L | IFIT1 | MX1 | 0.983359 |
| OAS3 | CHMP5 | MX1 | 0.983261 |
| OAS2 | IFI44 | OAS3 | 0.983253 |
| IFIT4 | OAS1 | ZBP1 | 0.983249 |
| G1P2 | IRF7 | XIAP | 0.983205 |
| OAS3 | CHMP5 | IFIT1 | 0.983177 |
| HERC5 | IFIT1 | ZBP1 | 0.983163 |
| IFIT5 | IFIT4 | EPSTI1 | 0.983135 |
| IFIT5 | OAS3 | SP110 | 0.983121 |
| OAS1 | IFIT1 | SP110 | 0.983118 |
| OAS2 | CIG5 | CHMP5 | 0.983111 |
| IFI44L | OASL | OAS3 | 0.983103 |
| G1P2 | OAS1 | SP110 | 0.983094 |
| G1P2 | OAS1 | XIAP | 0.983073 |
| EPSTI1 | IRF7 | HERC5 | 0.983059 |
| IFIT5 | EPSTI1 | G1P2 | 0.983057 |
| IFIT5 | IFIT4 | IRF7 | 0.983047 |
| IFI44L | EPSTI1 | HERC5 | 0.982974 |
| OAS2 | G1P2 | OAS1 | 0.982973 |
| IFIT4 | RIG1 | G1P2 | 0.98284 |
| EPSTI1 | IRF7 | SAMD9L | 0.982832 |
| OAS3 | SAMD9L | IFIT1 | 0.98283 |
| G1P2 | TYKI | MX1 | 0.982823 |
| IFIT5 | IRF7 | MX1 | 0.982823 |
| CIG5 | IFI44 | MX1 | 0.982815 |
| IFIT5 | IRF7 | SP110 | 0.982806 |
| EPSTI1 | IFIT1 | MX1 | 0.982804 |
| OAS2 | G1P2 | HERC5 | 0.982779 |
| HERC5 | SAMD9L | TYKI | 0.982773 |
| OASL | TYKI | CHMP5 | 0.98276 |
| OAS1 | SAMD9L | MX1 | 0.982709 |
| IFI44L | TYKI | RIGE | 0.982691 |
| IFI44L | RIG1 | OAS3 | 0.982688 |
| IFIT4 | IFIT1 | MX1 | 0.982616 |
| EPSTI1 | CIG5 | TYKI | 0.982605 |
| G1P2 | CIG5 | MX1 | 0.982585 |
| TYKI | CHMP5 | RIGE | 0.982585 |
| IFI44L | IFIT4 | IRF7 | 0.982564 |
| IFIT5 | CIG5 | TYKI | 0.982489 |
| G1P2 | CHMP5 | RIGE | 0.98248 |
| IFIT5 | OAS3 | PARP9 | 0.982456 |
| IFIT4 | EPSTI1 | OAS1 | 0.98245 |
| CIG5 | CHMP5 | XIAP | 0.982444 |
| IRF7 | CHMP5 | ZBP1 | 0.982443 |
| IFIT5 | SAMD9L | RIGE | 0.982442 |
| CIG5 | CHMP5 | SP110 | 0.982432 |
| IFIT5 | EPSTI1 | IFIT1 | 0.982364 |
| IFIT5 | G1P2 | OAS3 | 0.982346 |
| OAS2 | IFI44 | XIAP | 0.982312 |
| CIG5 | IFI44 | HERC5 | 0.982284 |
| OAS2 | G1P2 | TYKI | 0.982279 |
| RIG1 | G1P2 | IFIT1 | 0.982209 |
| IFI44L | EPSTI1 | G1P2 | 0.982198 |
| OASL | IFIT1 | MX1 | 0.982165 |
| OAS1 | OASL | MX1 | 0.982158 |
| IFIT4 | RIG1 | MX1 | 0.982123 |
| IFI44L | TYKI | SP110 | 0.982105 |
| IFIT5 | RIG1 | ZBP1 | 0.982033 |
| IFI44L | SP110 | RIGE | 0.982032 |
| IFI44L | EPSTI1 | IFIT1 | 0.982017 |
| IFIT4 | CIG5 | SAMD9L | 0.981999 |
| IFIT5 | IFIT4 | MX1 | 0.981994 |
| IFIT5 | RIG1 | OAS3 | 0.981987 |
| OAS2 | IFI44 | MX1 | 0.981967 |
| OAS2 | G1P2 | IFIT1 | 0.981944 |
| IFIT4 | OAS2 | IFI44 | 0.981942 |
| IFIT5 | CIG5 | RIGE | 0.981929 |
| RIG1 | G1P2 | SAMD9L | 0.981924 |
| EPSTI1 | TYKI | ZBP1 | 0.981909 |
| IFIT5 | RIG1 | CIG5 | 0.9819 |
| IFI44L | G1P2 | ZBP1 | 0.981887 |
| OAS2 | HERC5 | IFIT1 | 0.981886 |
| G1P2 | OASL | IFI44 | 0.981878 |
| IFI44 | SAMD9L | RIGE | 0.981874 |
| IFIT5 | SP110 | XIAP | 0.981729 |
| CIG5 | PARP9 | SAMD9L | 0.981712 |
| OAS3 | HERC5 | SAMD9L | 0.981703 |
| EPSTI1 | RIG1 | HERC5 | 0.981663 |
| IFIT5 | EPSTI1 | RIGE | 0.981653 |
| RIG1 | SAMD9L | ZBP1 | 0.981639 |
| HERC5 | MX1 | SP110 | 0.981627 |
| IFIT5 | IRF7 | XIAP | 0.981625 |
| IFIT4 | RIG1 | IFIT1 | 0.981605 |
| IFI44 | MX1 | ZBP1 | 0.9816 |
| RIG1 | G1P2 | IRF7 | 0.98159 |
| IFI44L | CIG5 | PARP9 | 0.981588 |
| IRF7 | TYKI | ZBP1 | 0.981572 |
| IFI44L | OAS1 | CIG5 | 0.981535 |
| OAS1 | MX1 | SP110 | 0.981522 |
| IRF7 | CIG5 | HERC5 | 0.981504 |
| OASL | IFI44 | RIGE | 0.98145 |
| IFIT5 | HERC5 | SP110 | 0.981389 |
| IFIT4 | CIG5 | IFI44 | 0.981344 |
| EPSTI1 | PARP9 | TYKI | 0.981338 |
| IFI44L | IRF7 | XIAP | 0.981327 |
| G1P2 | IFIT1 | MX1 | 0.981177 |
| SAMD9L | IFIT1 | RIGE | 0.981164 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| CHMP5 | XIAP | ZBP1 | 0.981034 |
| IRF7 | CIG5 | CHMP5 | 0.98102 |
| IFI44L | CIG5 | SAMD9L | 0.980991 |
| G1P2 | OASL | TYKI | 0.980952 |
| IFIT4 | EPSTI1 | SAMD9L | 0.980931 |
| CIG5 | SAMD9L | XIAP | 0.98087 |
| IFI44L | RIG1 | ZBP1 | 0.980847 |
| G1P2 | OASL | CHMP5 | 0.98084 |
| RIG1 | CIG5 | HERC5 | 0.980836 |
| IFI44L | OAS2 | G1P2 | 0.980731 |
| IFI44L | OAS2 | TYKI | 0.980703 |
| IFIT5 | OAS2 | RIG1 | 0.980656 |
| IFI44L | EPSTI1 | TYKI | 0.980647 |
| RIG1 | TYKI | SP110 | 0.980579 |
| EPSTI1 | IFIT1 | XIAP | 0.980575 |
| IFI44 | SP110 | RIGE | 0.980565 |
| IFI44 | HERC5 | ZBP1 | 0.980564 |
| EPSTI1 | CIG5 | CHMP5 | 0.980544 |
| EPSTI1 | IFI44 | XIAP | 0.980516 |
| IFIT5 | OAS2 | TYKI | 0.980487 |
| EPSTI1 | IRF7 | IFIT1 | 0.980474 |
| IFI44L | TYKI | ZBP1 | 0.98047 |
| IFI44L | OAS2 | OAS3 | 0.980469 |
| EPSTI1 | IFI44 | SP110 | 0.980453 |
| OAS1 | OAS3 | IFIT1 | 0.980399 |
| G1P2 | OASL | MX1 | 0.980398 |
| OAS1 | CHMP5 | RIGE | 0.980281 |
| IFIT5 | EPSTI1 | HERC5 | 0.98028 |
| OAS1 | SAMD9L | IFIT1 | 0.980165 |
| OAS3 | TYKI | CHMP5 | 0.980145 |
| IFIT4 | EPSTI1 | HERC5 | 0.980116 |
| OAS2 | EPSTI1 | CHMP5 | 0.980093 |
| IFI44L | OAS3 | TYKI | 0.980031 |
| EPSTI1 | HERC5 | XIAP | 0.980031 |
| RIG1 | SAMD9L | IFIT1 | 0.98002 |
| IFI44L | OAS1 | RIGE | 0.980003 |
| G1P2 | SAMD9L | RIGE | 0.979981 |
| IFIT5 | IFIT1 | XIAP | 0.979977 |
| IFI44L | OASL | PARP9 | 0.979964 |
| CHMP5 | SP110 | RIGE | 0.979922 |
| OAS2 | OAS3 | CHMP5 | 0.979909 |
| IFIT5 | EPSTI1 | SP110 | 0.97989 |
| RIG1 | HERC5 | SAMD9L | 0.97989 |
| OAS2 | CHMP5 | SP110 | 0.979884 |
| G1P2 | SAMD9L | TYKI | 0.979881 |
| IFIT5 | OAS2 | OAS3 | 0.979865 |
| CIG5 | IFIT1 | MX1 | 0.97981 |
| IFI44L | G1P2 | OAS3 | 0.979733 |
| IFIT5 | TYKI | ZBP1 | 0.97972 |
| CIG5 | IFI44 | IFIT1 | 0.979594 |
| OAS2 | IFI44 | HERC5 | 0.979577 |
| IFIT4 | PARP9 | TYKI | 0.979539 |
| OAS1 | OAS3 | CHMP5 | 0.979509 |
| IFIT5 | IRF7 | RIGE | 0.979509 |
| TYKI | XIAP | ZBP1 | 0.979497 |
| EPSTI1 | MX1 | XIAP | 0.979484 |
| CIG5 | HERC5 | XIAP | 0.979467 |
| IFIT5 | RIGE | ZBP1 | 0.979447 |
| OAS3 | SAMD9L | CHMP5 | 0.979429 |
| IFIT5 | IRF7 | IFIT1 | 0.979416 |
| EPSTI1 | IRF7 | IFI44 | 0.979334 |
| G1P2 | CIG5 | IFI44 | 0.979329 |
| IFIT4 | G1P2 | ZBP1 | 0.979297 |
| IFIT4 | OASL | IFIT1 | 0.979261 |
| EPSTI1 | IRF7 | MX1 | 0.979237 |
| IFI44 | IFIT1 | ZBP1 | 0.979214 |
| IFI44L | MX1 | XIAP | 0.979195 |
| HERC5 | MX1 | ZBP1 | 0.979186 |
| IFI44L | IRF7 | MX1 | 0.979186 |
| OAS1 | PARP9 | IFIT1 | 0.979168 |
| OAS2 | IRF7 | TYKI | 0.979158 |
| EPSTI1 | RIG1 | IFIT1 | 0.979136 |
| EPSTI1 | RIG1 | MX1 | 0.979132 |
| IFI44L | OAS3 | PARP9 | 0.979131 |
| IFI44 | MX1 | SP110 | 0.979127 |
| OAS1 | IRF7 | CIG5 | 0.979073 |
| IFIT4 | PARP9 | SAMD9L | 0.979062 |
| IFIT4 | HERC5 | ZBP1 | 0.979058 |
| RIG1 | CHMP5 | RIGE | 0.979057 |
| G1P2 | CIG5 | XIAP | 0.979049 |
| OAS1 | HERC5 | ZBP1 | 0.979026 |
| IFI44L | OASL | RIGE | 0.979004 |
| OAS2 | IRF7 | CHMP5 | 0.978997 |
| EPSTI1 | RIG1 | SAMD9L | 0.978996 |
| OASL | IRF7 | SAMD9L | 0.978946 |
| OAS2 | HERC5 | MX1 | 0.978889 |
| HERC5 | SAMD9L | RIGE | 0.978849 |
| IFIT4 | CIG5 | HERC5 | 0.978822 |
| IFIT4 | OASL | HERC5 | 0.978804 |
| RIG1 | G1P2 | MX1 | 0.978789 |
| IFIT5 | CIG5 | SAMD9L | 0.978769 |
| IFI44L | OAS1 | OAS3 | 0.978759 |
| OAS3 | SAMD9L | MX1 | 0.978718 |
| RIG1 | TYKI | ZBP1 | 0.978668 |
| G1P2 | IFI44 | ZBP1 | 0.978638 |
| EPSTI1 | IFI44 | MX1 | 0.97863 |
| OAS2 | IFI44 | IFIT1 | 0.978619 |
| CIG5 | PARP9 | TYKI | 0.978512 |
| EPSTI1 | PARP9 | SAMD9L | 0.978467 |
| EPSTI1 | SAMD9L | XIAP | 0.978424 |
| IFIT5 | OAS3 | TYKI | 0.978409 |
| IFIT5 | OASL | SP110 | 0.978403 |
| IFI44 | SP110 | XIAP | 0.978398 |
| IFI44L | IFIT4 | MX1 | 0.978348 |
| IFI44L | OAS2 | RIG1 | 0.978343 |
| CIG5 | IFIT1 | XIAP | 0.978337 |
| RIG1 | OASL | CHMP5 | 0.978325 |
| IFI44L | SAMD9L | ZBP1 | 0.978297 |
| IFIT5 | IFIT4 | IFIT1 | 0.978296 |
| OAS1 | IRF7 | TYKI | 0.97822 |
| IFIT5 | OASL | SAMD9L | 0.978202 |
| IRF7 | TYKI | SP110 | 0.978191 |
| SAMD9L | MX1 | RIGE | 0.978177 |
| IFIT5 | OASL | TYKI | 0.978163 |
| PARP9 | SAMD9L | XIAP | 0.978139 |
| G1P2 | IFI44 | OAS3 | 0.978119 |
| OAS1 | HERC5 | XIAP | 0.97802 |
| IFIT4 | OAS2 | SAMD9L | 0.978019 |
| IFI44L | IRF7 | HERC5 | 0.978014 |
| RIG1 | OASL | SAMD9L | 0.97801 |
| G1P2 | MX1 | ZBP1 | 0.977958 |
| IFI44L | OAS2 | PARP9 | 0.977945 |
| OAS3 | SAMD9L | TYKI | 0.977935 |
| PARP9 | IFIT1 | XIAP | 0.977901 |
| G1P2 | OAS1 | OASL | 0.977848 |
| IFIT4 | OAS2 | OAS1 | 0.977813 |
| IFI44 | OAS3 | SAMD9L | 0.977801 |
| IFI44 | TYKI | RIGE | 0.97779 |
| IFIT5 | SAMD9L | ZBP1 | 0.977734 |
| OAS2 | EPSTI1 | TYKI | 0.977724 |
| PARP9 | SAMD9L | IFIT1 | 0.977718 |
| RIG1 | SAMD9L | XIAP | 0.977704 |
| OAS3 | TYKI | IFIT1 | 0.977699 |
| IFIT5 | RIG1 | OASL | 0.977613 |
| TYKI | SP110 | XIAP | 0.977603 |
| PARP9 | TYKI | IFIT1 | 0.977602 |
| G1P2 | OAS1 | SAMD9L | 0.977585 |
| PARP9 | TYKI | XIAP | 0.977542 |
| OASL | IFI44 | TYKI | 0.977504 |
| IFIT5 | IRF7 | HERC5 | 0.977473 |
| IRF7 | IFI44 | SP110 | 0.977459 |
| IFIT5 | EPSTI1 | TYKI | 0.977454 |
| IRF7 | CIG5 | IFIT1 | 0.977446 |
| OAS2 | OAS1 | HERC5 | 0.977433 |
| CIG5 | TYKI | CHMP5 | 0.977361 |
| IFIT5 | IFIT4 | HERC5 | 0.977353 |
| IFIT4 | EPSTI1 | MX1 | 0.977281 |
| IFI44L | RIG1 | SP110 | 0.977267 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| IFIT5 | OASL | PARP9 | 0.977265 |
| IFIT4 | EPSTI1 | IFIT1 | 0.977256 |
| RIG1 | IFIT1 | MX1 | 0.977255 |
| IFI44L | IFIT4 | HERC5 | 0.977207 |
| IFIT4 | G1P2 | CIG5 | 0.977176 |
| CIG5 | IFI44 | TYKI | 0.9771 |
| OAS1 | TYKI | ZBP1 | 0.977098 |
| OAS2 | G1P2 | IFI44 | 0.977092 |
| OASL | SAMD9L | CHMP5 | 0.977068 |
| IFIT4 | IFI44 | SP110 | 0.977067 |
| G1P2 | PARP9 | SAMD9L | 0.977067 |
| IFIT4 | CHMP5 | ZBP1 | 0.977042 |
| CIG5 | HERC5 | CHMP5 | 0.976966 |
| IFIT4 | G1P2 | OASL | 0.976916 |
| OAS2 | G1P2 | MX1 | 0.976841 |
| G1P2 | IRF7 | CIG5 | 0.97684 |
| IFIT4 | OAS1 | PARP9 | 0.976808 |
| OAS1 | SAMD9L | ZBP1 | 0.976794 |
| IFIT4 | OAS3 | SAMD9L | 0.976772 |
| IFI44L | IFIT1 | XIAP | 0.97677 |
| IFI44L | IRF7 | IFIT1 | 0.976769 |
| IFIT4 | IFIT1 | ZBP1 | 0.976725 |
| G1P2 | IFI44 | SP110 | 0.976722 |
| OAS2 | OAS1 | TYKI | 0.976711 |
| IFIT5 | OAS2 | RIGE | 0.976711 |
| EPSTI1 | G1P2 | PARP9 | 0.97671 |
| IFIT5 | TYKI | SP110 | 0.976687 |
| G1P2 | OAS3 | SAMD9L | 0.976675 |
| RIG1 | IFI44 | RIGE | 0.976614 |
| IFIT4 | EPSTI1 | IFI44 | 0.976597 |
| RIG1 | OAS3 | CHMP5 | 0.976452 |
| EPSTI1 | OAS1 | SAMD9L | 0.976439 |
| RIG1 | G1P2 | CIG5 | 0.976418 |
| CIG5 | CHMP5 | MX1 | 0.976409 |
| OAS1 | IRF7 | SAMD9L | 0.976378 |
| OAS3 | HERC5 | IFIT1 | 0.976367 |
| OAS2 | IRF7 | SAMD9L | 0.976358 |
| IFIT5 | IFIT4 | G1P2 | 0.976294 |
| EPSTI1 | OAS1 | IRF7 | 0.976291 |
| IFI44 | HERC5 | SP110 | 0.976272 |
| IFI44 | OAS3 | RIGE | 0.976262 |
| IFIT4 | G1P2 | SP110 | 0.976253 |
| EPSTI1 | G1P2 | IFI44 | 0.976186 |
| OASL | IFIT1 | XIAP | 0.976181 |
| IRF7 | PARP9 | SAMD9L | 0.976177 |
| IRF7 | HERC5 | ZBP1 | 0.976154 |
| OAS3 | CHMP5 | RIGE | 0.976111 |
| OASL | TYKI | XIAP | 0.976092 |
| IFI44L | OAS2 | SAMD9L | 0.976088 |
| IFI44L | OAS1 | OASL | 0.976054 |
| IFIT1 | MX1 | SP110 | 0.976025 |
| IFI44L | HERC5 | XIAP | 0.975972 |
| IFIT5 | G1P2 | XIAP | 0.975971 |
| IFIT5 | OAS2 | SAMD9L | 0.975959 |
| IFIT5 | HERC5 | XIAP | 0.975949 |
| OASL | IFI44 | SAMD9L | 0.975842 |
| IFIT5 | EPSTI1 | PARP9 | 0.975824 |
| EPSTI1 | IFI44 | HERC5 | 0.975738 |
| SAMD9L | TYKI | RIGE | 0.975714 |
| IFI44 | OAS3 | TYKI | 0.975702 |
| IFIT5 | TYKI | RIGE | 0.97567 |
| RIG1 | CIG5 | IFIT1 | 0.975658 |
| HERC5 | PARP9 | SAMD9L | 0.975637 |
| G1P2 | OAS3 | CHMP5 | 0.975579 |
| OAS1 | HERC5 | TYKI | 0.975575 |
| IFIT5 | OASL | OAS3 | 0.975559 |
| IFI44L | IFIT4 | IFIT1 | 0.975549 |
| SAMD9L | XIAP | ZBP1 | 0.975489 |
| EPSTI1 | OASL | TYKI | 0.975407 |
| IFI44L | EPSTI1 | PARP9 | 0.975398 |
| OASL | IRF7 | IFIT1 | 0.975396 |
| RIG1 | OAS1 | CIG5 | 0.975346 |
| RIG1 | OASL | IFIT1 | 0.975344 |
| IFIT4 | OAS1 | OASL | 0.975331 |
| OAS3 | HERC5 | TYKI | 0.975303 |
| OAS1 | IFI44 | RIGE | 0.975295 |
| OAS2 | IFIT1 | MX1 | 0.97529 |
| IFIT1 | MX1 | ZBP1 | 0.975252 |
| CIG5 | MX1 | XIAP | 0.975204 |
| OAS1 | CIG5 | PARP9 | 0.97518 |
| IFIT5 | PARP9 | ZBP1 | 0.975163 |
| IFI44L | OAS1 | ZBP1 | 0.97516 |
| IFI44L | EPSTI1 | RIG1 | 0.975122 |
| IFIT4 | OASL | MX1 | 0.975118 |
| OASL | IRF7 | TYKI | 0.975116 |
| OAS2 | RIG1 | TYKI | 0.97509 |
| OAS2 | CHMP5 | XIAP | 0.975079 |
| OASL | SAMD9L | XIAP | 0.975079 |
| HERC5 | PARP9 | IFIT1 | 0.975059 |
| RIG1 | G1P2 | OAS1 | 0.975034 |
| RIG1 | OASL | IFI44 | 0.974999 |
| IFI44 | OAS3 | PARP9 | 0.974929 |
| IFIT4 | IFI44 | XIAP | 0.974925 |
| IRF7 | IFIT1 | ZBP1 | 0.974912 |
| PARP9 | SAMD9L | MX1 | 0.97489 |
| OAS1 | IFIT1 | RIGE | 0.974859 |
| EPSTI1 | SAMD9L | ZBP1 | 0.974825 |
| HERC5 | PARP9 | XIAP | 0.974823 |
| EPSTI1 | TYKI | SP110 | 0.974822 |
| IFIT4 | CIG5 | IFIT1 | 0.974778 |
| G1P2 | OAS1 | TYKI | 0.974713 |
| IFI44 | IFIT1 | SP110 | 0.974708 |
| HERC5 | PARP9 | TYKI | 0.9747 |
| EPSTI1 | G1P2 | ZBP1 | 0.974674 |
| IFI44L | OAS2 | OAS1 | 0.974667 |
| IFI44 | TYKI | ZBP1 | 0.974642 |
| EPSTI1 | CHMP5 | XIAP | 0.974537 |
| IFIT4 | SAMD9L | SP110 | 0.974501 |
| TYKI | CHMP5 | ZBP1 | 0.974475 |
| EPSTI1 | G1P2 | CIG5 | 0.974468 |
| OAS1 | IFI44 | OAS3 | 0.974458 |
| EPSTI1 | IFI44 | IFIT1 | 0.974387 |
| OAS1 | OAS3 | MX1 | 0.974382 |
| OAS2 | TYKI | XIAP | 0.974363 |
| OAS1 | OASL | HERC5 | 0.974357 |
| IFIT5 | G1P2 | IRF7 | 0.974308 |
| OAS1 | OASL | CHMP5 | 0.974297 |
| TYKI | IFIT1 | RIGE | 0.974282 |
| OAS1 | PARP9 | MX1 | 0.974256 |
| OAS2 | IFI44 | TYKI | 0.974177 |
| OAS1 | CIG5 | IFI44 | 0.974175 |
| RIG1 | IFI44 | OAS3 | 0.974125 |
| IFI44L | IFIT4 | TYKI | 0.974105 |
| OAS1 | CIG5 | CHMP5 | 0.974105 |
| OAS2 | PARP9 | SAMD9L | 0.974104 |
| IRF7 | CIG5 | MX1 | 0.974084 |
| CHMP5 | SP110 | XIAP | 0.974042 |
| EPSTI1 | CHMP5 | SP110 | 0.973988 |
| OAS1 | TYKI | XIAP | 0.973951 |
| HERC5 | CHMP5 | ZBP1 | 0.973937 |
| CIG5 | TYKI | ZBP1 | 0.973936 |
| IFI44L | SAMD9L | SP110 | 0.973933 |
| IFIT4 | HERC5 | PARP9 | 0.973933 |
| IFIT5 | OAS1 | CIG5 | 0.97391 |
| G1P2 | PARP9 | XIAP | 0.973887 |
| OAS1 | CIG5 | XIAP | 0.973886 |
| CHMP5 | MX1 | ZBP1 | 0.973864 |
| TYKI | CHMP5 | SP110 | 0.973768 |
| EPSTI1 | PARP9 | IFIT1 | 0.97373 |
| IRF7 | CHMP5 | SP110 | 0.973693 |
| CIG5 | IFI44 | PARP9 | 0.973655 |
| G1P2 | PARP9 | IFIT1 | 0.973599 |
| EPSTI1 | CIG5 | SAMD9L | 0.973586 |
| G1P2 | IRF7 | ZBP1 | 0.97357 |
| EPSTI1 | IRF7 | CHMP5 | 0.973555 |
| OASL | IFI44 | PARP9 | 0.973554 |
| OAS2 | TYKI | CHMP5 | 0.973542 |
| RIG1 | G1P2 | TYKI | 0.973532 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| IRF7 | IFI44 | XIAP | 0.973462 |
| IFIT5 | RIG1 | RIGE | 0.973451 |
| IFIT5 | IFIT4 | TYKI | 0.973442 |
| G1P2 | HERC5 | PARP9 | 0.97344 |
| OAS2 | CHMP5 | MX1 | 0.973422 |
| PARP9 | SAMD9L | TYKI | 0.973386 |
| IFI44 | MX1 | XIAP | 0.973355 |
| RIG1 | SAMD9L | TYKI | 0.973328 |
| CIG5 | CHMP5 | IFIT1 | 0.973246 |
| CIG5 | HERC5 | PARP9 | 0.973244 |
| IFI44L | IFIT4 | G1P2 | 0.973197 |
| OASL | IRF7 | HERC5 | 0.973112 |
| IFIT4 | CIG5 | CHMP5 | 0.973104 |
| OAS2 | OAS1 | SAMD9L | 0.973103 |
| G1P2 | CIG5 | CHMP5 | 0.973073 |
| RIG1 | G1P2 | SP110 | 0.973048 |
| IFIT4 | CIG5 | MX1 | 0.973006 |
| IFI44L | EPSTI1 | OAS1 | 0.973006 |
| IFIT4 | OAS3 | TYKI | 0.973003 |
| G1P2 | XIAP | ZBP1 | 0.97295 |
| OASL | PARP9 | SAMD9L | 0.972938 |
| EPSTI1 | HERC5 | PARP9 | 0.972841 |
| IFIT1 | XIAP | ZBP1 | 0.972814 |
| IFIT4 | PARP9 | IFIT1 | 0.972796 |
| CHMP5 | MX1 | SP110 | 0.972719 |
| PARP9 | TYKI | MX1 | 0.972707 |
| IFIT4 | MX1 | ZBP1 | 0.972638 |
| IFI44L | EPSTI1 | SAMD9L | 0.972539 |
| IFIT5 | IFIT1 | MX1 | 0.972533 |
| IFI44L | G1P2 | XIAP | 0.972515 |
| EPSTI1 | IFI44 | TYKI | 0.972495 |
| IFIT4 | OAS2 | HERC5 | 0.97249 |
| IFIT4 | RIG1 | XIAP | 0.97246 |
| IFIT5 | HERC5 | MX1 | 0.972458 |
| OAS1 | TYKI | SP110 | 0.972445 |
| EPSTI1 | OAS1 | CIG5 | 0.972368 |
| CIG5 | PARP9 | IFIT1 | 0.972329 |
| IFIT4 | OAS2 | G1P2 | 0.972297 |
| IFIT4 | IRF7 | IFI44 | 0.972137 |
| HERC5 | IFIT1 | RIGE | 0.97204 |
| IFI44L | PARP9 | RIGE | 0.971994 |
| RIG1 | CIG5 | MX1 | 0.971955 |
| CIG5 | IFI44 | SAMD9L | 0.971908 |
| CHMP5 | IFIT1 | ZBP1 | 0.971907 |
| CIG5 | SAMD9L | ZBP1 | 0.971889 |
| G1P2 | OAS1 | PARP9 | 0.971807 |
| IRF7 | PARP9 | IFIT1 | 0.97179 |
| OAS3 | TYKI | MX1 | 0.971782 |
| OAS2 | HERC5 | CHMP5 | 0.97176 |
| IRF7 | HERC5 | PARP9 | 0.971671 |
| IFIT4 | G1P2 | PARP9 | 0.971625 |
| EPSTI1 | TYKI | CHMP5 | 0.971602 |
| IRF7 | IFI44 | MX1 | 0.971595 |
| OAS1 | OASL | SAMD9L | 0.971575 |
| IFIT4 | OAS2 | CHMP5 | 0.971528 |
| IFI44L | G1P2 | IRF7 | 0.971506 |
| OAS1 | HERC5 | SP110 | 0.971466 |
| RIG1 | OASL | TYKI | 0.971392 |
| IRF7 | PARP9 | TYKI | 0.971348 |
| IFIT4 | OAS1 | OAS3 | 0.971335 |
| G1P2 | CHMP5 | ZBP1 | 0.971335 |
| IFIT4 | HERC5 | SP110 | 0.971301 |
| IFI44 | TYKI | SP110 | 0.971298 |
| OAS2 | IRF7 | HERC5 | 0.97127 |
| IFIT4 | OAS2 | IFIT1 | 0.971233 |
| IFI44L | PARP9 | SP110 | 0.971191 |
| IFIT5 | OAS1 | OAS3 | 0.971185 |
| OAS2 | IRF7 | IFIT1 | 0.971184 |
| OAS2 | IFI44 | PARP9 | 0.971174 |
| IFI44L | PARP9 | ZBP1 | 0.971145 |
| G1P2 | CHMP5 | SP110 | 0.971088 |
| OAS1 | HERC5 | SAMD9L | 0.971083 |
| G1P2 | CIG5 | PARP9 | 0.971042 |
| IFIT5 | PARP9 | XIAP | 0.971027 |
| EPSTI1 | CHMP5 | MX1 | 0.970954 |
| G1P2 | SP110 | XIAP | 0.970897 |
| OASL | HERC5 | XIAP | 0.970881 |
| RIG1 | IFIT1 | ZBP1 | 0.97081 |
| G1P2 | OASL | XIAP | 0.970803 |
| OAS2 | PARP9 | TYKI | 0.970766 |
| IFI44L | IFIT4 | OAS1 | 0.970742 |
| IFIT5 | G1P2 | MX1 | 0.970738 |
| EPSTI1 | CIG5 | HERC5 | 0.970734 |
| EPSTI1 | OAS1 | PARP9 | 0.970723 |
| HERC5 | TYKI | RIGE | 0.970716 |
| OAS1 | OAS3 | HERC5 | 0.970715 |
| G1P2 | IFIT1 | RIGE | 0.970712 |
| IFIT4 | IRF7 | XIAP | 0.970712 |
| HERC5 | CHMP5 | SP110 | 0.970697 |
| IFI44L | OAS3 | RIGE | 0.970693 |
| RIG1 | CIG5 | IFI44 | 0.970657 |
| EPSTI1 | OASL | SAMD9L | 0.970657 |
| RIG1 | G1P2 | ZBP1 | 0.970629 |
| RIG1 | HERC5 | ZBP1 | 0.970593 |
| IFI44 | SAMD9L | ZBP1 | 0.970587 |
| OAS1 | IRF7 | XIAP | 0.970567 |
| IFIT4 | IFI44 | MX1 | 0.970564 |
| OAS1 | OASL | TYKI | 0.970536 |
| OAS1 | OASL | IFI44 | 0.970435 |
| OAS1 | OAS3 | SAMD9L | 0.970395 |
| OAS1 | IRF7 | ZBP1 | 0.970393 |
| IFI44L | TYKI | XIAP | 0.970382 |
| HERC5 | XIAP | ZBP1 | 0.970322 |
| OAS2 | CHMP5 | IFIT1 | 0.970286 |
| EPSTI1 | OAS1 | XIAP | 0.970174 |
| IFI44L | IRF7 | TYKI | 0.970096 |
| IFI44L | HERC5 | MX1 | 0.970092 |
| PARP9 | MX1 | XIAP | 0.970089 |
| IFIT5 | EPSTI1 | RIG1 | 0.970015 |
| IFIT5 | IFIT4 | PARP9 | 0.97001 |
| G1P2 | OAS3 | IFIT1 | 0.96993 |
| OAS3 | HERC5 | MX1 | 0.969845 |
| OASL | MX1 | XIAP | 0.969812 |
| OAS1 | IFI44 | ZBP1 | 0.969803 |
| G1P2 | HERC5 | RIGE | 0.969762 |
| IFIT5 | PARP9 | SP110 | 0.969753 |
| G1P2 | OAS3 | HERC5 | 0.969712 |
| OAS1 | MX1 | RIGE | 0.969615 |
| HERC5 | PARP9 | MX1 | 0.969607 |
| IFI44 | IFIT1 | XIAP | 0.969589 |
| RIG1 | OASL | HERC5 | 0.969589 |
| CIG5 | TYKI | SP110 | 0.969581 |
| G1P2 | IRF7 | SP110 | 0.969568 |
| IFIT5 | IFI44L | RIGE | 0.969542 |
| IFI44 | HERC5 | XIAP | 0.96949 |
| RIG1 | IFI44 | ZBP1 | 0.969468 |
| IFIT5 | HERC5 | IFIT1 | 0.969441 |
| IRF7 | IFI44 | HERC5 | 0.96943 |
| RIG1 | OAS1 | HERC5 | 0.969339 |
| IFIT5 | TYKI | XIAP | 0.969273 |
| EPSTI1 | G1P2 | OASL | 0.969257 |
| IFIT5 | G1P2 | IFIT1 | 0.969226 |
| TYKI | MX1 | RIGE | 0.969116 |
| OAS3 | PARP9 | CHMP5 | 0.969112 |
| EPSTI1 | G1P2 | CHMP5 | 0.96899 |
| IFIT4 | SAMD9L | RIGE | 0.968926 |
| IFIT4 | OAS1 | SP110 | 0.968908 |
| OAS2 | CIG5 | TYKI | 0.968886 |
| EPSTI1 | CIG5 | IFIT1 | 0.968832 |
| IFIT4 | RIG1 | IRF7 | 0.968749 |
| OASL | IRF7 | MX1 | 0.968693 |
| IFIT4 | IFIT1 | SP110 | 0.968688 |
| OAS2 | OAS1 | IFI44 | 0.968687 |
| OAS2 | RIG1 | SAMD9L | 0.968678 |
| IFIT5 | EPSTI1 | SAMD9L | 0.968673 |
| OAS1 | CHMP5 | ZBP1 | 0.968667 |
| IFI44L | OAS1 | SP110 | 0.968637 |
| EPSTI1 | RIG1 | OAS1 | 0.968633 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| G1P2 | OAS1 | OAS3 | 0.968589 |
| IFIT4 | IFI44 | HERC5 | 0.968562 |
| IFI44 | PARP9 | RIGE | 0.96854 |
| IRF7 | SAMD9L | SP110 | 0.96853 |
| OASL | CIG5 | TYKI | 0.968523 |
| EPSTI1 | HERC5 | CHMP5 | 0.96846 |
| OAS2 | G1P2 | CHMP5 | 0.968446 |
| IRF7 | OAS3 | SAMD9L | 0.968439 |
| G1P2 | OASL | IRF7 | 0.968413 |
| EPSTI1 | OASL | IFIT1 | 0.968391 |
| IFIT4 | OAS3 | HERC5 | 0.968353 |
| IFIT5 | IRF7 | TYKI | 0.968333 |
| RIG1 | OAS1 | IRF7 | 0.968329 |
| EPSTI1 | IFIT1 | ZBP1 | 0.968297 |
| OASL | CIG5 | SAMD9L | 0.968278 |
| IRF7 | MX1 | ZBP1 | 0.968177 |
| OAS1 | HERC5 | PARP9 | 0.968172 |
| G1P2 | PARP9 | TYKI | 0.968154 |
| CHMP5 | IFIT1 | SP110 | 0.968058 |
| IFIT4 | CHMP5 | SP110 | 0.968014 |
| IFI44L | IFIT1 | MX1 | 0.967969 |
| IFIT4 | OAS2 | MX1 | 0.967961 |
| IRF7 | CHMP5 | XIAP | 0.967909 |
| IFIT5 | OAS1 | ZBP1 | 0.967889 |
| IRF7 | IFI44 | IFIT1 | 0.967883 |
| IFI44L | HERC5 | IFIT1 | 0.967852 |
| OAS2 | IFI44 | SAMD9L | 0.967841 |
| OAS2 | G1P2 | IRF7 | 0.967815 |
| EPSTI1 | PARP9 | MX1 | 0.967795 |
| EPSTI1 | HERC5 | ZBP1 | 0.967772 |
| OASL | PARP9 | CHMP5 | 0.967676 |
| G1P2 | IFI44 | XIAP | 0.967671 |
| PARP9 | SAMD9L | ZBP1 | 0.967633 |
| IFIT5 | TYKI | MX1 | 0.967584 |
| OAS2 | EPSTI1 | G1P2 | 0.967581 |
| IFIT4 | OAS3 | IFIT1 | 0.967551 |
| IFIT5 | OAS2 | OAS1 | 0.967489 |
| IFIT5 | IFI44L | OAS3 | 0.967466 |
| OAS3 | IFIT1 | MX1 | 0.967409 |
| IFIT5 | SAMD9L | SP110 | 0.967392 |
| IFIT4 | PARP9 | MX1 | 0.967359 |
| EPSTI1 | OAS1 | ZBP1 | 0.967286 |
| IFIT5 | PARP9 | RIGE | 0.967265 |
| OAS1 | SAMD9L | XIAP | 0.967252 |
| PARP9 | IFIT1 | MX1 | 0.967202 |
| OASL | PARP9 | IFIT1 | 0.967188 |
| IFIT4 | PARP9 | XIAP | 0.967184 |
| G1P2 | OAS1 | RIGE | 0.967087 |
| IFI44L | PARP9 | XIAP | 0.967006 |
| IRF7 | HERC5 | SP110 | 0.966994 |
| IFIT5 | G1P2 | HERC5 | 0.96692 |
| IFI44L | IFIT4 | SAMD9L | 0.966918 |
| EPSTI1 | G1P2 | SP110 | 0.966913 |
| IFIT4 | EPSTI1 | CHMP5 | 0.966844 |
| OAS2 | OAS1 | CHMP5 | 0.966812 |
| EPSTI1 | IFI44 | PARP9 | 0.966774 |
| IFIT4 | IFI44 | IFIT1 | 0.966763 |
| CIG5 | SAMD9L | CHMP5 | 0.966661 |
| IFI44L | IFIT4 | PARP9 | 0.966617 |
| IFIT5 | RIG1 | SP110 | 0.966575 |
| EPSTI1 | CIG5 | MX1 | 0.966555 |
| EPSTI1 | CHMP5 | IFIT1 | 0.966528 |
| OAS2 | IFIT1 | XIAP | 0.966404 |
| MX1 | XIAP | ZBP1 | 0.966334 |
| HERC5 | MX1 | RIGE | 0.966315 |
| IFIT5 | OAS1 | RIGE | 0.966293 |
| G1P2 | PARP9 | MX1 | 0.966277 |
| IFI44L | TYKI | MX1 | 0.96627 |
| IFI44 | PARP9 | ZBP1 | 0.966234 |
| OAS1 | CIG5 | ZBP1 | 0.966217 |
| IFIT4 | G1P2 | IFI44 | 0.966203 |
| IFIT4 | MX1 | SP110 | 0.966196 |
| OAS2 | OAS1 | IRF7 | 0.966139 |
| IFIT4 | CHMP5 | XIAP | 0.966104 |
| IFIT5 | IFIT4 | SAMD9L | 0.966044 |
| RIG1 | OAS1 | MX1 | 0.966034 |
| IFIT5 | IRF7 | PARP9 | 0.96594 |
| G1P2 | IRF7 | PARP9 | 0.965876 |
| OAS2 | RIG1 | IFI44 | 0.965818 |
| IFI44L | G1P2 | MX1 | 0.96579 |
| IRF7 | IFIT1 | SP110 | 0.965745 |
| OAS2 | EPSTI1 | SAMD9L | 0.965666 |
| CHMP5 | MX1 | XIAP | 0.965604 |
| OAS2 | PARP9 | IFIT1 | 0.965491 |
| EPSTI1 | OAS1 | IFI44 | 0.96548 |
| OAS2 | IRF7 | MX1 | 0.965404 |
| OAS1 | SAMD9L | RIGE | 0.965336 |
| IFIT1 | SP110 | XIAP | 0.965321 |
| RIG1 | G1P2 | OASL | 0.965315 |
| IFI44L | OAS1 | MX1 | 0.965307 |
| G1P2 | IRF7 | IFI44 | 0.965102 |
| IFIT5 | TYKI | IFIT1 | 0.965094 |
| IFI44L | G1P2 | HERC5 | 0.965057 |
| IFI44L | G1P2 | IFIT1 | 0.965022 |
| IFIT5 | SP110 | RIGE | 0.965009 |
| EPSTI1 | OASL | HERC5 | 0.964998 |
| OAS2 | RIG1 | IFIT1 | 0.964968 |
| IFI44L | IRF7 | SAMD9L | 0.964937 |
| OAS3 | PARP9 | SAMD9L | 0.964908 |
| IFIT4 | IFI44 | TYKI | 0.964883 |
| PARP9 | TYKI | SP110 | 0.964876 |
| IFIT5 | IFIT4 | RIG1 | 0.964868 |
| EPSTI1 | OAS3 | TYKI | 0.964834 |
| IFI44L | IFIT4 | RIG1 | 0.964794 |
| IFIT1 | MX1 | RIGE | 0.96478 |
| OAS2 | SAMD9L | XIAP | 0.964778 |
| IFIT5 | IFIT4 | OAS1 | 0.964745 |
| OASL | PARP9 | TYKI | 0.96474 |
| OAS1 | SAMD9L | TYKI | 0.964718 |
| EPSTI1 | OAS3 | SAMD9L | 0.964666 |
| CIG5 | PARP9 | MX1 | 0.96462 |
| OAS2 | G1P2 | XIAP | 0.964584 |
| G1P2 | TYKI | RIGE | 0.964575 |
| OAS1 | OAS3 | TYKI | 0.964457 |
| SAMD9L | CHMP5 | ZBP1 | 0.964434 |
| IFI44L | TYKI | IFIT1 | 0.964427 |
| G1P2 | OAS3 | TYKI | 0.964415 |
| IFIT4 | TYKI | RIGE | 0.964415 |
| IFIT5 | PARP9 | IFIT1 | 0.964404 |
| IFI44 | HERC5 | MX1 | 0.964284 |
| IFI44L | OAS1 | IRF7 | 0.964253 |
| OAS1 | IRF7 | PARP9 | 0.964194 |
| IFIT5 | OASL | RIGE | 0.964094 |
| IFIT5 | PARP9 | MX1 | 0.963954 |
| G1P2 | CIG5 | ZBP1 | 0.963938 |
| IFIT5 | OAS1 | OASL | 0.963852 |
| IRF7 | CHMP5 | MX1 | 0.963787 |
| IFIT5 | EPSTI1 | OAS1 | 0.963774 |
| OAS1 | PARP9 | XIAP | 0.963475 |
| OAS1 | HERC5 | RIGE | 0.963465 |
| EPSTI1 | MX1 | ZBP1 | 0.963452 |
| EPSTI1 | OASL | MX1 | 0.963447 |
| IRF7 | PARP9 | MX1 | 0.963413 |
| IFI44 | TYKI | XIAP | 0.963301 |
| G1P2 | MX1 | RIGE | 0.96322 |
| EPSTI1 | IFI44 | SAMD9L | 0.963203 |
| OAS1 | PARP9 | SAMD9L | 0.963196 |
| IFI44L | OAS1 | IFIT1 | 0.963135 |
| IFI44L | IRF7 | PARP9 | 0.963058 |
| OAS1 | SAMD9L | SP110 | 0.963012 |
| IFIT5 | IRF7 | SAMD9L | 0.963 |
| EPSTI1 | OAS1 | CHMP5 | 0.962935 |
| IFIT4 | IRF7 | CHMP5 | 0.962925 |
| IFIT4 | EPSTI1 | XIAP | 0.96284 |
| CIG5 | HERC5 | ZBP1 | 0.962817 |
| PARP9 | TYKI | ZBP1 | 0.96278 |
| OASL | CIG5 | IFIT1 | 0.962747 |
| OAS1 | PARP9 | TYKI | 0.962615 |

TABLE 4B-continued

All possible 3-gene combinations of a selected group of 24 genes, indicated with their respective Pearson correlation values.

| Gene 1 | Gene 2 | Gene 3 | Pearson Correlation |
| --- | --- | --- | --- |
| IFI44L | HERC5 | TYKI | 0.962603 |
| OAS2 | EPSTI1 | IFIT1 | 0.962552 |
| CIG5 | PARP9 | CHMP5 | 0.962508 |
| IFI44L | RIG1 | IRF7 | 0.962495 |
| IFI44L | SAMD9L | XIAP | 0.962462 |
| IFI44L | IFI44 | RIGE | 0.9624 |
| IRF7 | HERC5 | CHMP5 | 0.962383 |
| OASL | SAMD9L | ZBP1 | 0.962363 |
| OAS2 | CIG5 | SAMD9L | 0.962348 |
| OAS2 | RIG1 | HERC5 | 0.962318 |
| OAS2 | HERC5 | XIAP | 0.962291 |
| IFIT5 | SAMD9L | MX1 | 0.962201 |
| CIG5 | IFIT1 | ZBP1 | 0.962115 |
| HERC5 | SP110 | XIAP | 0.962086 |
| RIG1 | IFIT1 | SP110 | 0.962019 |
| OAS2 | OAS1 | PARP9 | 0.962018 |
| RIG1 | CIG5 | CHMP5 | 0.961991 |
| IFI44 | IFIT1 | MX1 | 0.961953 |
| IFIT5 | OAS1 | MX1 | 0.961952 |
| HERC5 | CHMP5 | XIAP | 0.961934 |
| RIG1 | HERC5 | SP110 | 0.961903 |
| OAS3 | SAMD9L | XIAP | 0.961841 |
| RIG1 | SAMD9L | SP110 | 0.961804 |
| CHMP5 | IFIT1 | XIAP | 0.961773 |
| G1P2 | OAS3 | MX1 | 0.961665 |
| TYKI | CHMP5 | XIAP | 0.961658 |
| TYKI | SP110 | ZBP1 | 0.961568 |
| OAS2 | HERC5 | PARP9 | 0.961517 |
| G1P2 | IFI44 | MX1 | 0.961483 |
| IFIT4 | OAS1 | IFI44 | 0.961474 |
| IRF7 | IFI44 | TYKI | 0.961401 |
| IFI44L | RIG1 | XIAP | 0.961392 |
| SAMD9L | SP110 | XIAP | 0.961343 |
| PARP9 | SAMD9L | SP110 | 0.961334 |
| IFIT5 | IFI44L | OASL | 0.961265 |
| OAS2 | G1P2 | PARP9 | 0.961245 |
| OASL | HERC5 | PARP9 | 0.961238 |
| RIG1 | MX1 | ZBP1 | 0.96122 |
| OAS2 | RIG1 | G1P2 | 0.961201 |
| IRF7 | OAS3 | IFIT1 | 0.961186 |
| OAS2 | EPSTI1 | OAS1 | 0.96115 |
| IFI44 | SAMD9L | SP110 | 0.961138 |
| OAS1 | XIAP | ZBP1 | 0.961114 |
| IFIT4 | G1P2 | OAS3 | 0.961085 |
| IFIT5 | RIG1 | XIAP | 0.961054 |
| IFIT5 | SAMD9L | XIAP | 0.961053 |
| IFI44 | HERC5 | IFIT1 | 0.960963 |
| IFIT5 | RIG1 | IRF7 | 0.96093 |
| IFI44L | CHMP5 | RIGE | 0.960881 |
| IFIT4 | OAS3 | MX1 | 0.960838 |
| IFIT5 | OAS3 | RIGE | 0.960806 |
| OAS2 | EPSTI1 | HERC5 | 0.960756 |
| OAS2 | MX1 | XIAP | 0.960748 |
| IFIT4 | TYKI | CHMP5 | 0.960741 |
| EPSTI1 | RIG1 | IFI44 | 0.960722 |
| IFIT5 | HERC5 | TYKI | 0.960702 |
| OASL | CIG5 | HERC5 | 0.960689 |
| IFI44L | SAMD9L | MX1 | 0.960664 |
| IFIT5 | IFI44L | CIG5 | 0.960571 |
| IFIT4 | EPSTI1 | IRF7 | 0.960461 |
| IRF7 | MX1 | SP110 | 0.96046 |
| IFI44L | OAS1 | XIAP | 0.960455 |
| IFIT5 | CHMP5 | RIGE | 0.960416 |
| IFIT5 | IFI44 | RIGE | 0.960385 |
| IFIT5 | RIG1 | MX1 | 0.960368 |
| MX1 | SP110 | XIAP | 0.960338 |
| IRF7 | OAS3 | HERC5 | 0.960332 |
| IRF7 | OAS3 | TYKI | 0.960205 |
| IFI44 | PARP9 | SP110 | 0.960125 |
| OASL | TYKI | ZBP1 | 0.960125 |
| IRF7 | CHMP5 | IFIT1 | 0.960021 |
| OAS2 | SAMD9L | CHMP5 | 0.959993 |
| G1P2 | IFI44 | HERC5 | 0.959978 |
| IFIT4 | CHMP5 | MX1 | 0.959927 |
| IFI44 | TYKI | MX1 | 0.959842 |
| G1P2 | OASL | CIG5 | 0.959832 |
| IFIT4 | CIG5 | XIAP | 0.959816 |
| IFIT4 | OAS1 | RIGE | 0.959814 |
| OAS2 | TYKI | ZBP1 | 0.959811 |
| IRF7 | TYKI | CHMP5 | 0.959787 |
| OAS3 | IFIT1 | XIAP | 0.959775 |
| OAS2 | OAS1 | CIG5 | 0.959672 |
| G1P2 | CHMP5 | XIAP | 0.959471 |
| G1P2 | IFI44 | IFIT1 | 0.959467 |
| IFI44L | PARP9 | IFIT1 | 0.959464 |
| G1P2 | OASL | PARP9 | 0.959415 |
| IFIT5 | HERC5 | PARP9 | 0.959387 |
| OAS1 | OASL | IRF7 | 0.959375 |
| OAS1 | IFI44 | SP110 | 0.959304 |
| IFI44 | PARP9 | XIAP | 0.959285 |
| IFIT5 | OAS1 | IFIT1 | 0.959283 |
| PARP9 | CHMP5 | RIGE | 0.959251 |
| OAS3 | TYKI | XIAP | 0.959059 |
| IFIT5 | IFI44 | OAS3 | 0.959005 |
| IFIT5 | OAS3 | CHMP5 | 0.959002 |
| RIG1 | CHMP5 | ZBP1 | 0.958994 |
| IFIT4 | IFIT1 | RIGE | 0.958926 |
| EPSTI1 | PARP9 | XIAP | 0.958805 |
| RIG1 | OAS1 | ZBP1 | 0.958689 |
| OAS1 | IFI44 | MX1 | 0.958663 |
| EPSTI1 | OAS3 | IFIT1 | 0.958634 |
| IFIT5 | G1P2 | PARP9 | 0.95861 |
| OAS2 | EPSTI1 | MX1 | 0.958508 |
| PARP9 | IFIT1 | ZBP1 | 0.958503 |
| IFIT4 | HERC5 | CHMP5 | 0.958451 |
| G1P2 | CIG5 | SP110 | 0.958403 |
| IFI44L | PARP9 | MX1 | 0.958264 |
| OAS1 | CHMP5 | SP110 | 0.95826 |
| G1P2 | PARP9 | SP110 | 0.958153 |
| OAS1 | TYKI | RIGE | 0.958151 |
| IFIT4 | HERC5 | RIGE | 0.958132 |
| RIG1 | OAS1 | TYKI | 0.958104 |
| IFIT4 | IRF7 | PARP9 | 0.958024 |
| IFIT4 | EPSTI1 | PARP9 | 0.957986 |
| IFIT5 | SAMD9L | IFIT1 | 0.957766 |
| RIG1 | IRF7 | XIAP | 0.957764 |
| CIG5 | SAMD9L | SP110 | 0.957721 |
| IFI44L | IFI44 | OAS3 | 0.957601 |
| IFIT5 | G1P2 | TYKI | 0.9576 |
| IFI44L | HERC5 | PARP9 | 0.957553 |
| RIG1 | OAS3 | SAMD9L | 0.957356 |
| EPSTI1 | OAS1 | OASL | 0.957294 |
| IFIT4 | XIAP | ZBP1 | 0.95721 |
| IFI44L | SAMD9L | IFIT1 | 0.957107 |
| IFI44L | G1P2 | TYKI | 0.957049 |
| OAS2 | RIG1 | MX1 | 0.957032 |
| IFI44 | TYKI | IFIT1 | 0.957022 |
| CIG5 | PARP9 | XIAP | 0.957014 |
| IFIT4 | IRF7 | ZBP1 | 0.956993 |
| IFI44L | G1P2 | OAS1 | 0.956925 |
| OAS1 | OASL | CIG5 | 0.956894 |
| IFIT4 | IFI44 | PARP9 | 0.95689 |
| EPSTI1 | OAS3 | HERC5 | 0.956754 |
| IFIT4 | G1P2 | RIGE | 0.956716 |
| IFIT4 | IRF7 | CIG5 | 0.956703 |
| IFIT4 | OAS1 | CHMP5 | 0.956662 |
| IFI44L | OAS1 | HERC5 | 0.956626 |
| G1P2 | IRF7 | CHMP5 | 0.956597 |
| IFIT4 | IFI44 | SAMD9L | 0.956274 |
| IFIT5 | IFI44L | ZBP1 | 0.956233 |
| IFI44L | RIG1 | MX1 | 0.956172 |
| IFIT4 | CHMP5 | IFIT1 | 0.95615 |
| IFIT5 | OAS1 | IRF7 | 0.956078 |
| OASL | CIG5 | MX1 | 0.956076 |
| OASL | IFIT1 | ZBP1 | 0.956072 |
| OAS2 | G1P2 | CIG5 | 0.956019 |
| OAS2 | PARP9 | CHMP5 | 0.956009 |
| G1P2 | PARP9 | ZBP1 | 0.955951 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| OAS2 | OASL | TYKI | 0.955901 |
| OAS1 | IRF7 | IFI44 | 0.955882 |
| IFI44 | HERC5 | TYKI | 0.955752 |
| OAS3 | HERC5 | XIAP | 0.955729 |
| RIG1 | PARP9 | IFIT1 | 0.955722 |
| OAS2 | CIG5 | IFIT1 | 0.955705 |
| IFIT4 | OASL | XIAP | 0.955698 |
| IFIT4 | CIG5 | PARP9 | 0.955687 |
| OASL | PARP9 | MX1 | 0.955668 |
| PARP9 | IFIT1 | SP110 | 0.955597 |
| IFIT4 | EPSTI1 | RIG1 | 0.95557 |
| EPSTI1 | OAS1 | OAS3 | 0.955534 |
| OAS2 | TYKI | SP110 | 0.955523 |
| IFIT4 | G1P2 | CHMP5 | 0.955509 |
| OAS1 | IFI44 | IFIT1 | 0.955489 |
| IFIT5 | IFI44L | OAS2 | 0.955474 |
| RIG1 | IFI44 | SP110 | 0.955462 |
| IFIT5 | G1P2 | SAMD9L | 0.955415 |
| RIG1 | MX1 | SP110 | 0.955384 |
| CIG5 | MX1 | ZBP1 | 0.955366 |
| IFI44L | HERC5 | SAMD9L | 0.955348 |
| EPSTI1 | SAMD9L | CHMP5 | 0.955332 |
| RIG1 | OAS1 | XIAP | 0.955331 |
| EPSTI1 | IRF7 | XIAP | 0.95532 |
| IFIT5 | RIG1 | IFIT1 | 0.955282 |
| EPSTI1 | SAMD9L | SP110 | 0.955279 |
| EPSTI1 | G1P2 | OAS3 | 0.955231 |
| OAS2 | CIG5 | HERC5 | 0.955226 |
| TYKI | CHMP5 | MX1 | 0.955217 |
| IFI44L | OAS3 | CHMP5 | 0.955174 |
| SAMD9L | RIGE | XIAP | 0.955155 |
| OAS3 | PARP9 | IFIT1 | 0.955055 |
| RIG1 | PARP9 | SAMD9L | 0.955049 |
| HERC5 | PARP9 | ZBP1 | 0.954901 |
| OAS2 | SAMD9L | ZBP1 | 0.954865 |
| EPSTI1 | IFIT1 | SP110 | 0.954814 |
| IFIT5 | OAS1 | SP110 | 0.954676 |
| OAS1 | PARP9 | ZBP1 | 0.954667 |
| SAMD9L | CHMP5 | SP110 | 0.954657 |
| IFI44L | G1P2 | SAMD9L | 0.954671 |
| IRF7 | PARP9 | XIAP | 0.954463 |
| CIG5 | OAS3 | SAMD9L | 0.95446 |
| OAS1 | IRF7 | OAS3 | 0.954415 |
| HERC5 | CHMP5 | MX1 | 0.954364 |
| OAS1 | IFI44 | XIAP | 0.954344 |
| IRF7 | IFI44 | SAMD9L | 0.954318 |
| OAS1 | OASL | XIAP | 0.954263 |
| IFI44L | OASL | IFI44 | 0.954204 |
| IFI44 | SAMD9L | XIAP | 0.954127 |
| OAS2 | PARP9 | MX1 | 0.9541 |
| OAS1 | CHMP5 | MX1 | 0.95402 |
| OAS2 | OASL | SAMD9L | 0.953851 |
| IRF7 | IFI44 | PARP9 | 0.953769 |
| OAS2 | OAS1 | XIAP | 0.953577 |
| IFI44L | G1P2 | PARP9 | 0.953542 |
| EPSTI1 | HERC5 | SP110 | 0.953434 |
| IRF7 | SAMD9L | RIGE | 0.953308 |
| EPSTI1 | PARP9 | CHMP5 | 0.953256 |
| OAS1 | IRF7 | CHMP5 | 0.953118 |
| IFIT5 | HERC5 | SAMD9L | 0.95311 |
| IFIT5 | G1P2 | OAS1 | 0.953008 |
| IFI44 | SAMD9L | MX1 | 0.952969 |
| IFIT5 | OAS1 | XIAP | 0.952878 |
| IFIT4 | MX1 | RIGE | 0.952876 |
| IFI44L | RIG1 | IFIT1 | 0.952657 |
| CIG5 | HERC5 | SP110 | 0.95255 |
| IFIT4 | OASL | IRF7 | 0.952437 |
| IFIT5 | PARP9 | TYKI | 0.952387 |
| OAS1 | OASL | PARP9 | 0.952351 |
| IFIT5 | OASL | IFI44 | 0.952334 |
| TYKI | CHMP5 | IFIT1 | 0.952291 |
| EPSTI1 | IRF7 | PARP9 | 0.95219 |
| IRF7 | CIG5 | XIAP | 0.952171 |
| IFIT1 | RIGE | XIAP | 0.952097 |
| CIG5 | IFIT1 | SP110 | 0.952015 |
| G1P2 | OASL | ZBP1 | 0.951985 |
| EPSTI1 | RIG1 | IRF7 | 0.951946 |
| IFI44L | PARP9 | TYKI | 0.951921 |
| IFI44 | PARP9 | MX1 | 0.951919 |
| OAS3 | PARP9 | TYKI | 0.951916 |
| CIG5 | OAS3 | TYKI | 0.951891 |
| G1P2 | IFI44 | TYKI | 0.951838 |
| OAS2 | RIG1 | CHMP5 | 0.951825 |
| EPSTI1 | TYKI | RIGE | 0.951667 |
| RIG1 | PARP9 | TYKI | 0.951655 |
| HERC5 | PARP9 | SP110 | 0.951639 |
| IFIT4 | RIG1 | ZBP1 | 0.951613 |
| RIG1 | HERC5 | PARP9 | 0.951503 |
| G1P2 | OAS1 | IFI44 | 0.951439 |
| IRF7 | OAS3 | MX1 | 0.951423 |
| IFI44 | PARP9 | IFIT1 | 0.95141 |
| CHMP5 | IFIT1 | MX1 | 0.951388 |
| EPSTI1 | MX1 | SP110 | 0.951254 |
| OAS2 | RIG1 | OAS1 | 0.951245 |
| IFI44L | RIG1 | HERC5 | 0.951245 |
| IFIT5 | CIG5 | IFI44 | 0.951244 |
| TYKI | RIGE | XIAP | 0.951171 |
| EPSTI1 | SAMD9L | RIGE | 0.951147 |
| HERC5 | TYKI | CHMP5 | 0.951145 |
| EPSTI1 | OAS3 | MX1 | 0.951138 |
| HERC5 | CHMP5 | IFIT1 | 0.951107 |
| IFI44L | CIG5 | IFI44 | 0.951044 |
| IFI44L | OASL | CHMP5 | 0.951043 |
| G1P2 | SP110 | ZBP1 | 0.951027 |
| SAMD9L | SP110 | ZBP1 | 0.95089 |
| G1P2 | CHMP5 | MX1 | 0.950868 |
| OAS2 | OASL | IFIT1 | 0.950862 |
| PARP9 | CHMP5 | ZBP1 | 0.950852 |
| OAS3 | HERC5 | PARP9 | 0.95078 |
| EPSTI1 | RIG1 | XIAP | 0.950771 |
| OASL | TYKI | SP110 | 0.950742 |
| IFIT4 | RIG1 | CIG5 | 0.950667 |
| OAS1 | IRF7 | SP110 | 0.950651 |
| OAS1 | CHMP5 | IFIT1 | 0.950645 |
| IFIT5 | IFI44L | EPSTI1 | 0.950585 |
| IFIT5 | OASL | CHMP5 | 0.950564 |
| OAS1 | CHMP5 | XIAP | 0.950413 |
| OAS3 | MX1 | XIAP | 0.950368 |
| OASL | HERC5 | ZBP1 | 0.950235 |
| IFI44 | HERC5 | PARP9 | 0.950187 |
| OAS1 | IFI44 | HERC5 | 0.95016 |
| RIG1 | OAS1 | SAMD9L | 0.950071 |
| G1P2 | HERC5 | CHMP5 | 0.949965 |
| RIG1 | OAS3 | IFIT1 | 0.9499 |
| IRF7 | CIG5 | PARP9 | 0.949776 |
| IFI44L | SAMD9L | TYKI | 0.949773 |
| IFI44 | CHMP5 | RIGE | 0.949687 |
| G1P2 | OAS3 | XIAP | 0.949642 |
| OAS1 | CIG5 | SP110 | 0.949578 |
| OAS2 | CIG5 | MX1 | 0.949555 |
| IFIT5 | OAS1 | HERC5 | 0.949513 |
| OAS1 | OAS3 | PARP9 | 0.94951 |
| G1P2 | IRF7 | OAS3 | 0.949402 |
| G1P2 | CHMP5 | IFIT1 | 0.949251 |
| IFIT5 | RIG1 | HERC5 | 0.948959 |
| IFIT4 | RIG1 | IFI44 | 0.948886 |
| IFI44L | OAS1 | TYKI | 0.948871 |
| RIG1 | IFI44 | XIAP | 0.94863 |
| IFIT5 | PARP9 | SAMD9L | 0.948596 |
| IFI44 | SAMD9L | IFIT1 | 0.948585 |
| IFIT4 | OASL | PARP9 | 0.948562 |
| IFIT4 | EPSTI1 | ZBP1 | 0.948539 |
| IFIT5 | RIG1 | G1P2 | 0.948086 |
| OAS1 | CIG5 | OAS3 | 0.947983 |
| G1P2 | IFI44 | PARP9 | 0.947968 |
| IFIT5 | IFI44L | SP110 | 0.947938 |
| EPSTI1 | CIG5 | PARP9 | 0.947921 |
| EPSTI1 | RIG1 | CHMP5 | 0.947831 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| IFIT5 | IFI44 | ZBP1 | 0.947787 |
| IFIT4 | PARP9 | SAMD9L | 0.947734 |
| G1P2 | IFI44 | SAMD9L | 0.947721 |
| IFI44L | OAS1 | PARP9 | 0.947446 |
| IFI44 | HERC5 | SAMD9L | 0.947347 |
| OAS2 | IFIT1 | ZBP1 | 0.947303 |
| IFIT4 | EPSTI1 | CIG5 | 0.947143 |
| RIG1 | G1P2 | PARP9 | 0.947042 |
| IFIT4 | RIG1 | OASL | 0.946997 |
| OAS2 | G1P2 | ZBP1 | 0.946916 |
| CIG5 | OAS3 | IFIT1 | 0.946822 |
| G1P2 | RIGE | XIAP | 0.946802 |
| OAS1 | OAS3 | XIAP | 0.946769 |
| IFIT5 | SAMD9L | TYKI | 0.946742 |
| RIG1 | CIG5 | XIAP | 0.946738 |
| CIG5 | SAMD9L | RIGE | 0.946558 |
| IRF7 | IFIT1 | RIGE | 0.946462 |
| IFI44L | IFI44 | ZBP1 | 0.946452 |
| PARP9 | MX1 | ZBP1 | 0.946362 |
| IFIT5 | OAS2 | IFI44 | 0.946333 |
| EPSTI1 | G1P2 | RIGE | 0.946322 |
| HERC5 | RIGE | XIAP | 0.946188 |
| CIG5 | MX1 | SP110 | 0.946153 |
| RIG1 | SAMD9L | RIGE | 0.946083 |
| RIG1 | IRF7 | IFI44 | 0.946068 |
| IRF7 | SAMD9L | CHMP5 | 0.946026 |
| G1P2 | TYKI | CHMP5 | 0.945734 |
| RIG1 | OAS3 | HERC5 | 0.945918 |
| RIG1 | IRF7 | CIG5 | 0.945803 |
| OASL | MX1 | ZBP1 | 0.945774 |
| G1P2 | OAS1 | CHMP5 | 0.945734 |
| IFIT4 | OAS2 | IRF7 | 0.945691 |
| CIG5 | OAS3 | HERC5 | 0.945585 |
| IFIT4 | SAMD9L | CHMP5 | 0.945499 |
| IFIT5 | CIG5 | CHMP5 | 0.945489 |
| EPSTI1 | OAS1 | SP110 | 0.945479 |
| IRF7 | TYKI | RIGE | 0.945447 |
| RIG1 | IFI44 | MX1 | 0.945413 |
| EPSTI1 | IFIT1 | RIGE | 0.945395 |
| IFIT4 | OAS2 | PARP9 | 0.945338 |
| IFI44L | RIG1 | G1P2 | 0.945334 |
| IFI44 | OAS3 | CHMP5 | 0.945317 |
| OAS2 | OAS1 | ZBP1 | 0.945291 |
| RIG1 | OAS3 | TYKI | 0.945221 |
| SAMD9L | CHMP5 | XIAP | 0.945205 |
| PARP9 | SAMD9L | RIGE | 0.945185 |
| OAS2 | G1P2 | OASL | 0.944851 |
| PARP9 | CHMP5 | XIAP | 0.944816 |
| IFIT4 | EPSTI1 | OASL | 0.944671 |
| IFI44L | OAS2 | IFI44 | 0.944632 |
| IFIT4 | PARP9 | ZBP1 | 0.944622 |
| EPSTI1 | CIG5 | XIAP | 0.944456 |
| RIG1 | OAS1 | OASL | 0.944438 |
| OAS1 | HERC5 | CHMP5 | 0.94431 |
| IFI44 | PARP9 | TYKI | 0.944208 |
| PARP9 | CHMP5 | SP110 | 0.944124 |
| IFIT1 | SP110 | ZBP1 | 0.944046 |
| IFI44L | CIG5 | CHMP5 | 0.943778 |
| IFIT5 | IFI44L | IFIT4 | 0.943771 |
| PARP9 | MX1 | SP110 | 0.943665 |
| RIG1 | CHMP5 | SP110 | 0.943533 |
| OAS2 | OASL | HERC5 | 0.9435 |
| OAS1 | OASL | ZBP1 | 0.9435 |
| IFIT4 | OAS2 | XIAP | 0.943449 |
| MX1 | RIGE | XIAP | 0.943426 |
| CIG5 | TYKI | RIGE | 0.943328 |
| EPSTI1 | IRF7 | CIG5 | 0.943287 |
| IRF7 | HERC5 | RIGE | 0.943132 |
| RIG1 | PARP9 | MX1 | 0.942814 |
| OAS2 | HERC5 | ZBP1 | 0.942715 |
| IFIT4 | RIG1 | PARP9 | 0.942684 |
| SAMD9L | CHMP5 | MX1 | 0.942597 |
| OASL | SAMD9L | SP110 | 0.942585 |
| G1P2 | OAS3 | PARP9 | 0.942554 |
| OAS1 | IFI44 | TYKI | 0.942437 |
| OASL | IFIT1 | SP110 | 0.942318 |
| IFI44L | EPSTI1 | IFI44 | 0.942267 |
| OAS3 | SAMD9L | ZBP1 | 0.942149 |
| OAS1 | PARP9 | SP110 | 0.942068 |
| OAS1 | SP110 | XIAP | 0.942012 |
| IFI44L | RIG1 | TYKI | 0.94201 |
| IFIT5 | OAS1 | PARP9 | 0.94199 |
| G1P2 | OASL | SP110 | 0.941717 |
| IFI44 | SAMD9L | TYKI | 0.941631 |
| IFIT4 | CIG5 | ZBP1 | 0.941466 |
| EPSTI1 | HERC5 | RIGE | 0.941431 |
| IFIT5 | OAS1 | TYKI | 0.941419 |
| IFIT5 | EPSTI1 | IFI44 | 0.941395 |
| IFI44L | OAS1 | SAMD9L | 0.941117 |
| OAS2 | OASL | MX1 | 0.941065 |
| IFIT5 | CHMP5 | ZBP1 | 0.940941 |
| OAS2 | G1P2 | SP110 | 0.940753 |
| OAS3 | PARP9 | MX1 | 0.940695 |
| OASL | IFI44 | CHMP5 | 0.940462 |
| RIG1 | IFI44 | IFIT1 | 0.940444 |
| IRF7 | XIAP | ZBP1 | 0.940387 |
| IFIT4 | OAS3 | XIAP | 0.940303 |
| OAS1 | TYKI | CHMP5 | 0.940259 |
| HERC5 | SP110 | ZBP1 | 0.940142 |
| G1P2 | CIG5 | OAS3 | 0.939919 |
| OAS1 | IFI44 | PARP9 | 0.939836 |
| IFIT4 | PARP9 | CHMP5 | 0.9396 |
| RIG1 | IFI44 | HERC5 | 0.939599 |
| IFIT4 | IRF7 | OAS3 | 0.939488 |
| G1P2 | IRF7 | RIGE | 0.939474 |
| IFIT5 | IFI44L | XIAP | 0.939166 |
| EPSTI1 | OAS1 | RIGE | 0.938921 |
| RIG1 | PARP9 | XIAP | 0.938797 |
| EPSTI1 | IRF7 | ZBP1 | 0.938775 |
| IFIT5 | OAS2 | CHMP5 | 0.938637 |
| IFIT4 | OASL | CIG5 | 0.938552 |
| EPSTI1 | MX1 | RIGE | 0.938432 |
| IFIT5 | IFI44L | IRF7 | 0.938421 |
| OASL | PARP9 | XIAP | 0.938359 |
| IFIT5 | IFI44L | MX1 | 0.93825 |
| CIG5 | IFIT1 | RIGE | 0.938229 |
| EPSTI1 | RIG1 | PARP9 | 0.938162 |
| IFIT5 | RIG1 | TYKI | 0.938067 |
| IFI44 | PARP9 | SAMD9L | 0.937964 |
| IRF7 | PARP9 | CHMP5 | 0.937956 |
| SAMD9L | CHMP5 | IFIT1 | 0.937945 |
| IFI44L | IFI44 | SP110 | 0.937911 |
| OAS3 | TYKI | ZBP1 | 0.937748 |
| IFIT4 | OAS3 | PARP9 | 0.937712 |
| CIG5 | OAS3 | MX1 | 0.937685 |
| IFI44L | CHMP5 | ZBP1 | 0.937606 |
| RIG1 | OAS1 | PARP9 | 0.937438 |
| OAS2 | SAMD9L | SP110 | 0.937426 |
| IRF7 | MX1 | RIGE | 0.937279 |
| OAS2 | OAS1 | OASL | 0.937248 |
| RIG1 | IFIT1 | RIGE | 0.93718 |
| OAS2 | MX1 | ZBP1 | 0.937132 |
| G1P2 | SAMD9L | CHMP5 | 0.936982 |
| EPSTI1 | XIAP | ZBP1 | 0.936697 |
| RIG1 | G1P2 | IFI44 | 0.936637 |
| OAS1 | CIG5 | RIGE | 0.936614 |
| OASL | IRF7 | XIAP | 0.936603 |
| PARP9 | IFIT1 | RIGE | 0.936593 |
| HERC5 | SAMD9L | CHMP5 | 0.93654 |
| IFIT4 | SP110 | XIAP | 0.936501 |
| IFIT4 | OAS2 | EPSTI1 | 0.936231 |
| RIG1 | CIG5 | PARP9 | 0.936225 |
| IFIT4 | EPSTI1 | OAS3 | 0.936192 |
| IFIT5 | IFI44 | SP110 | 0.936081 |
| PARP9 | CHMP5 | IFIT1 | 0.935858 |
| SAMD9L | TYKI | CHMP5 | 0.935842 |
| OAS2 | IFIT1 | SP110 | 0.935741 |
| OAS1 | IRF7 | RIGE | 0.935686 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| OASL | OAS3 | SAMD9L | 0.935639 |
| CIG5 | HERC5 | RIGE | 0.935444 |
| OAS1 | RIGE | XIAP | 0.935361 |
| G1P2 | CIG5 | RIGE | 0.935304 |
| IFIT5 | IFI44L | IFIT1 | 0.935275 |
| PARP9 | CHMP5 | MX1 | 0.935232 |
| RIG1 | OAS3 | MX1 | 0.935175 |
| IFI44L | OAS2 | CHMP5 | 0.934781 |
| RIG1 | OAS1 | OAS3 | 0.934681 |
| OASL | HERC5 | SP110 | 0.934566 |
| PARP9 | TYKI | CHMP5 | 0.934504 |
| OAS3 | IFIT1 | ZBP1 | 0.934375 |
| SAMD9L | RIGE | ZBP1 | 0.934283 |
| HERC5 | PARP9 | CHMP5 | 0.93411 |
| IFIT5 | IFIT4 | IFI44 | 0.934012 |
| EPSTI1 | OASL | PARP9 | 0.933922 |
| OAS3 | TYKI | SP110 | 0.933864 |
| CIG5 | IFI44 | CHMP5 | 0.933838 |
| MX1 | SP110 | ZBP1 | 0.933692 |
| RIG1 | CHMP5 | XIAP | 0.933629 |
| OAS1 | IFI44 | SAMD9L | 0.933607 |
| IFI44L | IFIT4 | IFI44 | 0.933553 |
| PARP9 | TYKI | RIGE | 0.933515 |
| IFIT4 | IRF7 | SP110 | 0.933498 |
| OAS2 | EPSTI1 | PARP9 | 0.933446 |
| OAS1 | SP110 | ZBP1 | 0.933405 |
| OAS2 | PARP9 | XIAP | 0.933338 |
| IFIT5 | EPSTI1 | CHMP5 | 0.933165 |
| EPSTI1 | OASL | XIAP | 0.933115 |
| IFIT4 | OASL | ZBP1 | 0.933099 |
| EPSTI1 | PARP9 | ZBP1 | 0.932945 |
| IFI44L | EPSTI1 | CHMP5 | 0.932873 |
| OASL | OAS3 | IFIT1 | 0.932774 |
| PARP9 | XIAP | ZBP1 | 0.932749 |
| EPSTI1 | RIG1 | CIG5 | 0.93261 |
| IFIT5 | OAS1 | SAMD9L | 0.932602 |
| OASL | MX1 | SP110 | 0.932194 |
| IFIT4 | OAS2 | RIG1 | 0.932084 |
| RIG1 | TYKI | RIGE | 0.932067 |
| RIG1 | IRF7 | ZBP1 | 0.931911 |
| EPSTI1 | OASL | IRF7 | 0.931811 |
| RIG1 | G1P2 | OAS3 | 0.931711 |
| OAS2 | IRF7 | PARP9 | 0.931653 |
| IFI44L | RIG1 | OAS1 | 0.931477 |
| G1P2 | PARP9 | CHMP5 | 0.931468 |
| IFIT5 | RIG1 | PARP9 | 0.931134 |
| IFIT5 | IFI44L | HERC5 | 0.931073 |
| RIG1 | IRF7 | CHMP5 | 0.930931 |
| IFIT5 | IFI44 | XIAP | 0.930929 |
| OAS3 | SAMD9L | SP110 | 0.930851 |
| OASL | OAS3 | TYKI | 0.930816 |
| IFIT5 | IFI44 | MX1 | 0.930811 |
| IRF7 | CIG5 | ZBP1 | 0.930782 |
| RIG1 | IFI44 | TYKI | 0.930705 |
| IFI44L | IFI44 | XIAP | 0.930504 |
| OASL | IRF7 | PARP9 | 0.930323 |
| CIG5 | XIAP | ZBP1 | 0.930024 |
| IFIT5 | IFI44L | G1P2 | 0.929939 |
| OAS1 | OAS3 | ZBP1 | 0.92992 |
| IFIT4 | RIG1 | CHMP5 | 0.929849 |
| OAS2 | HERC5 | SP110 | 0.929752 |
| CIG5 | MX1 | RIGE | 0.929631 |
| RIG1 | HERC5 | RIGE | 0.929627 |
| HERC5 | PARP9 | RIGE | 0.929502 |
| IFI44L | RIG1 | SAMD9L | 0.929277 |
| OAS3 | HERC5 | ZBP1 | 0.929262 |
| IFIT4 | PARP9 | SP110 | 0.929202 |
| IFI44L | IFI44 | MX1 | 0.929036 |
| OAS1 | PARP9 | CHMP5 | 0.928969 |
| IFI44L | IRF7 | IFI44 | 0.928905 |
| TYKI | RIGE | ZBP1 | 0.928873 |
| IFIT5 | IRF7 | IFI44 | 0.928864 |
| IFIT4 | OAS2 | CIG5 | 0.928862 |
| G1P2 | PARP9 | RIGE | 0.928789 |
| IFI44L | RIG1 | PARP9 | 0.928757 |
| IFI44 | CHMP5 | ZBP1 | 0.928586 |
| OAS2 | OAS3 | TYKI | 0.928574 |
| OASL | CIG5 | PARP9 | 0.928457 |
| IFI44L | CHMP5 | SP110 | 0.928425 |
| IFIT5 | CHMP5 | SP110 | 0.92804 |
| OAS2 | OAS3 | SAMD9L | 0.928004 |
| RIG1 | OAS1 | SP110 | 0.927916 |
| IRF7 | PARP9 | ZBP1 | 0.927757 |
| RIG1 | CHMP5 | MX1 | 0.927685 |
| OASL | CIG5 | XIAP | 0.927452 |
| IFIT5 | IFI44 | IFIT1 | 0.927301 |
| RIG1 | G1P2 | RIGE | 0.927147 |
| OAS1 | PARP9 | RIGE | 0.926871 |
| CIG5 | PARP9 | ZBP1 | 0.926818 |
| OAS2 | EPSTI1 | IRF7 | 0.926537 |
| OAS3 | IFIT1 | SP110 | 0.926516 |
| OAS2 | IRF7 | XIAP | 0.926247 |
| OAS2 | MX1 | SP110 | 0.926135 |
| IFI44L | IFI44 | IFIT1 | 0.926123 |
| OAS1 | SAMD9L | CHMP5 | 0.925906 |
| OAS2 | CIG5 | PARP9 | 0.925828 |
| EPSTI1 | OAS3 | PARP9 | 0.925671 |
| G1P2 | OAS3 | ZBP1 | 0.925573 |
| IFIT1 | RIGE | ZBP1 | 0.925539 |
| IFIT4 | RIGE | XIAP | 0.925317 |
| OAS2 | IFI44 | CHMP5 | 0.925256 |
| RIG1 | XIAP | ZBP1 | 0.925255 |
| OASL | IRF7 | CIG5 | 0.925231 |
| OASL | OAS3 | HERC5 | 0.92508 |
| IFIT5 | IFI44L | TYKI | 0.924932 |
| EPSTI1 | RIG1 | ZBP1 | 0.924695 |
| IFIT5 | RIG1 | SAMD9L | 0.924337 |
| OAS2 | OAS3 | IFIT1 | 0.924255 |
| IFI44L | IFI44 | HERC5 | 0.924174 |
| RIG1 | IRF7 | PARP9 | 0.923945 |
| EPSTI1 | CIG5 | ZBP1 | 0.923914 |
| OAS2 | OAS1 | SP110 | 0.923858 |
| IFIT5 | IFI44 | HERC5 | 0.923703 |
| IFIT5 | G1P2 | IFI44 | 0.923603 |
| RIG1 | MX1 | RIGE | 0.923568 |
| IFIT4 | CIG5 | OAS3 | 0.92356 |
| IFIT5 | IFIT4 | CHMP5 | 0.923303 |
| EPSTI1 | IFI44 | CHMP5 | 0.923176 |
| IFIT4 | RIG1 | OAS3 | 0.923081 |
| RIG1 | OASL | XIAP | 0.922837 |
| RIG1 | CHMP5 | IFIT1 | 0.922695 |
| PARP9 | MX1 | RIGE | 0.922687 |
| OAS2 | SAMD9L | RIGE | 0.922634 |
| IFIT5 | IFI44L | PARP9 | 0.92262 |
| IFIT4 | EPSTI1 | SP110 | 0.922466 |
| IFI44L | G1P2 | IFI44 | 0.922343 |
| OAS3 | PARP9 | XIAP | 0.921953 |
| OAS2 | EPSTI1 | XIAP | 0.921908 |
| OAS2 | TYKI | RIGE | 0.921747 |
| IFIT4 | OAS2 | ZBP1 | 0.921651 |
| RIG1 | HERC5 | CHMP5 | 0.92161 |
| IFI44L | IFIT4 | CHMP5 | 0.921594 |
| EPSTI1 | IRF7 | OAS3 | 0.921499 |
| RIG1 | OASL | IRF7 | 0.921365 |
| G1P2 | RIGE | ZBP1 | 0.921333 |
| PARP9 | SAMD9L | CHMP5 | 0.92129 |
| IFIT5 | CHMP5 | XIAP | 0.921284 |
| OAS3 | MX1 | ZBP1 | 0.921266 |
| RIG1 | TYKI | CHMP5 | 0.92113 |
| IFIT4 | OAS2 | OASL | 0.921102 |
| RIG1 | OAS1 | IFI44 | 0.921011 |
| OASL | SAMD9L | RIGE | 0.92072 |
| OAS3 | HERC5 | SP110 | 0.920417 |
| EPSTI1 | OAS3 | XIAP | 0.920342 |
| IFIT5 | CHMP5 | MX1 | 0.920248 |
| OASL | OAS3 | MX1 | 0.920206 |
| G1P2 | OAS3 | SP110 | 0.920122 |
| G1P2 | OASL | OAS3 | 0.920062 |

TABLE 4B-continued

All possible 3-gene combinations of a selected group of 24 genes, indicated with their respective Pearson correlation values.

| Gene 1 | Gene 2 | Gene 3 | Pearson Correlation |
| --- | --- | --- | --- |
| IFIT4 | CIG5 | SP110 | 0.919544 |
| IFI44L | CHMP5 | XIAP | 0.919301 |
| EPSTI1 | OASL | CIG5 | 0.91928 |
| OAS1 | OASL | SP110 | 0.919179 |
| IFIT5 | IRF7 | CHMP5 | 0.919067 |
| OAS2 | OAS1 | OAS3 | 0.918994 |
| IFI44L | IFI44 | TYKI | 0.918961 |
| OAS1 | OASL | OAS3 | 0.918852 |
| HERC5 | RIGE | ZBP1 | 0.918551 |
| OASL | IFIT1 | RIGE | 0.91841 |
| IFIT5 | RIG1 | OAS1 | 0.91814 |
| OAS2 | IRF7 | CIG5 | 0.918041 |
| IRF7 | OAS3 | XIAP | 0.918037 |
| IFIT5 | IFI44 | TYKI | 0.917786 |
| OAS1 | RIGE | ZBP1 | 0.917732 |
| RIG1 | G1P2 | CHMP5 | 0.917667 |
| IFI44L | IRF7 | CHMP5 | 0.917628 |
| OAS2 | IFIT1 | RIGE | 0.917465 |
| OAS2 | OAS3 | HERC5 | 0.91737 |
| IRF7 | OAS3 | PARP9 | 0.917026 |
| IFI44L | CHMP5 | MX1 | 0.916997 |
| IFIT4 | IRF7 | RIGE | 0.916887 |
| IFIT4 | RIG1 | SP110 | 0.916864 |
| IFIT5 | CHMP5 | IFIT1 | 0.916571 |
| OASL | TYKI | RIGE | 0.916429 |
| IFIT4 | EPSTI1 | RIGE | 0.916258 |
| EPSTI1 | RIG1 | OASL | 0.916184 |
| RIG1 | IFI44 | PARP9 | 0.916107 |
| IFIT5 | IFI44L | OAS1 | 0.915943 |
| RIG1 | IFI44 | SAMD9L | 0.915918 |
| IFI44 | CHMP5 | SP110 | 0.915791 |
| PARP9 | SP110 | XIAP | 0.915523 |
| RIG1 | OAS1 | RIGE | 0.915317 |
| OAS2 | CIG5 | XIAP | 0.915027 |
| IFIT5 | IFI44L | SAMD9L | 0.914239 |
| IFI44L | CHMP5 | IFIT1 | 0.914106 |
| IFIT5 | IFI44 | PARP9 | 0.913922 |
| OAS1 | OAS3 | SP110 | 0.913805 |
| IFI44L | OAS1 | IFI44 | 0.913685 |
| OAS2 | G1P2 | OAS3 | 0.913341 |
| OAS3 | MX1 | SP110 | 0.913024 |
| MX1 | RIGE | ZBP1 | 0.91295 |
| IFI44L | IFI44 | PARP9 | 0.912714 |
| RIG1 | CIG5 | ZBP1 | 0.912402 |
| IFIT5 | HERC5 | CHMP5 | 0.912293 |
| IFIT4 | SP110 | ZBP1 | 0.912203 |
| CIG5 | OAS3 | PARP9 | 0.912168 |
| IFIT5 | G1P2 | CHMP5 | 0.912138 |
| IFIT4 | OAS3 | ZBP1 | 0.912117 |
| IFIT4 | IFI44 | CHMP5 | 0.912012 |
| OAS2 | RIG1 | IRF7 | 0.911984 |
| IRF7 | SP110 | XIAP | 0.911965 |
| TYKI | SP110 | RIGE | 0.9118 |
| IFI44L | HERC5 | CHMP5 | 0.911777 |
| OAS2 | OAS3 | MX1 | 0.91137 |
| OAS2 | G1P2 | RIGE | 0.911317 |
| IFIT4 | PARP9 | RIGE | 0.911158 |
| IFI44 | CHMP5 | XIAP | 0.910766 |
| OAS2 | EPSTI1 | CIG5 | 0.910517 |
| OASL | IRF7 | ZBP1 | 0.910488 |
| OASL | XIAP | ZBP1 | 0.909994 |
| IFI44L | TYKI | CHMP5 | 0.909904 |
| EPSTI1 | PARP9 | SP110 | 0.909711 |
| IFI44 | CHMP5 | MX1 | 0.909689 |
| IFIT5 | TYKI | CHMP5 | 0.90968 |
| G1P2 | OASL | RIGE | 0.90961 |
| IFI44L | G1P2 | CHMP5 | 0.909576 |
| IFIT5 | OAS1 | IFI44 | 0.909388 |
| IFIT4 | CIG5 | RIGE | 0.908925 |
| OAS2 | OAS1 | RIGE | 0.908806 |
| OAS2 | HERC5 | RIGE | 0.908751 |
| OASL | HERC5 | RIGE | 0.908541 |
| CIG5 | PARP9 | SP110 | 0.908525 |
| EPSTI1 | OASL | ZBP1 | 0.908429 |
| RIG1 | OAS1 | CHMP5 | 0.90836 |
| IFI44L | IFI44 | SAMD9L | 0.907964 |
| IRF7 | IFI44 | CHMP5 | 0.907863 |
| CIG5 | OAS3 | XIAP | 0.907513 |
| IRF7 | CIG5 | OAS3 | 0.907333 |
| IFIT4 | OASL | OAS3 | 0.906832 |
| RIG1 | OASL | CIG5 | 0.90659 |
| SAMD9L | SP110 | RIGE | 0.906569 |
| EPSTI1 | SP110 | XIAP | 0.906534 |
| IFIT5 | IFI44 | SAMD9L | 0.90643 |
| EPSTI1 | CIG5 | OAS3 | 0.906354 |
| IFI44 | CHMP5 | IFIT1 | 0.906304 |
| OASL | MX1 | RIGE | 0.906245 |
| IRF7 | PARP9 | SP110 | 0.906101 |
| EPSTI1 | IRF7 | SP110 | 0.906008 |
| IFIT4 | OASL | SP110 | 0.905978 |
| OAS2 | MX1 | RIGE | 0.90518 |
| CIG5 | SP110 | XIAP | 0.90499 |
| IFIT1 | SP110 | RIGE | 0.904324 |
| IFI44 | HERC5 | CHMP5 | 0.904282 |
| RIG1 | OASL | PARP9 | 0.904259 |
| OAS3 | SAMD9L | RIGE | 0.904065 |
| IFI44L | OAS1 | CHMP5 | 0.903581 |
| IRF7 | CIG5 | SP110 | 0.903302 |
| G1P2 | IFI44 | CHMP5 | 0.903298 |
| G1P2 | SP110 | RIGE | 0.903287 |
| OAS2 | EPSTI1 | RIG1 | 0.903249 |
| OASL | PARP9 | ZBP1 | 0.902995 |
| OAS2 | OASL | PARP9 | 0.902848 |
| IFI44 | TYKI | CHMP5 | 0.902228 |
| OAS1 | OASL | RIGE | 0.901099 |
| OAS2 | IRF7 | ZBP1 | 0.900596 |
| OAS2 | RIG1 | PARP9 | 0.900166 |
| OAS3 | IFIT1 | RIGE | 0.900065 |
| OASL | CIG5 | ZBP1 | 0.899594 |
| EPSTI1 | RIGE | XIAP | 0.899556 |
| IFIT5 | OAS1 | CHMP5 | 0.89953 |
| OAS2 | RIG1 | XIAP | 0.899013 |
| IFIT5 | PARP9 | CHMP5 | 0.898064 |
| OAS2 | OASL | IRF7 | 0.898064 |
| OAS3 | TYKI | RIGE | 0.897749 |
| OAS2 | EPSTI1 | ZBP1 | 0.897534 |
| IFIT4 | RIG1 | RIGE | 0.897168 |
| EPSTI1 | RIG1 | OAS3 | 0.896978 |
| OAS2 | PARP9 | ZBP1 | 0.896335 |
| IFIT4 | RIGE | ZBP1 | 0.896273 |
| OAS1 | IFI44 | CHMP5 | 0.896108 |
| IFIT5 | IFI44L | RIG1 | 0.895894 |
| IFI44L | PARP9 | CHMP5 | 0.895497 |
| IFIT4 | OAS2 | OAS3 | 0.895401 |
| OAS2 | EPSTI1 | OASL | 0.895303 |
| OAS2 | OASL | XIAP | 0.895129 |
| HERC5 | SP110 | RIGE | 0.894807 |
| EPSTI1 | CIG5 | SP110 | 0.894768 |
| IFIT4 | OAS2 | SP110 | 0.894337 |
| IRF7 | RIGE | XIAP | 0.8943 |
| RIG1 | SAMD9L | CHMP5 | 0.89381 |
| IFI44L | SAMD9L | CHMP5 | 0.893745 |
| PARP9 | RIGE | XIAP | 0.89358 |
| OAS2 | XIAP | ZBP1 | 0.893376 |
| EPSTI1 | IRF7 | RIGE | 0.893012 |
| EPSTI1 | PARP9 | RIGE | 0.892978 |
| IFIT5 | SAMD9L | CHMP5 | 0.892943 |
| RIG1 | PARP9 | ZBP1 | 0.892935 |
| CIG5 | RIGE | XIAP | 0.892719 |
| IFIT4 | OAS3 | SP110 | 0.891861 |
| MX1 | SP110 | RIGE | 0.891301 |
| OAS3 | HERC5 | RIGE | 0.891101 |
| RIG1 | IRF7 | OAS3 | 0.890525 |
| OAS2 | RIG1 | CIG5 | 0.890495 |
| EPSTI1 | OAS3 | ZBP1 | 0.890069 |
| OAS1 | OAS3 | RIGE | 0.89006 |
| IFI44L | RIG1 | IFI44 | 0.88778 |
| IFIT5 | IFI44L | IFI44 | 0.88776 |

TABLE 4B-continued

All possible 3-gene combinations of a selected group of 24 genes, indicated with their respective Pearson correlation values.

| Gene 1 | Gene 2 | Gene 3 | Pearson Correlation |
|---|---|---|---|
| RIG1 | OAS3 | XIAP | 0.887549 |
| IFI44 | PARP9 | CHMP5 | 0.887524 |
| G1P2 | OAS3 | RIGE | 0.887416 |
| EPSTI1 | CIG5 | RIGE | 0.887118 |
| OAS2 | CIG5 | ZBP1 | 0.886902 |
| OAS1 | SP110 | RIGE | 0.88684 |
| CIG5 | PARP9 | RIGE | 0.886773 |
| OAS2 | OASL | CIG5 | 0.886112 |
| IFI44 | SAMD9L | CHMP5 | 0.885956 |
| IFIT4 | OASL | RIGE | 0.885918 |
| IFIT5 | RIG1 | IFI44 | 0.885771 |
| IRF7 | CIG5 | RIGE | 0.885643 |
| IRF7 | OAS3 | ZBP1 | 0.885583 |
| OAS3 | MX1 | RIGE | 0.885561 |
| EPSTI1 | OASL | OAS3 | 0.883489 |
| IRF7 | SP110 | ZBP1 | 0.883248 |
| OAS3 | XIAP | ZBP1 | 0.883087 |
| RIG1 | PARP9 | CHMP5 | 0.882158 |
| IFIT4 | OAS2 | RIGE | 0.881223 |
| SP110 | XIAP | ZBP1 | 0.881076 |
| OASL | OAS3 | PARP9 | 0.880696 |
| OAS3 | PARP9 | ZBP1 | 0.880421 |
| RIG1 | IRF7 | SP110 | 0.880086 |
| EPSTI1 | SP110 | ZBP1 | 0.879636 |
| RIG1 | OASL | ZBP1 | 0.879626 |
| IRF7 | PARP9 | RIGE | 0.87949 |
| OASL | OAS3 | XIAP | 0.879447 |
| RIG1 | SP110 | XIAP | 0.879006 |
| OASL | IRF7 | OAS3 | 0.878692 |
| RIG1 | OAS3 | PARP9 | 0.878538 |
| OASL | SP110 | XIAP | 0.876723 |
| OASL | PARP9 | SP110 | 0.875724 |
| RIG1 | CIG5 | OAS3 | 0.875511 |
| CIG5 | OAS3 | ZBP1 | 0.875241 |
| OASL | IRF7 | SP110 | 0.874351 |
| PARP9 | SP110 | ZBP1 | 0.873999 |
| OAS2 | OAS3 | PARP9 | 0.873713 |
| CIG5 | SP110 | ZBP1 | 0.873581 |
| IFIT5 | IFI44L | CHMP5 | 0.873435 |
| EPSTI1 | OASL | SP110 | 0.872477 |
| OAS2 | EPSTI1 | OAS3 | 0.872405 |
| OAS2 | PARP9 | SP110 | 0.87155 |
| EPSTI1 | RIG1 | SP110 | 0.871342 |
| OASL | CIG5 | OAS3 | 0.870785 |
| RIG1 | CIG5 | SP110 | 0.869263 |
| EPSTI1 | RIGE | ZBP1 | 0.868804 |
| IFIT4 | OAS3 | RIGE | 0.868713 |
| OASL | CIG5 | SP110 | 0.867945 |
| IFI44L | IFI44 | CHMP5 | 0.867675 |
| OAS2 | IRF7 | OAS3 | 0.867456 |
| IFIT5 | IFI44 | CHMP5 | 0.867157 |
| RIGE | XIAP | ZBP1 | 0.866861 |
| IFI44L | RIG1 | CHMP5 | 0.864815 |
| OAS2 | IRF7 | SP110 | 0.863904 |
| IFIT5 | RIG1 | CHMP5 | 0.863765 |
| OAS2 | OAS3 | XIAP | 0.862892 |
| OAS2 | OASL | ZBP1 | 0.862277 |
| EPSTI1 | OAS3 | SP110 | 0.861466 |
| IRF7 | RIGE | ZBP1 | 0.861372 |
| OAS3 | PARP9 | SP110 | 0.861136 |
| EPSTI1 | RIG1 | RIGE | 0.860936 |
| IFIT4 | SP110 | RIGE | 0.860801 |
| RIG1 | RIGE | XIAP | 0.860302 |
| OAS2 | EPSTI1 | SP110 | 0.860174 |
| CIG5 | RIGE | ZBP1 | 0.859596 |
| OAS2 | SP110 | XIAP | 0.858564 |
| EPSTI1 | OASL | RIGE | 0.857914 |
| OAS2 | RIG1 | OASL | 0.857565 |
| OASL | RIGE | XIAP | 0.857553 |
| OAS2 | CIG5 | OAS3 | 0.857493 |
| IRF7 | OAS3 | SP110 | 0.857288 |
| OAS3 | SP110 | XIAP | 0.856743 |
| RIG1 | IFI44 | CHMP5 | 0.855689 |
| OAS2 | RIG1 | ZBP1 | 0.85545 |
| RIG1 | PARP9 | SP110 | 0.855367 |
| OAS2 | CIG5 | SP110 | 0.854157 |
| OAS2 | EPSTI1 | RIGE | 0.852592 |
| PARP9 | RIGE | ZBP1 | 0.852095 |
| OASL | CIG5 | RIGE | 0.850683 |
| RIG1 | CIG5 | RIGE | 0.850622 |
| OASL | IRF7 | RIGE | 0.849649 |
| CIG5 | OAS3 | SP110 | 0.849016 |
| OAS2 | RIGE | XIAP | 0.848472 |
| OASL | PARP9 | RIGE | 0.847797 |
| RIG1 | IRF7 | RIGE | 0.847049 |
| OAS2 | PARP9 | RIGE | 0.84672 |
| OAS2 | IRF7 | RIGE | 0.844908 |
| OASL | OAS3 | ZBP1 | 0.843861 |
| OAS2 | CIG5 | RIGE | 0.84326 |
| EPSTI1 | OAS3 | RIGE | 0.843087 |
| OASL | SP110 | ZBP1 | 0.840384 |
| OAS3 | RIGE | XIAP | 0.835809 |
| RIG1 | OAS3 | ZBP1 | 0.835232 |
| CIG5 | OAS3 | RIGE | 0.830689 |
| IRF7 | OAS3 | RIGE | 0.830055 |
| RIG1 | OASL | OAS3 | 0.829875 |
| OAS3 | PARP9 | RIGE | 0.829849 |
| RIG1 | PARP9 | RIGE | 0.827293 |
| RIG1 | SP110 | ZBP1 | 0.827103 |
| OAS2 | OAS3 | ZBP1 | 0.825923 |
| OAS2 | OASL | OAS3 | 0.825647 |
| EPSTI1 | SP110 | RIGE | 0.824627 |
| SP110 | RIGE | XIAP | 0.823548 |
| OASL | RIGE | ZBP1 | 0.821675 |
| OAS2 | SP110 | ZBP1 | 0.821066 |
| OAS2 | OASL | SP110 | 0.820454 |
| CIG5 | SP110 | RIGE | 0.819918 |
| RIG1 | OASL | SP110 | 0.818533 |
| OAS3 | SP110 | ZBP1 | 0.814438 |
| IRF7 | SP110 | RIGE | 0.814248 |
| PARP9 | SP110 | RIGE | 0.812561 |
| OAS2 | RIGE | ZBP1 | 0.810229 |
| OASL | OAS3 | SP110 | 0.809037 |
| RIG1 | RIGE | ZBP1 | 0.806619 |
| OAS2 | OASL | RIGE | 0.804693 |
| OAS2 | RIG1 | OAS3 | 0.803515 |
| OAS3 | RIGE | ZBP1 | 0.79653 |
| RIG1 | OASL | RIGE | 0.79316 |
| OASL | OAS3 | RIGE | 0.789533 |
| OAS2 | OAS3 | SP110 | 0.789077 |
| OAS2 | RIG1 | SP110 | 0.78802 |
| RIG1 | OAS3 | SP110 | 0.785883 |
| SP110 | RIGE | ZBP1 | 0.781728 |
| OAS2 | RIG1 | RIGE | 0.777652 |
| OAS2 | OAS3 | RIGE | 0.7757 |
| OASL | SP110 | RIGE | 0.772656 |
| RIG1 | OAS3 | RIGE | 0.761256 |
| OAS2 | SP110 | RIGE | 0.75784 |
| OAS3 | SP110 | RIGE | 0.7529 |
| RIG1 | SP110 | RIGE | 0.725531 |

The invention claimed is:

1. A method of treating a human having systemic lupus erythematous (SLE) with an anti-interferon-alpha antibody, comprising:
   (a) performing a nucleic acid-based detection assay to detect the mRNA expression level of at least three genes comprising EPSTI1, HERC5, and TYKI in cells of a blood sample from the human, wherein said at least three genes does not comprise OASL, CHMP5, and ZBP1;
   (b) determining that the cells from the human express said at least three genes comprising EPSTI1, HERC5, and TYKI at a level greater than the expression level of the respective genes in cells of a blood sample from a healthy human control; and (c) administering an effective amount of the anti-interferon-alpha antibody to the human expressing the at least three genes comprising EPSTI1, HERC5, and TYKI at a level greater than the expression level of the respective genes in cells of a blood sample from a healthy human control, thereby treating SLE in said human.

2. The method of claim 1, wherein the method comprises administering the anti-interferon-alpha antibody to said human in combination with a second therapeutic agent.

3. The method of claim 2, wherein the second therapeutic agent is a steroid.

4. The method of claim 1, further comprising assessing expression level of a housekeeping gene in the cells as an indicator of baseline gene expression.

5. The method of claim 4, wherein the housekeeping gene is ribosomal protein L19.

6. The method of claim 1, wherein the anti-interferon-alpha antibody is a monoclonal antibody.

7. The method of claim 1, wherein the performing a nucleic acid-based detection assay comprises performing a nucleic acid hybridization assay.

8. The method of claim 1, wherein the performing a nucleic acid-based detection assay comprises performing a nucleic acid amplification assay.

\* \* \* \* \*